United States Patent
Zhang et al.

(10) Patent No.: US 7,585,888 B2
(45) Date of Patent: Sep. 8, 2009

(54) BENZOFURAN AND BENZOTHIOPHENE DERIVATIVES USEFUL IN THE TREATMENT OF HYPER-PROLIFERATIVE DISORDERS

(75) Inventors: Chengzhi Zhang, Orange, CT (US); Michael J. Burke, New Haven, CT (US); Zhi Chen, Hamden, CT (US); Jacques P. Dumas, Bethany, CT (US); Dongping Fan, North Haven, CT (US); Jianmei Fan, Hamden, CT (US); Holia Hatoum-Mokdad, Hamden, CT (US); Benjamin D. Jones, Hamden, CT (US); Gaetan Ladouceur, Guilford, CT (US); Wendy Lee, Hamden, CT (US); Barton Phillips, Hamden, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 0 days.

(21) Appl. No.: 12/059,984

(22) Filed: Mar. 31, 2008

(65) Prior Publication Data

US 2009/0054514 A1 Feb. 26, 2009

Related U.S. Application Data

(62) Division of application No. 10/501,689, filed as application No. PCT/US03/05396 on Feb. 21, 2003, now Pat. No. 7,351,735.

(60) Provisional application No. 60/399,886, filed on Jul. 31, 2002, provisional application No. 60/359,011, filed on Feb. 22, 2002.

(51) Int. Cl.
  *A61K 31/343* (2006.01)
  *A61K 31/381* (2006.01)
(52) U.S. Cl. ..................... 514/443; 514/470
(58) Field of Classification Search ............. 514/443, 514/470
  See application file for complete search history.

(56) References Cited

U.S. PATENT DOCUMENTS

| 5,466,810 A | 11/1995 | Godfrey |
| 5,504,213 A | 4/1996 | Fischer et al. |
| 5,565,488 A | 10/1996 | Braunlich et al. |
| 5,622,989 A | 4/1997 | Braunlich et al. |
| 5,691,359 A | 11/1997 | Fischer et al. |
| 5,922,740 A | 7/1999 | Braunlich et al. |

FOREIGN PATENT DOCUMENTS

| EP | 0551662 | 7/1993 |
| EP | 0731099 | 9/1996 |
| EP | 0801066 | 10/1997 |
| JP | 60072880 | 4/1985 |
| WO | WO 9802440 | 1/1998 |
| WO | WO 0069841 | 11/2000 |
| WO | WO 0069842 | 11/2000 |
| WO | WO 0069843 | 11/2000 |
| WO | WO 0069844 | 11/2000 |

OTHER PUBLICATIONS

Patent Abstracts of Japan, vol. 009, No. 205 (C-299), Aug. 22, 1985 and JP 60 072880 A (Kaken Seiyaku KK), Apr. 24, 1985.

Hayakawa, et al., "4-Hydroxy-3-Methyl-6-Phenylbenzofuran-2-Carboxylic Acid Ethyl Ester Derivatives as Potent Anti-Tumor Agents," Bioorg. Med. Chem. Lett., 14, 455-458 (2004).

Hayakawa, et al., "A Library Synthesis of 4-Hydroxy-3-Methyl-6-Phenylbenzofuran-2-Carboxylic Acid Ethyl Ester Derivatives as Anti-Tumor Agents," Bioorg. Med. Chem. Lett., 14, 4383-4387 (2004).

Hayakawa, et al., Thienopyridine and Benzofuran Derivatives as Potent Anti-Tumor Agents Possessing Different Structure-Activity Relationships,: Bioorg. Med. Chem. Lett., 14, 3411-3414 (2004).

*Primary Examiner*—Taofiq A Solola
(74) *Attorney, Agent, or Firm*—Christensen O'Connor Johnson Kindness PLLC

(57) ABSTRACT

This invention relates to novel benzofuran and benzothiophene derivatives of the general formula (I)

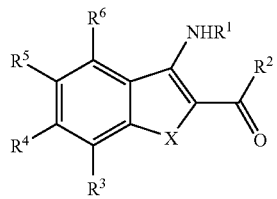

and their use for the treatment of hyper-proliferative disorders.

5 Claims, No Drawings

BENZOFURAN AND BENZOTHIOPHENE DERIVATIVES USEFUL IN THE TREATMENT OF HYPER-PROLIFERATIVE DISORDERS

CROSS-REFERENCE TO RELATED APPLICATIONS/PATENTS & INCORPORATION BY REFERENCE

This application is a divisional application of U.S. patent application Ser. No. 10/501,689, filed on Jul. 17, 2005, which was filed under 35 U.S.C. § 371 as a National Phase Application of International Application No. PCT/US03/05396, filed Feb. 21, 2003, which claims priority to U.S. Provisional Application Ser. No. 60/399,886, filed Jul. 31, 2002, and to U.S. Provisional Application Ser. No. 60/359,011, filed Feb. 22, 2002, the contents of each of which are incorporated herein by reference in their entireties.

Any and all references cited in the text of this patent application, including any U.S. or foreign patents or published patent applications, International patent applications, as well as, any non-patent literature reference, including any manufacturer's instructions, are hereby expressly incorporated by reference.

FIELD OF THE INVENTION

This invention relates to novel benzofuran and benzothiophene compounds, pharmaceutical compositions containing such compounds, and the use of those compounds and/or compositions for treating hyper-proliferative disorders.

DESCRIPTION OF THE INVENTION

Compounds of the Invention

One embodiment of this invention relates to a compound of Formula (I)

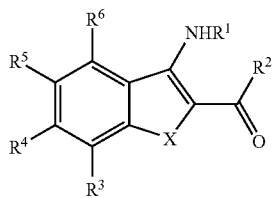

(I)

wherein

X is selected from O and S;

$R^1$ is selected from H, $(C_1-C_6)$alkyl, $C(O)(C_1-C_6)$alkyl, and benzoyl;

$R^2$ is selected from phenyl and naphthyl, each optionally substituted with 1, 2, or 3 substituents each independently selected from OH, CN, $NO_2$, $(C_1-C_6)$alkyl, $(C_1-C_6)$alkoxy, halo, halo$(C_1-C_6)$alkyl, halo$(C_1-C_6)$alkoxy, $C(O)R^A$, $C(O)NR^B R^B$, $NR^B R^B$, $NH[(C_1-C_6)alkyl,]_{0-1}S(O)_2R^B$, $NH[(C_1-C_6)alkyl]_{0-1}C(O)R^A$, and $NH[(C_1-C_6)alkyl]_{0-1}C(O)OR^B$, a heterocycle selected from a six membered heterocycle, a five membered heterocycle and a fused bicyclic heterocycle, each heterocycle being optionally substituted with 1, 2 or 3 substituents each independently selected from OH, CN, $NO_2$, $(C_1-C_6)$alkyl, $(C_1-C_6)$alkoxy, halo, halo$(C_1-C_6)$alkyl, halo$(C_1-C_6)$alkoxy, $C(O)R^A$, $C(O)NR^B R^B$, $NR^B R^B$, $NH[(C_1-C_6)alkyl,]_{0-1}S(O)_2R^B$, $NH[(C_1-C_6)alkyl]_{0-1}C(O)R^A$, and $NH[(C_1-C_6)alkyl]_{0-1}C(O)OR^B$, $R^A$ is in each instance independently H, $(C_1-C_6)$alkyl, $(C_1-C_6)$alkoxy, $NR^B R^B$, or $(C_1-C_5)$alkyl, said alkyl being optionally substituted with OH, $C(O)R^B$, halo, $(C_1-C_3)$alkoxy, and $NR^B R^B$;

$R^B$ is in each instance independently H, $(C_3-C_6)$cycloalkyl, and $(C_1-C_6)$alkyl, said alkyl being optionally substituted with OH, =O, halo, $(C_1-C_6)$alkoxy, $NH(C_1-C_3)$alkyl, $N[(C_1-C_3)alkyl]_2$, and $NC(O)(C_1-C_3)$alkyl, and where $R^B$, when it is attached to a N atom, is in each instance $(C_1-C_4)$alkyl, then the 2 $(C_1-C_4)$alkyl groups, taken together with the N atom to which they are attached, may be joined together to form a saturated ring, and where $R^B$ and $R^B$ together with the N to which they are attached may form a morpholinyl ring or a piperazinyl ring optionally substituted on the available N atom with $(C_1-C_6)$alkyl, said alkyl being optionally substituted with OH, =O, $NH_2$, $(C_1-C_6)$alkoxy, $NH(C_1-C_3)$alkyl, or $N[(C_1-C_3)alkyl]_2$, and with the proviso that when $R^B$ is attached to S(O) or to $S(O)_2$, it cannot be H;

$R^3$ is selected from H, OH, CN, $(C_1-C_3)$alkyl, $(C_1-C_3)$alkoxy, halo, halo$(C_1-C_3)$alkyl, and halo$(C_1-C_3)$alkoxy;

$R^4$ is selected from piperonyl,

Y where

Y is a heterocycle optionally substituted with 1, 2, or 3 substituents each independently selected from =O, N-oxide, H, CN, $NO_2$, halo, halo$(C_1-C_6)$alkyl, OH, halo$(C_1-C_6)$alkoxy, $C(O)OR^B$, $C(NH)NR^B R^B$, $NR^B R^B$, $S(O)_{0-2}R^B$, $S(O)_2NR^B R^B$, $(CO—C_6)$alkoxy, said alkoxy being optionally substituted with 1 or 2 substituents selected from OH, $NR^B R^B$, and $(C_1-C_3)$alkoxy, $NR^C R^C$ where $R^C$ is selected from $R^B$, $C(O)R^B$, and $S(O)_2 R^B$, $C(O)R^D$ where $R^D$ is selected from $R^A$, $(C_3-C_6)$cycloalkyl, Z and $N[(C_1-C_3)alkyl]Z$ where Z is in each instance a heterocycle independently optionally substituted with CN, =O, OH, N-oxide, $NO_2$, halo, $(C_1-C_6)$alkoxy, halo$(C_1-C_3)$alkoxy, halo$(C_1-C_3)$alkyl, $S(O)_2 R^B$, $S(O)_2 NR^B R^B$, $NR^B R^B$, $C(O)R^A$, and $(C_1-C_6)$alkyl, said alkyl being optionally substituted with OH, $C(O)R^B$, $(C_1-C_3)$alkoxy and $NR^B R^B$;

$NR^BR^E$ where
   $R^E$ is selected from $C(O)R^A$, $C(O)R^B$, $S(O)_2R^B$, $S(O)_2NR^BR^B$
   and $C(O)[(C_1-C_6)alkyl]Z$ where Z is optionally substituted as described above,
$(C_1-C_6)$alkyl, said alkyl being optionally substituted with
   CN, OH, =O, halo, $(C_1-C_6)$alkoxy, $C(O)R^A$, $NR^BR^B$, $NR^CR^C$,
   $NR^BR^E$, $C(NH)NR^BR^B$, $S(O)_{0-2}R^B$, $S(O)_2NR^BR^B$, $C(O)R^B$,
   $C(O)OR^B$, Z, $C(O)Z$, and $C(O)N[(C_1-C_3)alkyl]Z$, where Z in
   each instance is independently optionally substituted as described above,
phenyl and naphthyl each optionally substituted with 1, 2, or 3 substituents each independently selected from
   OH, CN, $NO_2$, halo, halo$(C_1-C_6)$alkyl, halo$(C_1-C_6)$alkoxy, $C(O)OR^B$,
   $C(NH)NR^BR^B$, $NR^BR^B$, $S(O)_{0-2}R^B$, $S(O)_2NR^BR^B$, Z, $C(O)Z$ where Z is in each instance optionally substituted as described above,
$(C_1-C_6)$alkoxy, said alkoxy being optionally substituted with 1 or 2 substituents selected from OH, $NR^BR^B$, and $(C_1-C_3)$alkoxy,
$NR^CR^C$ where
   $R^C$ is selected from $R^B$, $C(O)R^B$, and $S(O)_2R^B$,
$C(O)R^D$ where
   $R^D$ is selected from $R^A$, $(C_3-C_6)$cycloalkyl, and $N[(C_1-C_3)alkyl]Z$ where Z is optionally substituted as described above,
$NR^BR^E$ where
   $R^E$ is selected from $C(O)R^A$, $C(O)R^B$, $S(O)_2R^B$, $S(O)_2NR^BR^B$ and
   $C(O)[(C_1-C_6)alkyl]Z$ where Z is optionally substituted as described above,
$(C_1-C_6)$alkyl, said alkyl being optionally substituted with
   CN, OH, =O, halo, $(C_1-C_6)$alkoxy, $C(O)R^A$, $NR^BR^B$, $NR^BR^E$,
   $C(NH)NR^BR^B$, $S(O)_{0-2}R^B$, $S(O)_2NR^BR^B$, $C(O)R^B$, $C(O)OR^B$, Z, $C(O)Z$,
   and $C(O)N[(C_1-C_3)alkyl]Z$, where Z in each instance is
   independently optionally substituted as described above;
$R^5$ and $R^6$ are each independently selected from H, OH, CN, $(C_1-C_3)$alkyl, $(C_1-C_3)$alkoxy, halo, halo$(C_1-C_3)$alkyl, and halo$(C_1-C_3)$alkoxy;
or a pharmaceutically acceptable salt or ester thereof.

The terms identified above have the following meaning throughout:

The term "optionally substituted" means that the moiety so modified may have from none to up to about the highest number of substituents indicated. When there are two or more substituents on any moiety, each substituent is defined independently of any other substituent and can, accordingly, be the same or different.

The term "$(C_1-C_6)$alkyl, said alkyl being optionally substituted" means an alkyl group as defined below wherein each C atom is bonded to 0, 1, 2 or 3H atoms, as appropriate, and any up to all H atoms may be replaced with a recited substituent, with the proviso that combinations of recited substituents result in a chemically stable compound.

The terms "$(C_1-C_6)$alkyl", "$(C_1-C_4)$alkyl", and "$(C_1-C_3)$alkyl" mean linear or branched saturated carbon groups having from about 1 to about 3, 4, or 6 C atoms respectively. Such groups include but are not limited to methyl, ethyl, n-propyl, isopropyl, n-butyl, isobutyl, sec-butyl, tert-butyl, and the like.

The terms "$(C_1-C_6)$alkoxy" and "$(C_1-C_3)$alkoxy" mean a linear or branched saturated carbon group having from about 1 to about 6 or 3 C atoms, respectively, said carbon group being attached to an O atom. The O atom is the point of attachment of the alkoxy substituent. Such groups include but are not limited to methoxy, ethoxy, n-propoxy, isopropoxy, n-butoxy, isobutoxy, sec-butoxy, tert-butoxy, and the like.

The term "$C_3-C_6$ cycloalkyl" means a saturated monocyclic alkyl group of from 3 to about 8 carbon atoms and includes such groups as cyclopropyl, cyclopentyl, cyclohexyl, and the like.

The term "halo" means an atom selected from Cl, Br, F and I, where Cl, Br and F are preferred and Cl and F are most preferred.

The terms "halo$(C_1-C_6)$alkyl" and "halo$(C_1-C_3)$alkyl" mean a linear or branched saturated carbon group having from about 1 to about 6 or 3 C atoms, respectively, that is substituted with at least 1 and up to perhalo (that is, up to 3 per C atom, as appropriate) Cl or F atoms selected in each instance independently from any other Cl or F atom. Such groups include but are not limited to trifluoromethyl, trichloromethyl, pentafluoroethyl, fluorobutyl, 6-chlorohexyl, and the like.

The terms "halo$(C_1-C_6)$alkoxy" and "halo$(C_1-C_3)$alkoxy" mean a linear or branched saturated carbon group having from about 1 to about 6 or 3 C atoms, respectively, said carbon group being attached to an O atom and being substituted with at least 1 and up to perhalo (that is, up to 3 per C atom, as appropriate) Cl or F atoms selected in each instance independently from any other Cl or F atom. Such groups include but are not limited to trifluoromethoxy, trichloromethoxy, pentafluoroethoxy, fluorobutoxy, 6-chlorohexoxy, and the like.

The term "six membered heterocycle" means an aromatic ring made of 6 atoms, 1, 2, or 3 of which are N atoms, the rest being C, where the heterocycle is attached to the core molecule at any available C atom and is optionally substituted at any available C atom with the recited substituents. Such groups include pyridine, pyrimidine, pyridazine and triazine in all their possible isomeric forms.

The term "five membered heterocycle" means an aromatic ring made of 5 atoms and having 1, 2 or 3 heteroatom(s) each selected independently from O, N, and S, the rest being C atoms, with the proviso that there can be no more than 2O atoms in the heterocycle and when there are 2O atoms they must be nonadjacent. This heterocycle is attached to the core molecule at any available C atom and is optionally substituted at any available C or N atom with the recited substituents. Such groups include pyrrole, furan, thiophene, imidazole, pyrazole, thiazole, oxazole, isoxazole, isothiazole, triazole, oxadiazole, thiadiazole, and tetrazole in all their possible isomeric forms.

The term "fused bicyclic heterocycle" means a group having from 9 to 12 atoms divided into 2 rings that are fused together through adjacent C atoms where 1, 2, or 3 of the remaining atoms are heteroatoms each independently selected from N, O, and S. The heteroatoms may be located at any available position on the fused bicyclic moiety with the proviso that there can be no more than 2O atoms in any fused bicyclic heterocycle, and when 2O atoms are present, they must not be adjacent. At least one of the two fused rings must be aromatic. The other ring, if it were not fused to the aromatic ring, may be aromatic, partially saturated or saturated. An aromatic ring is always attached to the core molecule through any available C atom. The fused bicyclic heterocycle is optionally substituted at any available C atoms with the recited substituents. Such groups include 5-5, 5-6, and 6-6 fused bicycles, where one of the rings is one of the heterocycles described above and the second ring is either benzene or another heterocycle including, but not limited to, chroman, chromene, benzofuran, benzthiophene, quinoline, isoquinoline, phthalazine, naphthyridine, quinoxaline, purine, indole, indazole, isoindole, indolizine, cinnoline, pteridine, isoindole, thienofuran, imidazothiazole, dithianaphthalene, benzoxazine, piperonyl, and the like.

The term "Y is a heterocycle" means a saturated, partially unsaturated or aromatic ring containing about 5 or 6 atoms, 1, 2, or 3 of which are each independently selected from N, O, and S, the rest being C atoms, with the proviso that there can be no more than 2O atoms in any heterocycle. When there are 2O atoms in the heterocycle, they must be nonadjacent. This heterocycle is attached to the core molecule through any available C atom or, except where the heterocycle is pyridyl, through any available N atom. It is optionally substituted with the recited substituents on any available C atom and, except when the heterocycle is pyridyl, on any available N atom. This heterocycle includes furan, pyrrole, imidazole, pyrazole, isoxazole; pyridine, pyrazine, pyrimidine, pyridazine, furazan, pyrrolidine, imidazolidine, imidazoline, pyrazoline, piperidine, morpholine, oxathiazine, oxazine, triazine, piperizine, dioxazole, oxathiole, pyran, dithiole, and the like.

The term "Z is a heterocycle" means a saturated, partially unsaturated or aromatic ring containing about 5 or 6 atoms, 1, 2, or 3 of which are each independently selected from N, O, and S, the rest being C atoms, with the proviso that there can be no more than 2O atoms in any heterocycle. When there are 2O atoms in the heterocycle, they must be nonadjacent. This heterocycle is attached to the core molecule through any available C atom or, except where the heterocycle is pyridyl, through any available N atom. It is optionally substituted with the recited substituents on any available C atom and, except when the heterocycle is pyridyl, on any available N atom. This heterocycle includes furan, pyrrole, imidazole, pyrazole, isoxazole, pyridine, pyrazine, pyrimidine, pyridazine, furazan, pyrrolidine, imidazolidine, imidazoline, pyrazoline, piperidine, morpholine, oxathiazine, oxazine, triazine, piperizine, dioxazole, oxathiole, pyran, dithiole, and the like.

The term "N-oxide" means that for heterocycles containing an otherwise unsubstituted sp$^2$ N atom, the N atom may bear a covalently bound O atom, i.e., —N(—>O). Examples of such N-oxide substituted heterocycles include pyridyl N-oxides, pyrimidinyl N-oxides, pyrazinyl N-oxides and pyrazolyl N-oxides.

The term "piperonyl" means a methylenedioxyphenyl ring of structure

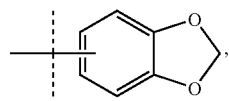

the point of attachment of which is any available aromatic C atom.

Representative compounds of Formula I are disclosed later herein.

The compounds of this invention may contain one or more asymmetric centers, depending upon the location and nature of the various substituents desired. Asymmetric carbon atoms may be present in the (R) or (S) configuration or (R,S) configuration. In certain instances, asymmetry may also be present due to restricted rotation about a given bond, for example, the central bond adjoining two substituted aromatic rings of the specified compounds. Substituents on a ring may also be present in either cis or trans form, and a substituent on a double bond may be present in either Z or E form. It is intended that all such configurations (including enantiomers and diastereomers) are included within the scope of the present invention. Preferred compounds are those with the absolute configuration of the compound of this invention which produces the more desirable biological activity. Separated, pure or partially purified isomers or racemic mixtures of the compounds of this invention are also included within the scope of the present invention.

The use of pharmaceutically acceptable salts of the compounds of this invention are also within the scope of this invention. The term "pharmaceutically acceptable salt" refers to either inorganic or organic acid or base salts of a compound of the present invention that have properties acceptable for the therapeutic use intended. For example, see S. M. Berge, et al. "Pharmaceutical Salts," *J. Pharm. Sci.* 1977, 66, 1-19.

Representative salts of the compounds of this invention include the conventional non-toxic salts and the quaternary ammonium salts that are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate. The term acid addition salts also comprises the hydrates and the solvent addition forms which the compounds of this invention are able to form. Examples of such forms are, for example, hydrates, alcoholates and the like.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates including dimethyl, diethyl, and dibutyl sulfate; and diamyl sulfates, long chain halides such as decyl, lauryl, myristyl and strearyl chlorides, bromides and iodides, aralkyl halides including benzyl and phenethyl bromides, and others.

The esters of appropriate compounds of this invention are pharmaceutically acceptable esters such as alkyl esters, including methyl, ethyl, propyl, isopropyl, butyl, isobutyl or pentyl esters, and the like. Additional esters such as phenyl-($C_1$-$C_5$) alkyl may be used, although methyl ester is preferred.

Unless the context clearly indicates to the contrary, whenever the term "compounds of this invention," "compounds of the present invention", and the like, are used herein, they are intended to include the chemically feasible pharmaceutically acceptable salts and/or esters as well as all stereoisomeric forms of the referenced compounds.

Method of Making the Compounds of the Present Invention

In general, the compounds of this invention may be prepared by standard techniques known in the art, by known processes analogous thereto, and/or by processes disclosed below, using starting materials which are either commercially available, producible according to routine, conventional chemical methods or the synthesis of which is described herein. The particular process to be utilized in the preparation of a compound of this invention depends upon the specific compound desired. Such factors as whether the amine is substituted or not, the selection of the specific substituents possible at various locations on the molecule, and the like, each play a role in the path to be followed. Those factors are readily recognized by one of ordinary skill in the art.

The benzofuran and benzothiophene derivatives of Formula (I) are generally prepared by, but not limited to, the methods outlined below in Reaction Schemes 1 and 2.

In Reaction Scheme 1, the benzofuran or benzothiophene final product of Formula (I) where $R^1$ is H may be synthesized directly by the condensation of a properly substituted 2-cyanophenol (formula (II), where X=O) or 2-cyanothiophenol (formula (II), where X=S) with an appropriate 1-aryl-2-haloethanone of formula (III). The reaction is generally facilitated by a base, such as cesium carbonate, potassium carbonate, sodium carbonate or DBU, in a solvent such as DMF or MeCN, and at temperatures between room temperature to 100° C. to give the final product of formula (I).

Alternatively, when the starting phenol or thiophenol is not readily available, the method outlined in Reaction Scheme 2 may be used, wherein intermediate benzofurans and benzothiophenes of formulas (IV) or (V) are first prepared in analogous manner and then converted to the final product (I) by Suzuki coupling reactions. Thus the halobenzofuran or halobenzothiophene (IV) is either allowed to react with a boronate ester of formula (VI) in the presence of a Pd catalyst and base, or it is converted to the boronate ester of formula (V) then coupled with the halo compound of formula (VII) under similar conditions. Starting materials (II), (III) (VI) and (VII) are generally commercially available or prepared by standard means known in the art and illustrated below in the preparative examples.

Reaction Scheme 1

Synthesis of starting material (II):

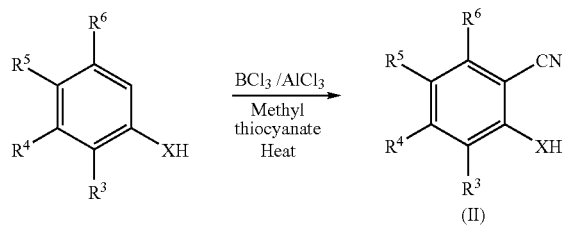

Synthesis of starting material (III):

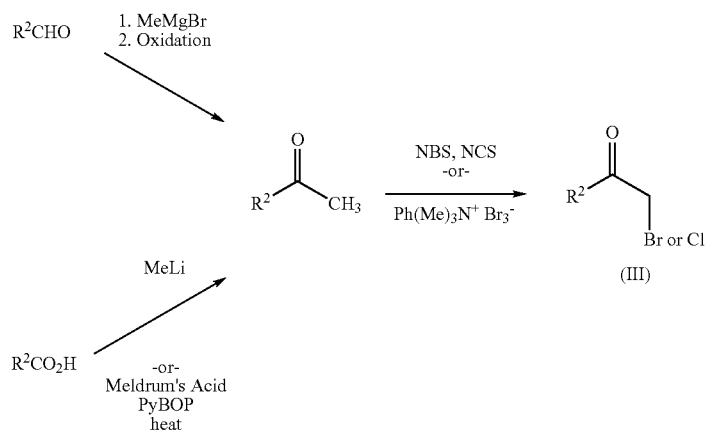

Synthesis of (I) from (II) and (III):

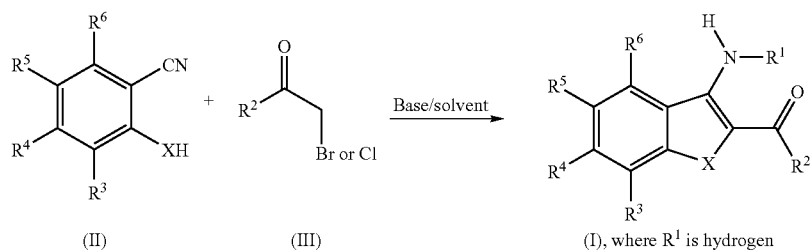

Reaction Scheme 2

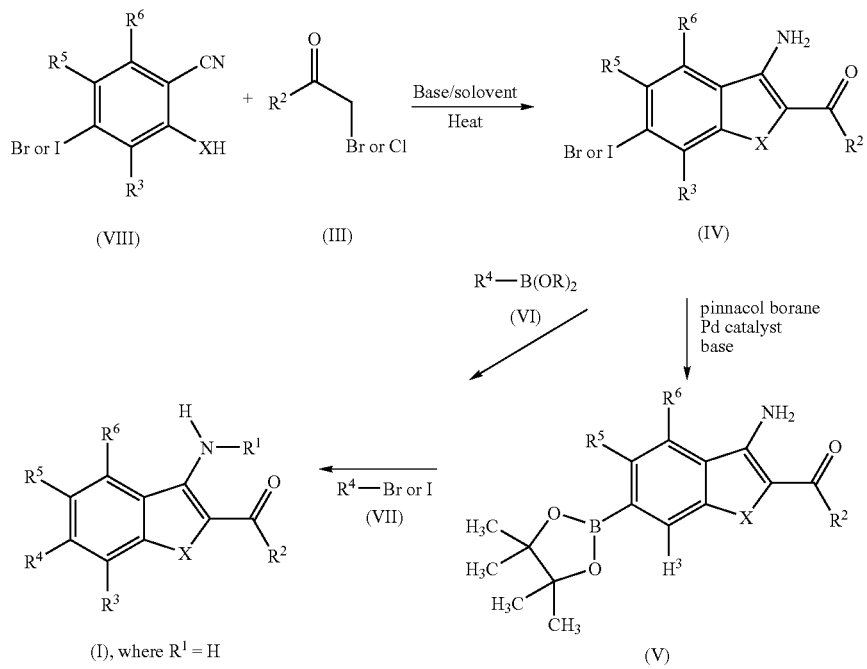

Compounds of formula (I) where $R^1$ is H, prepared by either Reaction Scheme 1 or Reaction Scheme 2 may be converted to other formula (I) compounds where $R^1$ is other than H, as shown in Reaction Scheme 3. For example, treatment with a base and an alkylating agent such as methyl iodide or methyl sulfate provides formula (I) compounds where $R^1$ is alkyl. Similarly, treatment with a base and an acylating agent such as acetyl chloride or benzoyl chloride gives compounds of formula (I) where $R^1$ is acetyl or benzoyl.

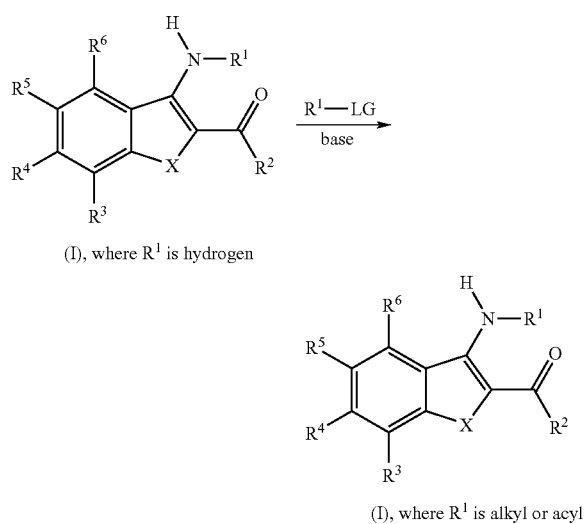

LG = halo, OTs, OMs, OAc etc.

It is to be understood that sensitive or reactive substituents attached to intermediates or to compounds of formula I may need to be protected and deprotected during the preparations described above. Protecting groups in general may be added and removed by conventional methods well known in the art [see, e.g., T. W. Greene and P. G. M. Wuts, *Protective Groups in Organic Synthesis*; Wiley: New York, (1999)].

Variations of the compounds of the invention can be readily prepared using the processes described above and referenced below, or by other standard chemical processes known in the art, by employing appropriate starting materials or intermediate compounds that are readily available and/or are described herein.

Generally, a desired salt of a compound of this invention can be prepared in situ during the final isolation and purification of a compound by means well known in the art. For example, a desired salt can be prepared by separately reacting the purified compound in its free base or free acid form with a suitable organic or inorganic acid, or suitable organic or inorganic base, respectively, and isolating the salt thus formed. In the case of basic compounds, for example, the free base is treated with anhydrous HCl in a suitable solvent such as THF, and the salt isolated as a hydrochloride salt. In the case of acidic compounds, the salts may be obtained, for example, by treatment of the free acid with anhydrous ammonia in a suitable solvent such as ether and subsequent isolation of the ammonium salt. These methods are conventional and would be readily apparent to one skilled in the art.

The compounds of this invention may be esterified by a variety of conventional procedures including reacting the appropriate anhydride, carboxylic acid or acid chloride with the alcohol group of a compound of this invention. The appropriate anhydride is reacted with the alcohol in the presence of a base to facilitate acylation such as 1,8-bis[dimethylamino]naphthalene or N,N-dimethylaminopyridine. Or, an appropriate carboxylic acid can be reacted with the alcohol in the presence of a dehydrating agent such as dicyclohexylcarbodiimide, 1-[3-dimethylaminopropyl]-3-ethylcarbodiimide or other water soluble dehydrating agents which are used to drive the reaction by the removal of water, and, optionally, an acylation catalyst. Esterification can also be effected using the appropriate carboxylic acid in the presence of trifluoroacetic anhydride and, optionally, pyridine, or in the presence of N,N-carbonyldiimidazole with pyridine. Reaction of an acid chloride with the alcohol can be carried out with an acylation catalyst such as 4-DMAP or pyridine.

One skilled in the art would readily know how to successfully carry out these as well as other known methods of esterification of alcohols.

The purification of isomers and the separation of isomeric mixtures of a compound of formula (I) may be accomplished by standard techniques known in the art.

The following examples are provided to further illustrate the compounds of the invention and their preparation, but should not be construed to be limiting in any way.

PREPARATIVE EXAMPLES OF THE INVENTION

Proton (1H) nuclear magnetic resonance (NMR) spectra were measured with a General Electric GN-Omega 300 (300 MHz) spectrometer with either Me$_4$Si ($\delta$ 0.00) or residual protonated solvent (CHCl$_3$ $\delta$ 7.26; MeOH 83.30; DMSO $\delta$ 2.49) as standard. Carbon (13C) NMR spectra were measured with a General Electric GN-Omega 300 (75 MHz) spectrometer with solvent (CDCl$_3$ $\delta$ 77.0; d$_3$-MeOD; $\delta$ 49.0; d$_6$-DMSO $\delta$ 39.5) as standard.

Chiral separations were performed using a commercially available Chiracel® AD HPLC column, eluting with a gradient of isopropanol in hexane (from 1% to 15%) with addition of 0.1% trifluoroacetic acid.

Abbreviations

When the following abbreviations are used herein, they have the following meaning:

| | |
|---|---|
| ADDP | 1,1'-(azodicarbonyl)-dipiperidine |
| DBU | 1,8-Diazabicyclo [5.4.0]undec-7-ene |
| DMF | N,N-dimethylformamide |
| DMSO | Dimethylsulfoxide |
| EA | Elemental analysis |
| ES | Electrospray |
| Et | Ethyl |
| Et$_2$O | Diethyl ether |
| EtOAc | Ethyl acetate |
| GC-MS | Gas chromatography-mass spectroscopy |
| HEX | Hexanes |
| LC-MS | Liquid Chromatography/Mass Spectroscopy |
| Me | Methyl |
| MeCN | Acetonitrile |
| MeOH | Methanol |
| MPLC | Medium Pressure Liquid Chromatograph |
| NCS | N-chlorosuccinimide |
| NMR | Nuclear Magnetic Resonance Spectroscopy |
| Pd(dppf)$_2$Cl$_2$ | [1,1'-bis(diphenylphosphino)-ferrocene]dichloropalladium(II) |
| Ph | Phenyl |
| PyBOP | Benzotriazole-1-yl-oxy-tris-pyrrolidino-phosphonium hexafluorophosphate |
| RT | Retention time (HPLC) |
| R$_f$ | TLC Retention Factor |
| rt | Room temperature |
| THF | Tetrahydrofuran |
| TLC | Thin layer chromatography |

Preparation of Starting Materials and Intermediates
General Method A: 2-Halo-1-Arylketones (III)

Compounds of formula (III) are either commercially available or may be prepared as shown in the Reaction Scheme for General Method A, and as described in one or more of the Examples below.

Reaction Scheme for General Method A

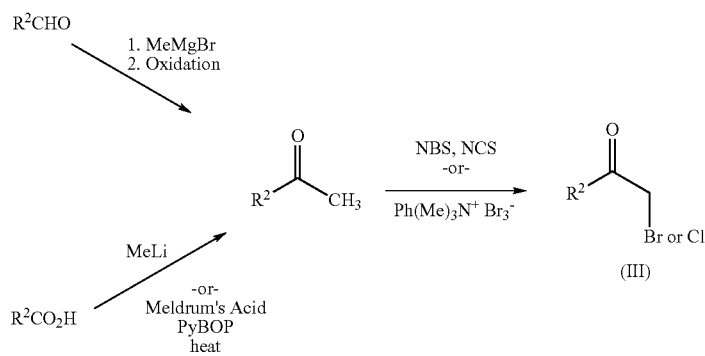

Example 1

Method A-1

Preparation
2-bromo-1-(2,4,6-trichlorophenyl)ethanone

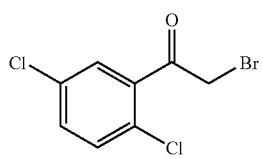

A mixture of 1,3,5-trichlorobenzene (10.0 g, 55.1 mmol), 2-bromoacetyl bromide (5.0 mL, 57.8 mmol, 1.05 eq), and aluminum chloride (7.7 g, 57.8 mmol, 1.05 eq) was heated neat at 80° C. under argon for 17 h until a black precipitate is formed. The reaction was cooled to room temperature, and the resultant black mass was dissolved in ethyl acetate (500 mL). Water (200 mL) was added slowly at 0° C. to quench the reaction, and the biphasic layers were separated. The organic layer was then washed with water (2×150 mL) and brine (1×150 mL), dried (MgSO₄), filtered, and evaporated in vacuo. Recrystallization from hexane gave 11.5 g (69.3%) of 2-bromo-1-(2,4,6-trichlorophenyl)-ethanone as a fluffy white solid. ¹H-NMR (DMSO-d₆) δ 7.86 (s, 2H), 4.78 (s, 2H); $R_f$=0.28, 2% ethyl acetate-hexane.

Example 2

Method A-2a

Preparation of 2-bromo-1-(2,5-dichlorophenyl)ethanone

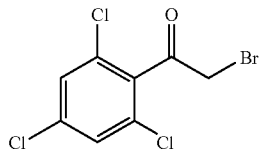

To 2,5-dichloroacetophenone (5.0 g, 26.45 mmol) in anhydrous tetrahydrofuran (53 mL) under argon was added phenyltrimethylammonium tribromide (9.94 g, 26.45 mmol, 1.0 eq) at 0° C. The reaction mixture was stirred at ambient temperature for 16 h, concentrated, and re-dissolved in ethyl acetate. The organic layer was washed with water (2×250 mL) and brine (1×150 mL), dried (MgSO₄), filtered, and evaporated in vacuo. Purification using MPLC chromatography (Biotage) gave 3.47 g (52.5%) of 2-bromo-1-(2,5-dichlorophenyl)ethanone as a clear oil. ¹H-NMR (DMSO-d₆) δ 7.93 (dd, J=2.1 Hz, 0.9 Hz, 1H), 7.61 to 7.60 (m, 2H), 4.86 (s, 2H).

Example 3

Method A-2b

Preparation of 2-Bromo-1-(2-bromo-4-fluoro-phenyl)-ethanone

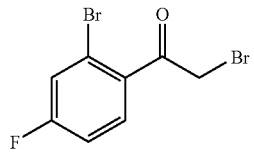

This compound was prepared from 1-(2-bromo-4-fluorophenyl)-ethanone (2.5 g, 11.52 mmol) in the manner described for 2-bromo-1-(2,5-dichlorophenyl)-ethanone (Example A-2), affording 2.14 g (63%) of 2-bromo-1-(2-bromo-4-fluoro-phenyl)-ethanone as a clear oil. ¹H-NMR (CD₂Cl₂) δ 7.57 (dd, J=9.6 Hz, 1H), 7.44 (dd, J=8, 2 Hz, 1H), 7.21 (m, 7.21-7.14, 1H), 4.51 (s, 2H); TLC $R_f$=0.38, 15% ethyl acetate-hexanes.

Example 4

Method A-3

Preparation of 2-Chloro-1-(4-methyl-3-pyridinyl)ethanone hydrochloride

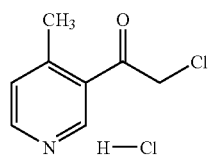

Step 1: Preparation of 1-(4-methyl-3-pyridinyl)ethanone

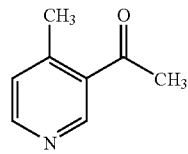

A solution of 3-acetylpyridine (100 g, 0.82 mol), dimethyl sulfide (400 mL, 5.4 mol) and copper (I) iodide (7.94 g, 0.041 mol) in anhydrous THF (2 L) was stirred at room temperature under an argon atmosphere. Phenyl chloroformate (0.4 mL, 0.82 mol) was then added, producing a dark brown precipitate. After 30 min, the mixture was cooled below −21° C. and methyl magnesium bromide (1.4 M in 3:1 toluene-THF, 586 mL, 0.82 mol) was added over 50 min, keeping the reaction temperature below −15° C. The color lightened as the mixture became a solution; a lime green precipitate formed near the end of the addition, but re-dissolved upon completion. The mixture was stirred and allowed to warm slowly; after 2 h it had warmed to 8.8° C. Saturated aqueous ammonium chloride solution (500 mL) was added; after stirring 10 min, the mixture was poured into a separatory funnel with water (500 mL). The organic phase was separated, washed with brine (500 mL), dried (Na₂SO₄), filtered and then concentrated in vacuo. The residue was purified by silica gel chromatography using a hexane-EtOAc gradient to afford 134.3 g (63.7%) of the intermediate dihydropyridine.

A solution of the intermediate dihydropyridine (0.52 mol) in dichloromethane (100 mL) was added to a stirred suspension of sulfur (16.67 g, 0.52 mol) in decalin and slowly heated to reflux under an argon sweep. After refluxing 1 h, the mixture was allowed to cool to room temperature, then filtered through a pad of silica gel. After eluting the decalin with hexane, elution with a hexane-diethyl ether gradient afforded 49.4 g (70.3%) the desired 1-(4-methyl-3-pyridinyl)ethanone as a reddish-brown oil: TLC $R_f$ 0.19 (diethyl ether); TLC $R_f$ 0.14 (1:1 hexane-EtOAc); $^1$H NMR (CD$_2$Cl$_2$) δ 8.9 (s, 1H), 8.5 (d, 1H), 7.2 (dd, 1H), 2.6 (s, 3H), 2.51 (s, 3H); GC MS 135 (M$^+$).

Step 2: Preparation of 2-chloro-1-(4-methyl-3-pyridinyl)ethanone hydrochloride

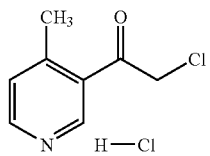

In a 500 mL round bottom flask was placed 1-(4-methyl-3-pyridinyl)ethanone (10.0 g, 74.1 mmol) in 90 mL of Et$_2$O. To this solution was added 88.9 mL of 1M HCl/Et$_2$O (1.2 eq, 88.9 mmol) with stirring and the solution allowed to stir for 1 h at room temperature, at which point, the precipitate was filtered and washed with Et$_2$O. The solid was then dried in vacuo at about 60° C. This HCl salt (12 g, 70.0 mmol) was then dissolved in 70.0 mL of 1M HCl/acetic acid where 9.34 g (1 eq, 70.0 mmol) of N-chlorosuccinimide (NCS) was added and the reaction allowed to stir under Argon at room temperature overnight. At this point, 300 mL of Et$_2$O was added resulting in an off-white precipitate. This was allowed to stir for 1 h at which point the solid was filtered and rinsed with Et$_2$O to provide 12.0 g (83%) of the desired 2-chloro-1-(4-methyl-3-pyridinyl)ethanone hydrochloride. GC/MS RT=6.60 min; $^1$H-NMR (DMSO-d$_6$) δ 2.51 (s, 3H), 5.15 (s, 2H), 7.68 (d, 1H), 8.68 (d, 1H), 9.06 (s, 1H); [M]$^+$ 169 (95%).

Example 5

Method A-4

Preparation of 2-chloro-1-[4-(trifluoromethyl)-3-pyridinyl]ethanone hydrochloride

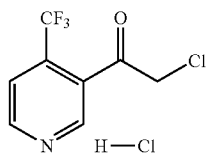

Step 1

In a 250 mL round bottom flask was placed 3.0 g of 4-trifluoronicotinic acid (15.7 mmol, 1 eq) in 100 mL of THF. To this was added 5.3 mL (3.8 g, 37.7 mmol, 2.4 eq) of triethylamine and 9.8 g (18.8 mmol, 1.2 eq) of PyBOP. This was allowed to stir for 10 min at room temperature where 2.7 g of Meldrum's acid (18.8 mmol, 1.2 eq) was added and the reaction allowed to stir at room temperature overnight (18 h).

At this point, 30 mL of 1M HCl (aq) was added and the reaction turned immediately from orange to purple. This was then heated at for 18 h gradually turning from purple to yellow.

The reaction was then basified with saturated NaHCO$_3$ and extracted with EtOAc (3×200 mL). The combined organics were dried, filtered, and evaporated. The residue was purified via BIOTAGE (35% EtOAc/Hex) to provide methyl 4-trifluoromethylnicotinate 1.84 g (62%) of the desired product as a colorless oil. TLC R$_f$=0.57 (50% EtOAc:Hex).

Step 2

In a 100 mL flask was placed 1.84 g (9.7 mmol, 1 eq) of methyl 4-trifluoromethylnicotinate in 25 mL of 1 M HCl in CH$_3$COOH. To this was then added 1.3 g of NCS (9.7 mmol, 1 eq) and the reaction allowed to stir overnight (18 h).

The mixture was then transferred to a 500 mL Erlenmeyer flask and to this was added 300 mL of 2 M HCl in Et$_2$O with stirring. This resulted in a white precipitate which was then filtered to provide 1.2 g (49%) of the desired 2-chloro-1-[4-(trifluoromethyl)-3-pyridinyl]ethanone hydrochloride as a white solid. $^1$H-NMR (DMSO-d$_6$) δ 9.21 (s, 1H), 9.02 (d, 1H), 7.94 (d, 1H), 5.19 (s, 2H).

Example 6

Method A-5

Preparation of 1-Benzo[1,3]-dioxol-4-yl-2-bromo-ethanone

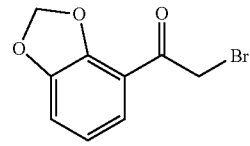

Step 1: Preparation of starting material 1-Benzo[1,3]-dioxol-4-yl-ethanone

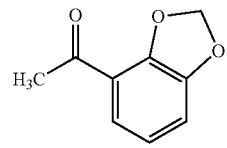

To a solution of MeMgBr in THF (1 M, 50 mL, 50 mmol, 1.5 eq) was diluted with 50 mL THF and cooled to –10 C. A solution of benzo[1,3]dioxole-4-carboxaldehyde (5.0 g, 33.3 mmol) in 50 mL THF was slowly added, and the reaction left to stir for 1 h. The reaction mixture was then quenched by pouring into 500 mL of ice cold sat. ammonium chloride and the mixture extracted with ether. The organic layers were dried over sodium sulfate and filtered through a plug of silica gel before concentrating in vacuo, providing 4.9 g of a white solid. A mixture of this solid (2.0 g, 12.0 mmol) and MnO$_2$ (10.5 g, 120.4 mmol, 10.0 eq) in 75 mL diethyl ether was stirred vigorously for 48 h. The reaction mixture was then filtered first through a plug of silica gel, then through a 0.46 μm frit before concentrating in vacuo to provide 2.1 g of an off-white solid. Purification by MPLC (Biotage) using a hexane-ethyl acetate gradient provided 1.47 g (74%) of 1-benzo[1,3]dioxol-4-yl-ethanone as an off-white solid. $^1$H-NMR (CDCl$_3$) δ 7.35 (d, J=8 Hz, 1H), 6.97 (dm, J=8 Hz, 1H), 6.87 (dd, J=8 Hz, 1H), 6.08 (s, 2H), 2.59 (s, 3H); TLC R$_f$=0.18, 25% ethyl acetate-hexanes.

Step 2: Preparation of Intermediate
1-Benzo[1,3]-dioxol-4-yl-2-bromo-ethanone

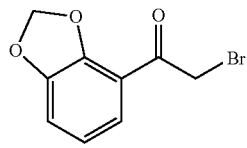

This compound was prepared from 1-benzo[1,3]dioxol-4-yl-ethanone (2.15 g, 13.1 mmol) in the manner described for 2-bromo-1-(2,5-dichlorophenyl)ethanone (Example I-2), affording 1.54 g (48%) of 1-benzo[1,3]dioxol-4-yl-2-bromo-ethanone as an off-white solid. $^1$H-NMR (CD$_2$Cl$_2$) δ; 7.41 (dd, J=8.1 Hz, 1H), 7.05 (dd, J=8.1 Hz, 1H), 6.94 (dd, J=8.8 Hz, 1H), 6.13 (s, 2H), 4.55 (s, 2H). TLC R$_f$=0.28, 15%, ethyl acetate-hexanes.

Example 7

Method A-6

Preparation of starting material 2-bromo-1-[3-(tert-butyl-diphenyl-silanyloxy)-phenyl]ethanone

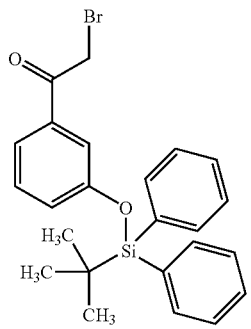

Step 1: Preparation of 1-[3-(tert-butyl-diphenylsilanyloxy)phenyl]ethanone

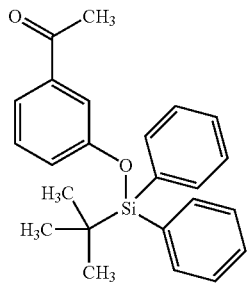

To 1-(3-hydroxy-phenyl)ethanone (3.3 g, 24.2 mmol) and tert-butylchlorodiphenyl-silane (7.3 g, 26.7 mmol, 1.1 eq) in anhydrous dichloromethane (50 mL) at 0° C. was added dimethylaminopyridine (296 mg, 2.42 mmol, 0.1 eq) and triethylamine (2.69 g, 26.7 mmol, 1.1 eq), and the reaction mixture was stirred at room temperature under argon for 16 h. The reaction mixture was diluted with ethyl acetate and water. The organic layer was washed with water, brine, and dried over magnesium sulfate. The solvent was evaporated under reduced pressure to afford 8.7 g (95.8%) of crude product. $^1$H-NMR (Acetone-d$_6$) δ 7.78 (m, 5H), 7.56 to 7.38 (m, 7H), 7.22 (m, 1H), 7.00 (m, 1H), 2.38 (s, 3H), 1.12 (s, 9H); MS ES (MH$^+$=375); R$_f$=0.90 (30% ethyl acetate-hexane).

Step 2: Preparation of: 2-bromo-1-[3-(tert-butyl-diphenyl-silanyloxy)phenyl]ethanone

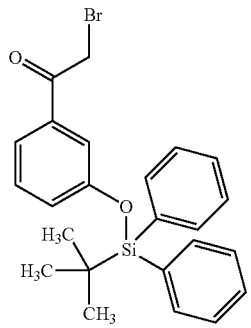

This compound was prepared from 1-[3-(tert-butyl-diphenyl-silanyloxy)phenyl]-ethanone (8.7 g, 23.23 mmol) in the manner described for 2-bromo-1-(2,5-dichlorophenyl)ethanone, affording 10.2 g (96.8%) of a clear oil. $^1$H-NMR (Acetone-d$_6$) δ 7.78 (m, 4H), 7.60 (m, 1H), 7.50 to 7.40 (m, 7H), 7.22 (m, 1H), 7.05 (m, 1H), 4.56 (s, 2H), 1.13 (s, 9H); R$_f$=0.92 (30% ethyl acetate-hexane).

This material was used as the protected form in the synthesis of Example 104; desilylation occurred during the benzofuran forming step.

General Method H: Preparation of Intermediates (VI) and (VII)

The aryl halides (VII), the arylboronic acids, or the arylboronates (VI) used to prepare compounds in this invention of formula (I) (see Methods B, C, D, and G below) were either commercially available or prepared by one or more methods described in Examples below. Arylhalides (VII), prepared by the methods described hereafter, may subsequently be used either directly as starting materials for General Methods B, C-1, D-1, and D-3 described below, or converted to the corresponding boronates of formula (VI) using procedures described in step 1 of Examples C-2 and D-2 and used as described in General Method Example 8

Method H-1

Preparation of
1-Bromo-3-methylsulfanylmethyl-benzene

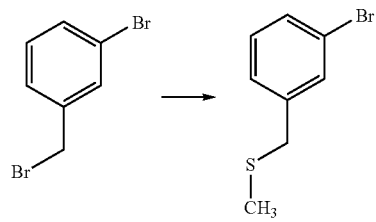

Sodium thiomethoxide (0.616 g, 8.8 mmol) was added to DMF (8 mL) and cooled to 0° C. To this solution was added 1-bromo-3-bromomethyl-benzene (2 g, 8 mmol). The mixture was allowed to warm to rt and stir for 18 h. The mixture was then poured into cold water (50 mL) and extracted with EtOAc (3×20 mL). The organics were combined and dried with sodium sulfate. The solution was concentrated in vacuo to yield the crude product, which was then purified via flash chromatography (5% ethyl acetate-hexanes) to yield 1.3 g (68.5%) of 1-bromo-3-methylsulfanylmethyl-benzene as a pure product. 1H-NMR (methylene chloride-d2) δ 7.48-7.47 (m, 1H), 7.392 (dt, J=7.9, 1.5 Hz, 1H), 7.28-7.207 (m, 2H), 3.64 (s, 2H), 1.99 (s, 3H); LC-MS RT: 3.70, [M+H]+: 354.1.

Example 9

Method H-2

Preparation of Alkyl aryl thioethers

Preparation of 1-Bromo-3-isopropylsulfanyl-benzene

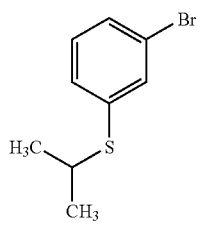

3-Bromobenzenethiol (1 g, 5.3 mmol) was added to acetone (25 mL). Next was added potassium carbonate (1.46 g, 10.58 mmol) and 2-iodopropane (1.17 g, 6.88 mmol). This was refluxed for 5 h. Reaction was then cooled to rt and filtered through a pad of Celite. The organic was then concentrated in vacuo and taken up in ether at which time a white precipitate crashed out. The organic was then re-filtered through the same celite plug and concentrated in vacuo to provide 1.14 g (93.17%) of 1-bromo-3-isopropylsulfanyl-benzene as an oil. ¹H-NMR (methylene chloride-d2) δ 7.54 (s, 1H), 7.37-7.31 (m, 2H), 7.18 (t, J=7.9 Hz, 1H), 3.50-3.36 (m, 1H), 1.31 (d, J=6.1 Hz, 6H); LC-MS RT: 4.15, [M+H]+: 233.2.

Example 10

Method H-3

Preparation of 1-Bromo-3-methylsulfonyl-benzene

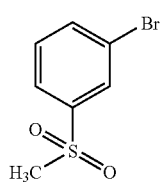

Step 1: Preparation of 1-Bromo-3-methanesulfinyl-benzene

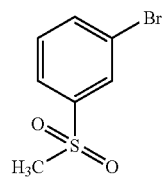

3-Bromothioanisol (0.5 g, 2.46 mmol) was added to methylene chloride (12 mL) and chilled to 0° C. To this was added 3-chloroperoxybenzoic acid (0.467 g, 2.71 mmol). The m-CPBA did not dissolve completely. The mixture was stirred overnight. The reaction was quenched with a saturated sodium thiosulfate (30 mL) solution. The product was extracted with EtOAc (3×20 mL). The organic fractions were combined, washed with brine (20 mL), and dried with sodium sulfate. The organic was then concentrated to yield 0.912 g (81%) 1-bromo-3-methanesulfinyl-benzene. ¹HNMR (methylene chloride-d₂) δ 7.83 (t, J=2.0 Hz, 1H), 7.66 (d, J=7.6 Hz, 1H), 7.57 (d, J=8.3 Hz, 1H), 7.44 (t, J=1.9 Hz, 1H), 2.77 (s, 3H); LC-MS RT: 1.28, [M+H]+: 219.0.

Step 2: Preparation of 1-Bromo-3-methanesulfonyl-benzene

3-Bromothioanisol (8.7 g, 43 mmol) was added to methylene chloride (125 mL) chilled to 0° C. To this was added 3-chloroperoxybenzoic acid (22.2 g, 129 mmol). The m-CPBA did not dissolve completely. The mixture was stirred overnight. The reaction was quenched with a saturated sodium thiosulfate (150 mL) solution. The product was extracted with EtOAc (3×100 mL). The organic fractions were combined, washed with brine (75 mL), and dried with sodium sulfate. The organic was then concentrated to yield 9.89 g (97%) 1-bromo-3-methanesulfonyl-benzene. ¹HNMR (methylene chloride-d$_2$) δ 8.09 (s, 1H), 7.85 (dd, J=19.2, 7.8 Hz, 2H), 7.50 (t, J=8.2 Hz, 1H), 3.06 (s, 3H); GC-MS RT: 6.49, [M+H]$^+$: 236.0.

Example 11

Method H-4

Preparation of N-(3-Iodo-benzyl)-methanesulfonamide

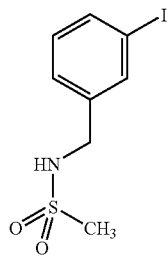

A mixture of 3-iodobenzylamine (1.0 g, 4.29 mmol) and methanesulfonyl chloride (0.35 mL, 4.51 mmol, 1.05 eq) in anhydrous pyridine (2.1 mL) was stirred at 50° C. under argon for 3 days. The cooled reaction was quenched with 1N HCl and diluted with ethyl acetate. The ethyl acetate layer was washed with water, brine, and dried over sodium sulfate. The solvent was removed at reduced pressure, and the crude product was purified on the MPLC (Biotage) eluted with 25% ethyl acetate-hexane. Crystallization from dichloromethane-ether-hexane afforded 1.307 g (97.9%) of the product. $^1$H-NMR (DMSO-d$_6$) δ 7.68 (s, 1H), 7.60 (ddd, J=7.8 Hz, 1.8 Hz, 1.2 Hz, 1H), 7.55 (t, J=6.3 Hz, 1H), 7.32 (d, J=9.0 Hz, 1H), 7.80 (t, J=7.8 Hz, 1H), 4.09 (d, J=6.6 Hz, 2H), 2.85 (d, J=1.8 Hz, 3H); LC-MS (ES MH$^+$=264, RT=2.39 min); R$_f$=0.48 (50% ethyl acetate-hexane).

Example 12

Method H-5

Preparation of 1-(3-Iodo-phenyl)-3-methyl-urea

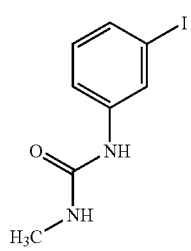

A mixture of 3-iodoaniline (1.0 g, 4.57 mmol) and methylisocyanate (0.29 mL, 5.02 mmol, 1.1 eq) in anhydrous N,N-dimethylformamide (3.0 mL) was stirred at 100° C. under argon for 16 h. The reaction was diluted with ethyl acetate and washed with water, brine, and dried over sodium sulfate. The solvent was removed at reduced pressure, and the crude oil was crystallized from ether-hexane to afford 732.5 mg (58.1%) of the product. $^1$H-NMR (DMSO-d$_6$) δ 8.60 (s, 1H), 7.93 (t, J=1.8 Hz, 1H), 7.25 (ddd, J=8.1 Hz, 2.1 Hz, 0.9 Hz, 1H), 7.20 (ddd, J=8.1 Hz, 2.1 Hz, 0.9 Hz, 1H), 6.98 (t, J=8.1 Hz, 1H), 6.04 (broad d, J=4.8 Hz, 1H), 2.60 (d, J=5.4 Hz, 3H); R$_f$=0.23 (50% ethyl acetate-hexane).

Example 13

Method H-6

Preparation of (R)-3-(3-Bromo-phenoxy)-propane-1,2-dioll

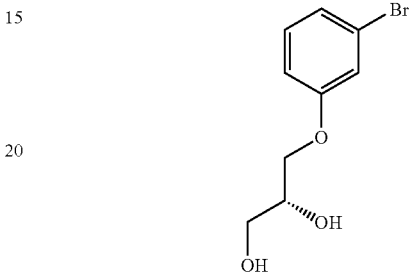

To 3-bromophenol (1.0 g, 5.78 mmol) and (R)-(+)-glycidol (428 mg, 5.78 mmol, 1.0 eq) in ethanol (50 mL) was added triethylamine (29 mg, 0.29 mmol, 0.05 eq), and the reaction mixture was refluxed under argon for 3 h. The reaction mixture was cooled and poured into ethyl acetate and water. The organic layer was washed with water, brine, and dried over sodium sulfate. The solvent was removed at reduced pressure, and the crude product was purified on the MPLC (Biotage) eluted with 30% ethyl acetate-hexane to give the diol as a white solid (1.20 g, 84.0%). $^1$H-NMR (Acetone-d$_6$) δ 7.23 (t, J=8.4 Hz, 1H), 7.11 (m, 2H), 6.95 (m, 1H), 4.12 (m, 2H), 3.98 (m, 2H), 3.80 (m, 1H), 3.65 (m, 2H); R$_f$=0.12 (30% ethyl acetate-hexane).

Example 14

Method H-7

Preparation of 2-fluoro-3-iodo-pyridine

To a solution of n-butyllithium in hexanes (40.14 mL, 1.6 M) under argon at −78° C. was added diisopropylamine (6.5 g, 64.2 mmol, 1.0 eq). After stirring for 30 min at −78° C., a solution of 2-fluoropyridine (6.23 g, 64.2 mmol, 1.0 eq) in anhydrous THF (50 mL) was added. The reaction mixture was stirred at −78° C. for 4 h. Iodine (16.3 g, 64.2 mmol, 1.0 eq) was then added, and the reaction mixture was stirred at −78° C. for another 30 min. The reaction was hydrolyzed with 10% water-THF, and diluted within ethyl acetate and water. The organic layer was washed with water, brine, and dried. The solvent was evaporated under reduced pressure, and the crude product was purified on a MPLC (Biotage) eluted with 20/8020 v/v ethyl acetate-hexane to give 2-fluoro-3-iodo-pyridine as a yellow oil (8.50 g, 59.4%). $^1$H-NMR (Acetone-d$_5$) δ 8.14 (m, 2H), 6.94 (m, 1H); GC-MS (M$^+$=223, RT=9.50 min); R$_f$=0.70 (30% ethyl acetate-hexane).

Example 15

Method H-8

Preparation of 3-iodo-2-methoxy-pyridine

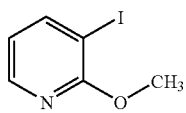

To a solution of sodium methoxide (8.0 mL, 35.9 mmol, 4.0 eq, 25% in methanol) in methanol (60 mL) was added 2-fluoro-3-iodo-pyridine (2.0 g, 8.97 mmol). The reaction mixture was refluxed under argon for 1 h. The reaction mixture was diluted with ethyl acetate and water. The organic layer was washed with water, brine, and dried over sodium sulfate. The solvent was removed at reduced pressure to give 1.8 g (85.4%) of crude product as a yellow oil. $^1$H-NMR (Acetone-d$_6$) 8.16 (m, 2H), 6.78 (m, 1H), 3.93 (s, 3H); LC-MS (ES MH$^+$=236.2); R$_f$=0.75 (30% ethyl acetate-hexane).

Example 16

Method H-9

Preparation of (3-iodo-pyridin-2-yl)-methylamine

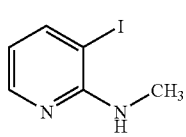

To a solution of 40% methylamine in water (60 mL) was added 2-fluoro-3-iodo-pyridine (2.0 g, 8.97 mmol), and the reaction mixture was refluxed under argon for 4 h. The cooled reaction was diluted with ethyl acetate and water. The organic layer was washed with water, brine, and dried. The solvent was evaporated under reduced pressure to give 1.70 g (81.0%) of crude product. $^1$H-NMR (Acetone-d$_6$) δ 8.06 (dd, J=4.8, 1.5 Hz, 1H), 7.89 (dd, J=7.2, 1.8 Hz, 1H), 6.34 (m, 1H), 5.60 (broad, s, 1H), 2.94 (d, J=4.5 Hz, 3H); R$_f$=0.68 (30% ethyl acetate-hexane).

Example 17

Method H-10

Preparation of cyclopropanecarboxylic acid (3-bromophenyl)amide

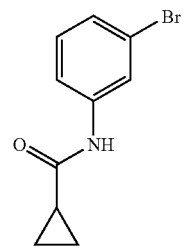

A mixture of 3-bromoaniline (1.0 g, 5.81 mmol), cyclopropane carbonyl chloride (0.61 g, 5.81 mmol, 1.0 eq), and triethylamine (1.17 g, 11.6 mmol, 2.0 eq) in anhydrous THF (20 mL) was stirred at room temperature under argon for 16 h. The reaction mixture was diluted with ethyl acetate and water. The organic layer was washed with water, brine, and dried over magnesium sulfate. The solvent was removed at reduced pressure to afford 1.05 g (75.2%) of the crude product. $^1$H-NMR (Acetone-d$_6$) δ 8.60 (broad s, 1H), 8.07 (dd, J=3.6, 2.1 Hz, 1H), 7.52 (m, 1H), 7.22 (m, 2H), 1.73 (m 1H), 0.90 (m, 2H), 0.80 (m, 2H); MS ES (MH$^+$=242); R$_f$=0.46 (30% ethyl acetate-hexane).

Example 18

Method H-11

Preparation of 3-Bromo-N-(2-methoxy-ethyl)-benzenesulfonamide

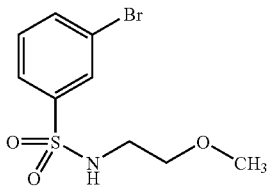

A solution of 3-bromobenzenesulfonyl chloride (1.0 g, 3.72 mmol), 2-methoxyethylamine (0.84 g, 11.15 mmol, 3.0 eq), potassium carbonate (2.57 g, 18.59 mmol, 5.0 eq) in acetone (10.0 mL) was stirred at 40° C. for 4 h. The reaction was diluted with ethyl acetate, washed with water, brine, and dried over magnesium sulfate. The solvent was removed at reduced pressure and purified on the MPLC (Biotage) eluted with 20-25% ethyl acetate-hexane to afford 1.05 g (96%) of the product. R$_f$=0.33 (silica, ethyl acetate:hexanes, 3:7);

$^1$H-NMR (DMSO-d$_6$) δ 7.94 to 7.76 (m, 4H), 7.54 (t, J=7.9 Hz, 1H), 3.27 (t, J=5.6 Hz, 2H), 3.13 (s, 3H), 2.93 (q, J=5.6 Hz, 2H).

Example 19

Method H-12

Preparation of diethyl-(3-iodo-benzyl)-amine

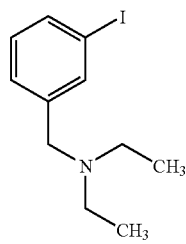

A solution of 3-bromophenacyl bromide (1.0 g, 3.20 mmol), diethylamine (0.70 g, 9.60 mmol, 3.0 eq), potassium carbonate (1.33 g, 9.60 mmol, 3.0 eq) in acetone (10.0 mL) was stirred at 40° C. for 4 h. The reaction was diluted with ethyl acetate, washed with water, brine, and dried over magnesium sulfate. The solvent was removed at reduced pressure and purified on the MPLC (Biotage) eluted with 5-8% ethyl acetate-hexane to afford 0.92 g (99%) of the product. R$_f$=0.28 (silica, ethyl acetate:hexanes, 1:9); $^1$H-NMR (DMSO-d$_6$) δ 7.66 (bs, 1H), 7.59 to 7.55 (m, 1H), 7.33 to 7.29 (m, 1H), 7.10 (t, J=7.8 Hz, 1H), 3.47 (s, 2H), 2.42 (q, J=7.1 Hz, 4H), 0.95 (t, J=6.9, 6H).

Example 20

Method H-13

Preparation of 3-bromo-N-methyl-benzamide

A suspension of methylamine hydrochloride (0.9 g, 13.40 mmol, 3.0 eq) and triethyl amine (2.26 g, 22.33 mmol, 5.0 eq) in anhydrous methylene chloride (10 mL) was cooled to 0° C. The cooled suspension was treated with 3-bromobenzoyl chloride (1.0 g, 4.47 mmol) and then allowed to stir at room temperature for 4 h. The reaction was diluted with ethyl acetate, washed with water, brine, and dried over magnesium sulfate. The solvent was removed at reduced pressure and purified on the MPLC (Biotage) eluted with 35-45% ethyl acetate-hexane to afford 0.60 g (63%) of the product. R$_f$=0.28 (silica, ethyl acetate:hexanes, 2:3); $^1$H-NMR (DMSO-d$_6$) δ 8.55 (bs, 1H), 7.99 (t, J=1.7 Hz, 1H), 7.83 to 7.79 (m, 1H), 7.73 to 7.69 (m, 1H), 7.42 (t, J=8.0 Hz, 1H), 2.77 (d, J=6.7 Hz, 3H).

Example 21

Method H-14

Preparation of 2-(3-bromo-phenyl)-acetamide

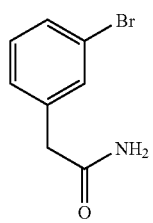

A solution of 3-bromophenylacetonitrile (1.0 g, 5.10 mmol) in acetone (25 mL) and water (15 mL) was treated with sodium percarbonate. The reaction was stirred at 60° C. overnight. The organic solvent was removed at reduced pressure and the residue was diluted with ethyl acetate and water. The layers were separated and the organic was washed with brine and dried over magnesium sulfate. The solvent was removed at reduced pressure and the residue was washed with diethyl ether-hexanes (1/1, v/v) to afford 0.65 g of product (60%) as a white solid. R$_f$=0.18 (silica, ethyl acetate:hexanes, 3:2); $^1$H-NMR (DMSO-d$_6$) δ 7.50 (bs, 1H), 7.46 to 7.39 (m, 2H), 7.26 to 7.22 (m, 2H), 6.93 (bs, 1H), 3.37 (s, 2H).

Example 22

Method H-15

Preparation of 2-(3-Bromo-phenyl)-propan-2-ol

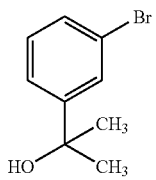

A solution of 3N methylmagnesium bromide (6.53 mL, 19.59 mmol, 3 eq) in diethyl ether was cooled to 0° C. and treated with 3-bromoacetophenone (1.3 g, 6.53 mmol). The reaction was stirred at room temperature for 4 h. The reaction was diluted with ethyl acetate and water. The layers were separated and the organic was washed with saturated sodium bicarbonate, 2N HCl, brine and dried over magnesium sulfate. The solvent was removed at reduced pressure and purified on the MPLC (Biotage) eluted with 5-10% ethyl acetate-hexane to afford 1.2 g (90%) of the product. R$_f$=0.22 (silica, ethyl acetate:hexanes, 1:9); $^1$H-NMR (DMSO-d$_6$) δ 7.63 (t, J=1.8 Hz, 1H), 7.45 to 7.35 (m, 2H), 7.25 (t, J=7.7, 1H), 5.15 (s, 1H), 1.39 (s, 6H).

General Method B: Preparation of Cyanophenols, Cyanothiophenols and Conversion to Formula (I) Compounds In these methods, cyanophenols or thiophenols (II) are prepared from readily available phenols or thiophenols, then coupled with (III) to provide the products of formula (I) as shown in the Reaction Scheme for General Method B, and in the specific examples below for this method where X=O

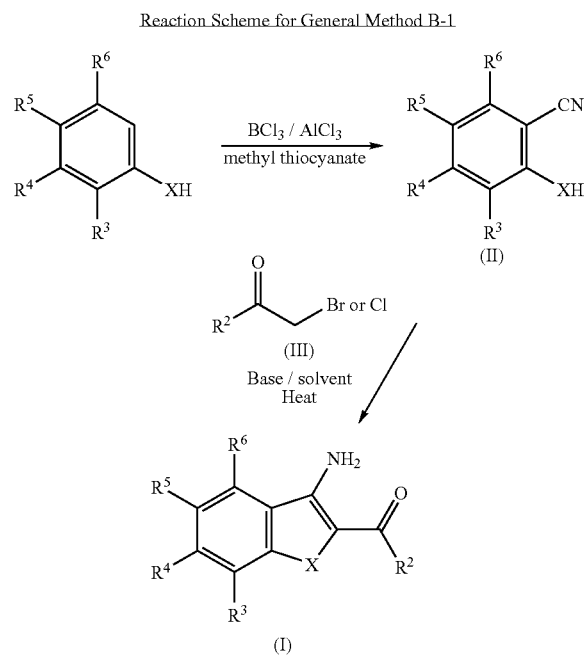

Example 23

Method B-1

Preparation of 3-amino-6-phenyl-1-benzofuran-2-yl)(2,4-dichlorophenyl)methanone

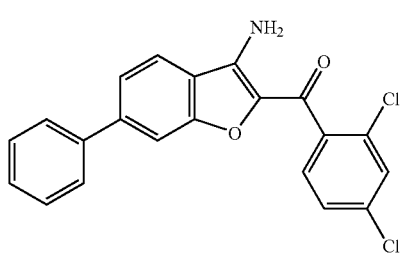

Step 1: Preparation of starting material 2-cyano-5-phenylphenol

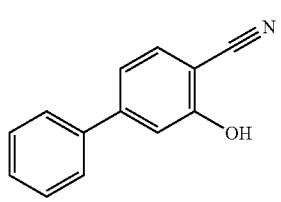

To a stirred solution of 3-phenylphenol (10.0 g, 58.75 mmol) in anhydrous tetrahydrofuran (50 mL) and anhydrous dichloroethane (50 mL) was added, at 0° C., 1.0 M boron trichloride in dichloromethane (64.6 mL, 64.6 mmol, 1.1 eq) followed by methyl thiocyanate (4.4 mL, 64.6 mmol, 1.1 eq) and aluminum chloride (7.83 g, 58.75 mmol, 1.0 eq). The reaction mixture was stirred at room temperature for 2 days and then cooled to 0° C. To the dark brown reaction mixture was added 50% aqueous sodium hydroxide solution (150 mL) until pH reached above 10. The resulting yellow bi-phasic layers were stirred at reflux for 1 h and then cooled to room temperature. The bi-phasic layers were separated, and the aqueous layer was adjusted to pH 3 with 2.0 N hydrogen chloride solution (~300 mL) at 0° C. The acidified aqueous mixture was extracted with ethyl acetate (3×400 mL), and the combined organic layers were dried ($MgSO_4$), filtered, and concentrated under reduced pressure. Crystallization from ether-hexane (150 mL) gave 2-cyano-5-phenylphenol as a white solid (5.81 g, 47.2%). $^1$H-NMR (DMSO-$d_6$) δ 11.20 (s, 1H), 7.66 (d, J=8.7 Hz, 1H), 7.62 to 7.59 (m, 2H), 7.51 to 7.42 (m, 3H), 7.22 to 7.19 (m, 2H), $R_f$=0.08, 25% ethyl acetate-hexane.

Step 2: Preparation of the title compound 3-amino-6-phenyl-1-benzofuran-2-yl)(2,4-dichlorophenyl)methanone To a stirred solution of 2-cyano-5-phenylphenol from step 1 (5.71 g, 29.25 mmol) and 2-chloro-1-(2,4-dichlorophenyl)ethanone (7.19 g, 32.17 mmol, 1.1 eq) in anhydrous N,N-dimethylformamide (50 mL) was added potassium carbonate (4.85 g, 35.1 mmol, 1.2 eq), and the orange reaction mixture was stirred at 90° C. for 17 h. The resulting dark wine color reaction was poured into ethyl acetate (500 mL) and water (300 mL). The ethyl acetate layer was washed with saturated aqueous ammonium chloride, water, and brine. The organic layer was then dried ($MgSO_4$), filtered, and evaporated in vacuo. The crude product was purified on silica gel (flash column chromatography) eluted with 10% ethyl acetate-hexane followed by 20% ethyl acetate-hexane. Crystallization from ether-hexane afforded the benzofuran product as a yellow solid (7.56 g, 67.6%). $^1$H-NMR (DMSO-$d_6$) δ 8.10 (d, J=8.4 Hz, 1H), 7.75 (d, J=3.6 Hz, 1H), 7.74 (d, J=3.0 Hz, 1H), 7.71 (m, 2H), 7.62 to 7.53 (m, 5H), 7.47 to 7.35 (m, 3H); MS LC-MS (MH$^+$=382); Anal. calculated for $C_{21}H_{13}Cl_2NO_2$: 65.99%; H, 3.43%; N, 3.66%. found C, 65.70%; H, 3.40%; N, 3.72%; melting point (uncorrected) 144 to 146.5° C.

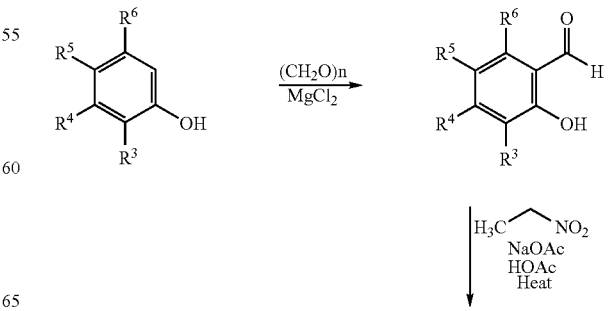

-continued

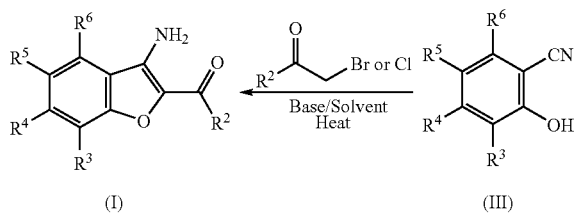

(I)    (III)

Example 24

Method B-2a

Preparation of [3-Amino-6-(2-methyl-oxazol-4-yl)-benzofuran-2-yl]-(2-methoxy-phenyl)-methanone

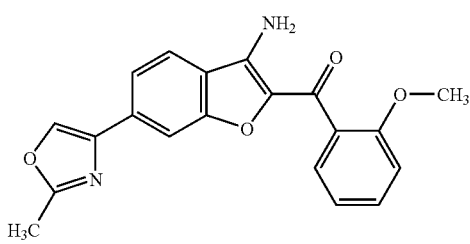

Step 1: Preparation of intermediate 4-(3-methoxy-phenyl)-2-methyl-oxazole

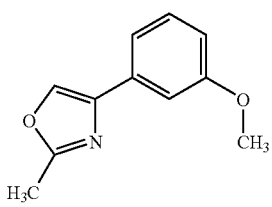

To the solution of 2-bromo-3'-methoxy-acetophenone (1.9 g, 8.1 mmol) in 15 mL toluene was added acetamide (1.2 g. 20.3 mmol, 2.5 eq). The reaction was stirred at 110° C. for 40 h. Filtered off the white solid and washed with ethyl acetate. Evaporated the filtrate (added some methanol to lower the boiling point) and the washings in vacuo. Purification using MPLC (Biotage) gave 1.1 g (72%) of 4-(3-methoxy-phenyl)-2-methyl-oxazole as a light yellow liquid. $^1$H-NMR (CH$_3$OH-d$_4$) δ 8.11 (s, 1H), 7.25 to 7.28 (m, 3H), 6.83 to 6.86 (m, 1H), 3.82 (s, 3H), 2.49 (s, 3H); R$_f$=0.36, 25% ethyl acetate-hexane.

Step 2: Preparation of intermediate 3-(2-Methyl-oxazol-4-yl)-phenol

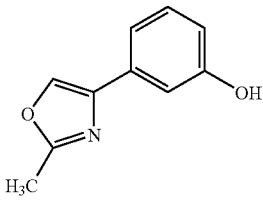

To a solution of 4-(3-methoxy-phenyl)-2-methyl-oxazole (1.1 g, 5.8 mmol) from step 1 in anhydrous DCM (5 mL) was added 1M boron tribromide in DCM (18 mL, 17.4 mmol, 3 eq) in an ice bath. The reaction mixture was stirred at room temperature for 2 h. The mixture was poured into ice and ethyl acetate. To this was added about 50 mL 1 N NaOH, followed by saturated aqueous sodium bicarbonate until pH was 8. Separate the organic layer and extracted the aqueous layer with EtOAc twice. Combined the organic layers and evaporated in vacuo. 0.88 g (87%) 3-(2-Methyl-oxazol-4-yl)-phenol was obtained as a yellow solid. $^1$H-NMR (CH$_3$OH-d$_4$) δ 8.07 (s, 1H), 7.22 to 7.15 (m, 3H), 6.78 to 6.75 (m, 1H), 2.52 (s, 3H); MS LC-MS (MH$^+$=176.3); TLC R$_f$=0.15, 25% EtOAc-HEX.

Step 3: Preparation of intermediate 2-Hydroxy-4-(2-methyl-oxazol-4-yl)-benzaldehyde

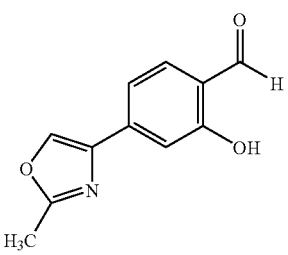

To a solution of 3-(2-Methyl-oxazol-4-yl)-phenol (0.88 g, 5.0 mmol) from step 2 in anhydrous acetonitrite (20 mL) was added magnesium chloride (1.4 g, 15 mmol, 3 eq), triethylamine (2.8 mL, 20 mmol, 4 eq) and paraformaldehyde (0.6 g, 20 mmol, 4 eq). The reaction mixture was refluxed for 17 h. The starting material was completely gone. Added some water and saturated aqueous ammonium chloride until pH=7. At this point some red solid precipitated. Filtered off the red solid and extracted the filtrate with EtOAc 3 times. Most of the red solid was dissolved in MeOH. Combined the EtOAc extract and MeOH filtrate and dried over magnesium sulfate. It was evaporated in vacuo and gave 2Hydroxy-4-(2-methyl-oxazol-4-yl)-benzaldehyde 1.0 g (98%) as a yellow solid. $^1$H-NMR (CH$_3$OH-d$_4$) δ 10.0 (s, 1H), 8.3 (s, 1H), 7.73 (d, J=8

Hz 1H), 7.4 (dd, J=8 Hz, 1.6 Hz, 1H), 7.34 (d, J=1.6 Hz, 1H), 2.54 (s, 3H); TLC R$_f$=0.24, 25% EtOAc-HEX.

Step 4: Preparation of intermediate
2-Hydroxy-4-(2-methyl-oxazol-4-yl)-benzonitrile

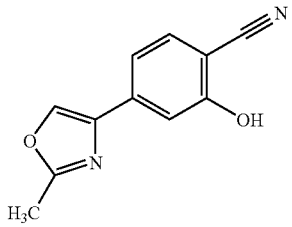

To a solution of 2-hydroxy-4-(2-methyl-oxazol-4-yl)-benzaldehyde (1 g, 4.9 mmol) from step 3 in acetic acid (5 mL) was added nitroethane (0.74 g, 9.8 mmol, 2 eq) and sodium acetate (0.8 g, 9.8 mmol, 2 eq). The reaction mixture was refluxed for 17 h. The starting material was completely gone. Added some water and neutralized the solution with saturated aqueous sodium bicarbonate until pH=7. Extracted with EtOAc 3 times. Combined the extracts and evaporated in vacuo. Purification using MPLC (Biotage) gave 0.2 g (20%) 2-Hydroxy-4-(2-methyl-oxazol-4-yl)-benzonitrile as a light yellow solid. $^1$H-NMR (CH$_3$OH-d$_4$) δ 8.2 (s, 1H), 7.51 (d, J=8 Hz, 1H), 7.31 (d, J=1.6 Hz, 1H), 7.26 (dd, J=8 Hz, 1.6 Hz, 1H), 2.51 (s, 3H).

Step 5: Preparation of [3-Amino-6-(2-methyl-oxazol-4-yl)-benzofuran-2-yl]-(2-methoxy-phenyl)-methanone

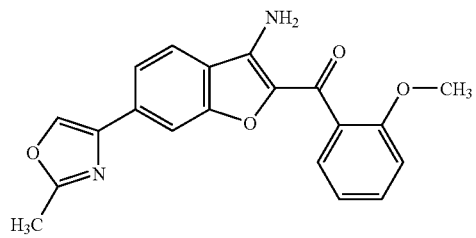

To a solution of 2-hydroxy-4-(2-methyl-oxazol-4-yl)-benzonitrile from step 4 (25 mg, 0.12 mmol) and 2-methoxyphenacyl bromide (31 mg, 0.14 mmol, 1.1 eq) in anhydrous N,N-dimethylformamide (2 mL) was added potassium carbonate (34 mg, 0.25 mmol, 2 eq). The reaction mixture was shaken at 90° C. for 17 h. The mixture was cooled to room temperature and poured into ethyl acetate and water. The aqueous layer was extracted with ethyl acetate twice. Combined the organic layers and evaporated in vacuo. Purification using HPLC gave 19 mg (43%) of [3-Amino-6-(2-methyl-oxazol-4-yl)-benzofuran-2-yl]-(2-methoxy-phenyl)-methanone as a yellow solid. $^1$H-NMR (CH$_3$OH-d$_4$) δ 8.23 (s, 1H), 7.86 (d, J=8 Hz, 1H), 7.65 to 7.39 (m, 4H), 7.13 (d, J=8 Hz, 1H), 7.05 (t, J=7.2 Hz, 1H), 3.82 (s, 3H), 2.51 (s, 3H). MS LC-MS (MH$^+$=349.2); R$_f$=0.33, 50% EtOAc-HEX.

Example 25

Method B-2b

Preparation of [3-Amino-6-(2-methyl-thiazol-4-yl)-benzofuran-2-yl]-(2,4-dichloro-phenyl)-methanone

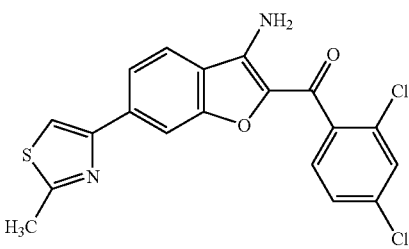

Step 1: preparation of intermediate
4-(3-methoxy-phenyl)-2-methyl-thiazole

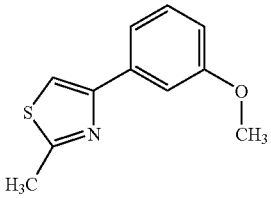

To the solution of 2-bromo-3'-methoxy-acetophenone (1.0 g, 4.4 mmol, 1.2 eq) in 10 mL anhydrous ethanol was added thioacetamide (0.27 g, 3.6 mmol, 1 eq). Some solid was formed immediately. The reaction was stirred at 80° C. for 1 h. The reaction was cooled to rt and then was placed in an ice bath for a while. The white solid was filtered, washed with hexane and dried in vacuum oven to give 0.67 g (90%) of 4-(3-methoxy-phenyl)-2-methyl-thiazole. $^1$H-NMR (CH$_3$OH-d$_4$ and a little DMSO-d$_6$) δ 7.53 (s, 1H), 7.39 (m, 1H), 7.29 to 7.26 (m, 1H), 7.18 (m, 1H), 6.78 (m, 1H), 3.74 (s, 3H), 2.91 (s, 3H); MS LC-MS MH$^+$-206.3; R$_f$=0.13, 2% EtOAc-HEX.

Step 2: Preparation of intermediate
3-(2-Methyl-thiazol-4-yl)-phenol

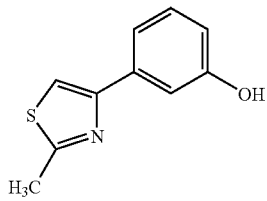

The same procedure was used as in the preparation of 3-(2-methyl-oxazol-4-yl)-phenol method described in Example 24 above. Yield 74%. $^1$H-NMR (CH$_3$OH-d$_4$) δ 7.54

(s, 1H), 7.32 to 7.19 (m, 3H), 6.77 to 6.74 (m, 1H), 2.76 (s, 3H); TLC $R_f$=0.57, 50% EtOAc-HEX.

Step 3: Preparation of intermediate
2-Hydroxy-4-(2-methyl-thiazol-4-yl)-benzaldehyde

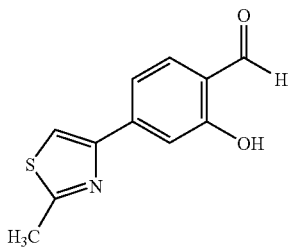

The procedure used was the same as that described in the preparation of 2-hydroxy-4-(2-methyl-oxazol-4-yl)-benzaldehyde. TLC $R_f$=0.71, 50% EtOAc-HEX. The crude product was used in step 4 without further purification.

Step 4: Preparation of intermediate
2-Hydroxy-4-(2-methyl-thiazol-4-yl)-benzonitrile
for use in making

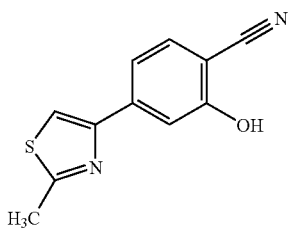

The same procedure was used as described in the preparation of the intermediate 2-hydroxy-4-(2-methyl-oxazol-4-yl)-benzonitrile. Two steps overall yield was 83%. $^1$H-NMR (CH$_3$OH-d$_4$) δ 7.75 (s, 1H), 7.52 (d, J=8.2 Hz, 1H), 7.48 (d, J=1.6 Hz 1H), 7.42 (dd, J=8.2 Hz, 1.6 Hz, 1H), 2.75 (s, 3H). MS LC-MS MH$^+$=217.2; $R_f$=0.18, 30% EtOAc-HEX.

Step 5: Preparation of 2[3-Amino-6-(2-methyl-thiazol-4-yl)-benzofuran-2-yl]-(2,4-dichloro-phenyl)-methanone

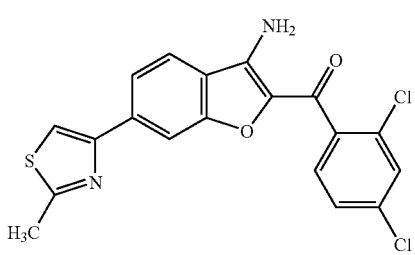

The same procedure was used as described in the preparation of Example 24, step 5. Yield 33%. $^1$H-NMR (DMSO-d$_6$) δ 8.09 (s, 1H), 8.06 (dd, J=8.2 Hz, 0.8 Hz, 1H), 7.94 (m, 1H), 7.89 (dd, J=8.2 Hz, 1.2 Hz, 1H), 7.75 (dd, J=2 Hz, 0.4 Hz, 1H), 7.59 (dd, 8.2 Hz, 0.4 Hz, 1H), 7.55 (dd, J=8.2 Hz, 1.6 Hz, 1H), 2.71 (s, 3H). MS LC-MS (MH$^+$ 403.2/405.2); $R_f$=0.57, 50% EtOAc-HEX.

Example 26

Method B-2c

Preparation of [3-Amino-6-(1-methyl-1H-pyrazol-3-yl)-benzofuran-2-yl]-(2,4-dichloro-phenyl)-methanone

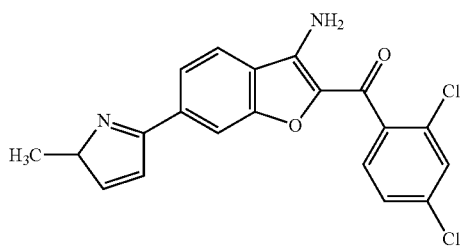

Step 1: Preparation of intermediate
3-(1-methyl-1H-pyrazol-3-yl)-phenol

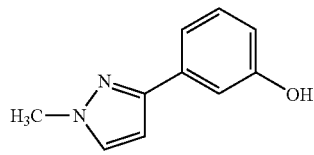

3-hydroxy-acetophenone (1 g, 7.3 mmol) and N,N-dimethylformamide-dimethyl acetal (2.6 g, 22 mmol, 3 eq) were shaken in a 40 mL vial at rt for 17 h. The mixture was evaporated in vacuo and obtained both phenol product and methyl phenol ether. To the solution of this mixture in 10 mL anhydrous ethanol was added methyl hydrazine (1 g, 22 mmol; 3 eq). The reaction mixture was shaken at 80° C. for 2 h. The mixture was evaporated in vacuo. Boron tribromide (3 eq) in dichloromethane was used to de-methylate the methyl ether as described in the preparation of Example 24 step 2. Some methyl ether still existed and the mixture was used for step 2 without further purification.

Step 2: Preparation of intermediate 2-Hydroxy-4-(1-methyl-1H-pyrazol-3-yl)-benzonitrile

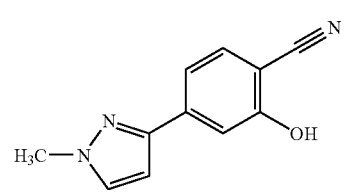

The same procedure was used as described in the preparation of Example 24, step 3 and step 4: 250 mg of 2-Hydroxy-4-(1-methyl-1H-pyrazol-3-yl)-benzonitrile and its isomer 2-Hydroxy-6-(1-methyl-1H-pyrazol-3-yl)-benzonitrile were obtained as a yellow solid. The mixture was used in step 3 without further purification. MS LC-MS MH⁺=200.1; TLC $R_f$=0.16, 50% EtOAc-HEX.

Step 3: Preparation of [3-Amino-6-(1-methyl-1H-pyrazol-3-yl)-benzofuran-2-yl]-(2,4-dichloro-phenyl)-methanone

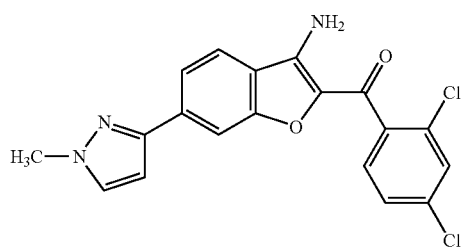

The same procedure was used as described for the preparation of Example 24 step 5. [3-Amino-6-(1-methyl-1H-pyrazol-3-yl)-benzofuran-2-yl]-(2,4-dichloro-phenyl)-methanone was obtained as a light yellow solid. Yield was 12%. $^1$H-NMR (CDCl$_3$) δ 7.7 to 7.8 (m, 2H), 7.60 (d, J=10.8 Hz, 1H), 7.51 to 7.48 (m, 2H), 7.38 to 7.33 (m, 2H), 6.55 (d, J=3.2 Hz, 1H), 5.99 (broad, s, 2H); 3.94 (s, 3H). MS LC-MS MH⁺=386.2/388.2; TLC $R_f$=0.3, 50% EtOAc-HEX.

Reaction Scheme for General Method B-3

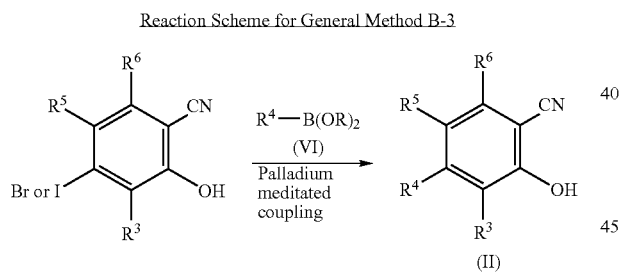

Example 27

Method B-3

Preparation of (3-Amino-6-pyridin-3-yl-benzofuran-2-yl)-(2-methoxy-phenyl)-methanone

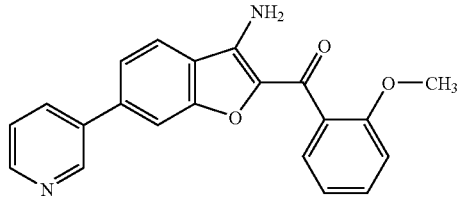

Step 1: Preparation of starting material: 2-Benzyloxy-4-pyridin-3-yl-benzonitrile

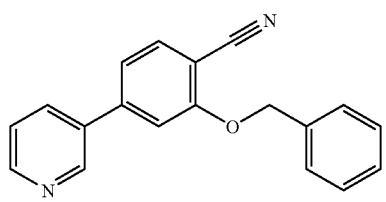

This compound was prepared from 2-benzyloxy-4-iodo-benzonitrile (2.0 g, 5.97 mmol) in the manner described for [3-amino-6-(pyridin-3-yl)-1-benzofuran-2-yl](2,4-dichlorophenyl)methanone, affording 1.42 g (83%) of a tan solid. $^1$H-NMR (DMSO-d$_6$) δ 8.98 (d, J=1.8 Hz, 1H), 8.64 (dd, J=5.1 Hz, 1.5 Hz, 1H), 8.18 (dt, J=8.0 Hz, 2.1 Hz, 1H), 8.86 (d, J=7.8 Hz, 1H), 7.68 (d, J=1.2 Hz, 1H), 7.56 to 7.32 (m, 7H), 5.42 (s, 2H); LC-MS (ES MH⁺=287, RT=2.39 min); $R_f$=0.08 (25% ethyl acetate-hexane).

Step 2: Preparation of starting material: 2-hydroxy-4-(pyridin-3-yl)benzonitrile

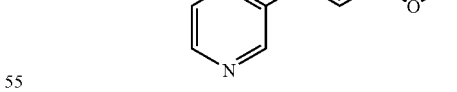

To a dry flask charged with 10% Pd/C (160.0 mg, 0.56 mmol, 0.2 eq) was added a solution of 2-benzyloxy-4-pyridin-3-yl-benzonitrile (800.0 mg, 2.79 mmol) in 1:1 v/v ethyl acetate-ethanol (28.0 mL). The reaction mixture was hydrogenated under an atmosphere of hydrogen supplied by an attached balloon for 16 h. The reaction was filtered through a pad of celite, and the filtrate was concentrated to give 536.4 mg (97.8%) of a white solid. $^1$H-NMR (DMSO-d$_6$) δ 11.21 (broad s, 1H), 8.82 (dd, J=2.4 Hz, 0.6 Hz, 1H), 8.61 (dd, J=5.1 Hz, 1.8 Hz, 1H), 8.02 (ddd, J=7.8 Hz, 2.1 Hz, 1.2 Hz, 1H), 7.71 (d, J=8.4 Hz, 1H), 7.50 (ddd, J=8.1 Hz, 4.5 Hz, 0.6 Hz, 1H), 7.27 to 7.22 (m, 2H); LC-MS (ES MH+=197, RT=0.97 min); $R_f$=0.16 (75% ethyl acetate-hexane).

Step 3: Preparation of the title compound: (3-Amino-6-pyridin-3-yl-benzofuran-2-yl)-(2-methoxy-phenyl)-methanone

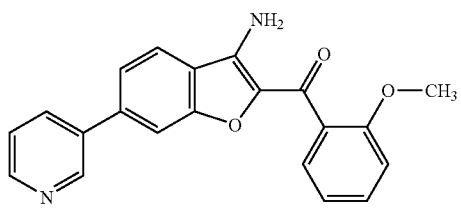

To a stirred solution of 2-hydroxy-4-(pyridin-3-yl)benzonitrile (60.0 mg, 0.31 mmol) and 2-bromo-2'-methoxyacetophenone (70.1 mg, 0.31 mmol, 1.0 eq) in anhydrous N,N-dimethylformamide (5.0 mL) was added potassium carbonate (84.5 mg, 0.62 mmol, 2.0 eq), and the orange reaction mixture was stirred at 80° C. for 17 h. The resulting dark wine color reaction was poured into ethyl acetate (100 mL) and water (50 mL). The ethyl acetate layer was washed with saturated aqueous ammonium chloride, water, and brine. The organic layer was then dried over sodium sulfate, filtered, and evaporated under reduced pressure. The crude product was purified on the MPLC (Biotage) eluted with 50% ethyl acetate-hexane. Crystallization from ether-hexane afforded the benzofuran as a yellow solid (24.4 mg, 23.2%). $^1$H-NMR (Acetone-$d_6$) δ 8.98 (d, J=1.5 Hz, 1H), 8.60 (dd, J=7.2, 1.5 Hz, 1H), 8.12 (m, 2H), 7.70 (d, J=1.5 Hz, 1H), 7.65 (dd, J=6.3, 0.9 Hz, 1H), 7.52 to 7.41 (m, 3H), 7.17 (d, J=7.5 Hz, 1H), 7.06 (t, J=6.6 Hz, 1H), 6.84 (broad, s, 2H), 2.85 (s, 3H); LC-MS (ES MH+=345, RT=1.97 min).

Example 28

Method B-4

Preparation of N-{3-[3-amino-2-(2,4-dichloro-benzoyl)-benzofuran-6-yl]-pyridin-1-yl}-propionamide

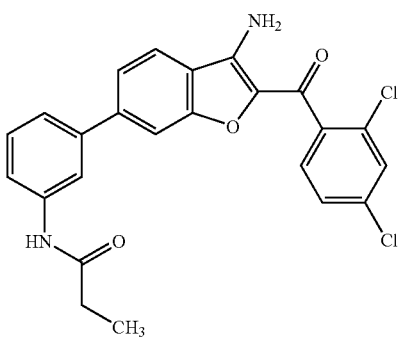

Step 1: Preparation of 3'-amino-3-benzyloxy-biphenyl-4-carbonitrile

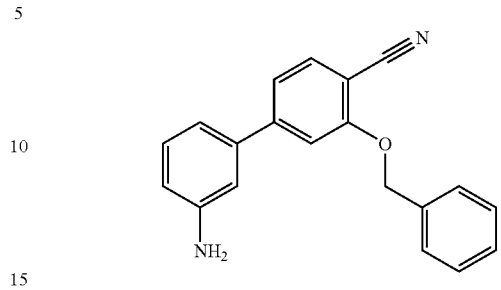

A solution of 2-(benzyloxy)-4-iodobenzonitrile (6.20 g, 18.5 mmol) in 1,2-dimethoxyethane was degassed with argon for 30 min. At this time, tetrakis(triphenyl phosphine)palladium(0), (2.13 g, 1.85 mmol, 0.1 eq) was added followed by 3-aminophenyl boronic acid (2.53 mg, 18.5 mmol, 1.0 eq) and 2M aqueous $Na_2CO_3$ (4.0 mL). The reaction was bubbled with argon for another 10 min and then heated to 80° C. overnight (18 h). The reaction was diluted with ethyl acetate, washed with water, brine, and dried over magnesium sulfate. The solvent was removed at reduced pressure and purified on the MPLC (Biotage) eluted with 30% ethyl acetate-hexane to afford 3.33 g (59.9%) of a yellow solid as the product. $^1$H-NMR (Acetone) δ 7.71 (d, J=8.1 Hz, 1H), 7.58 (m, 2H), 7.48 to 7.30 (m, 5H), 7.18 (m, 1H), 6.99 (m, 1H), 6.90 (m, 1H), 6.76 (m, 1H), 5.44 (s, 2H), 4.81 (broad, s, 2H); $R_f$=0.32 (30% ethyl acetate-hexane).

Step 2: Preparation of N-(3'-benzyloxy-4'-cyano-biphenyl-3-yl)-N-propionyl-propionamide

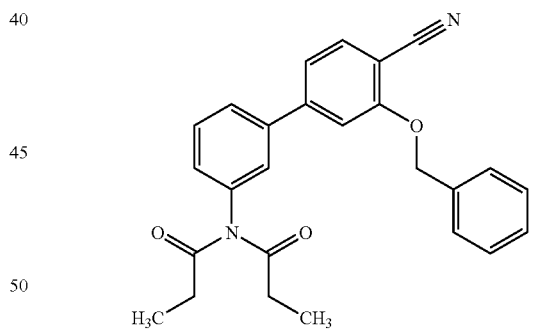

To a solution of 3'-amino-3-benzyloxy-biphenyl-4-carbonitrile (800 mg, 2.66 mmol) in dichloromethane (100 mL) at 0° C. was added dropwise propionyl chloride (370 mg, 4.00 mmol, 1.5 eq) followed by triethylamine (405 mg, 4.00 mmol, 1.5 eq). The reaction was stirred at 0° C. under argon for 1 h. The reaction was concentrated, and the residue was dissolved in ethyl acetate. The organic layer was washed with water, brine, and dried over magnesium sulfate. The solvent was removed at reduced pressure and purified on the MPLC (Biotage) eluted with 30% ethyl acetate-hexane to afford 980 mg (89.2%) of a yellow solid as the product. $^1$H-NMR (Acetone-$d_6$) δ 7.76 (m, 2H), 7.69 (m, 1H), 7.64 to 7.55 (m, 4H), 7.48 to 7.36 (m, 5H), 5.45 (s, 2H), 2.61 (q, J=6.9 Hz, 4H), 1.05 (t, J=6.6 Hz, 6H); $R_f$=0.42 (30% ethyl acetate-hexane).

Step 3: Preparation of N-(4'-cyano-3'-hydroxy-biphenyl-3-yl)-N-propionyl-propionamide

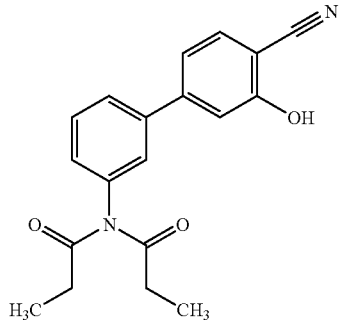

To a dry flask charged with 10% Pd/C (124.0 mg, 0.13 eq) was added a solution of N-(3'-benzyloxy-4'-cyano-biphenyl-3-yl)-N-propionyl-propionamide (980 mg, 2.38 mmol) in 1:1 v/v ethyl acetate-ethanol (10 mL). The reaction mixture was hydrogenated under an atmosphere of hydrogen supplied by an attached balloon for 24 h. The reaction was filtered through a pad of celite, and the filtrate was concentrated. Purification on the MPLC (Biotage) eluted with 30% ethyl acetate-hexane afforded 332 mg (43.4%) of the product. $^1$H-NMR (Acetone-$d_6$) δ 9.95 (broad s, 1H), 7.75 to 7.58 (m, 4H), 7.35 (m, 3H), 2.61 (q, J=7.2 Hz, 4H), 1.05 (t, J=7.2 Hz, 6H); LC-MS (ES MH$^+$=323) $R_f$=0.20 (30% ethyl acetate-hexane).

Step 4: Preparation of the title compounds: N—{3-[3-amino-2-(2,4-dichloro-benzoyl)-benzofuran-6-yl]-phenyl}-N-propionyl-propionamide

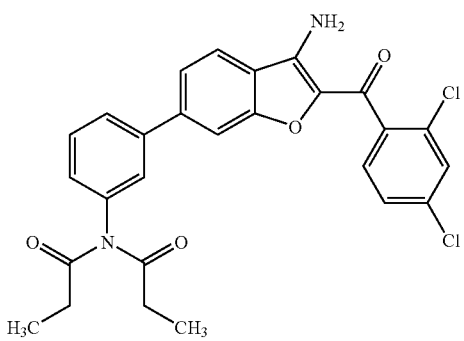

To N-(4'-cyano-3'-hydroxy-biphenyl-3-yl)-N-propionyl-propionamide (70.0 mg, 0.22 mmol) and 2, 2',4'-trichloro-acetophenone (48.5 mg, 0.22 mmol, 1.0 eq) in anhydrous N,N-dimethylformamide (5 mL) was added potassium carbonate (60.0 mg, 0.43 mmol, 2.0 eq). The reaction mixture was stirred under argon at 80° C. for 16 h. The brown reaction mixture was cooled and diluted with ethyl acetate and water. The organic layer was washed with saturated aqueous ammonium chloride, water, brine, and dried over sodium sulfate. The solvent was evaporated under reduced pressure, and the crude product was purified on the MPLC (Biotage) eluted with 20% ethyl acetate-hexane to give 39.6 mg (35.8%) of the product. $^1$H-NMR (Acetone-$d_6$) δ8.10 (d, J=8.4 Hz, 1H), 7.83 (d, J=6.3 Hz, 1H), 7.72 to 7.53 (m, 7H), 7.30 (m, 1H), 7.08 (broad, s, 2H), 2.63 (q, J=7.2 Hz, 4H), 1.04 (t, J=7.2 Hz, 6H); MS ES (MH$^+$=509); $R_f$=0.25 (30% ethyl acetate-hexane).

Step 5: Preparation of N-{3-[3-amino-2-(2,4-dichloro-benzoyl)-benzofuran-6-yl]-pyridin-1-yl}-propionamide

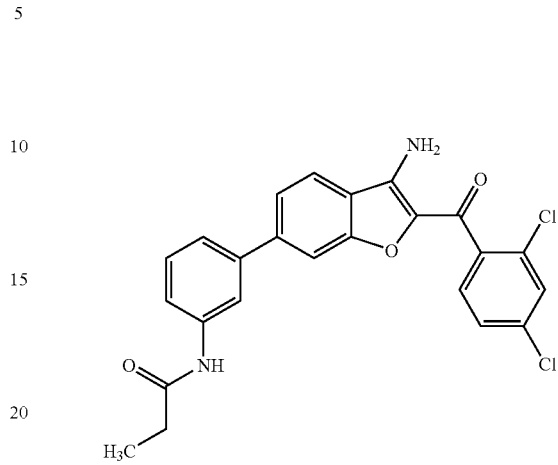

To N-{3-[3-amino-2-(2,4-dichloro-benzoyl)-benzofuran-6-yl]-phenyl}-N-propionyl-propionamide (230 mg, 0.45 mmol) in anhydrous THF (5 mL) was added 2 N aq. NaOH (0.46 mL, 0.90 mmol, 2.0 eq). The reaction mixture was stirred at reflux for 16 h. The reaction mixture was diluted with ethyl acetate and water. The organic layer was washed with saturated aqueous ammonium chloride, water, brine, and dried over sodium sulfate. The solvent was evaporated under reduced pressure and the crude product was purified on the MPLC (Biotage) eluted with 20% ethyl acetate-hexane to give 161 mg (78.4%) of a yellow solid. $^1$H-NMR (Acetone-$d_6$) δ 9.02 (broad s, 1H), 8.00 (m, 1H), 7.95 (d, J=6.9 Hz, 1H), 7.53 to 7.40 (m, 6H), 7.28 (m, 2H), 6.96 (broad s, 2H), 2.26 (q, J=7.8 Hz, 2H), 1.04 (t, J=4.5 Hz, 3H); MS ES (MH$^+$=453); $R_f$=0.28 (30% ethyl acetate-hexane).

Example 29

Method B-5

Exemplified by the [3-amino-6(4-methyl-thiophen-3-yl)-benzofuran-2-yl]-(2,4-dichloro-phenyl)-methanone

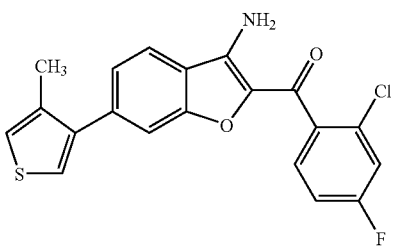

Step 1: Preparation of 2-Hydroxy-4-(4-methyl-thiophen-3-yl)-benzonitrile

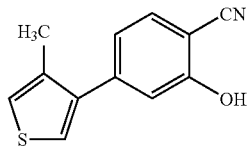

4-Bromo-2-methoxy-benzonitrile (2.4 g, 11.32 mmol) was dissolved into DMF (25 mL). To this solution was added bis(pinacolato)diboron (3 g, 11.88 mmol), palladium(II) acetate (0.76 g, 0.34 mmol), and potassium acetate (3.3 g, 34 mmol). This mixture was degassed by purging with Ar for 15 min and heated to 80° C. for 5 h. To the mixture was then added 3-bromo-4-methyl-thiophene (1.8 g, 10.2 mmol), cesium carbonate (5.53 g, 17 mmol), and tetrakis(triphenylphosphine)palladium(0). The solution was stirred for 18 h at 80° C. The reaction mixture was poured into an ethyl acetate:water (1:1, 200:200 mL) system. The organic was separated and further product was extracted using EtOAc (3×200 mL). The organic layers were combined, washed with brine (100 mL) and dried using sodium sulfate. The organic layer was concentrated in vacuo and the crude product was dissolved into methylene chloride (2.5 mL) and cooled to 0° C. Aluminum chloride (0.726 g, 5.45 mmol) was added and the solution was stirred for 5 min. Ethane thiol (0.339 g, 5.45 mmol) was then added and the solution was stirred for 2 h at rt. Water (10 mL) was added to quench the reaction and the product was extracted from the aqueous layer via methylene chloride (3×20 mL). The organics were combined and dried with sodium sulfate. The organic solution was then concentrated in vacuo. Flash chromatography (10% EtOAc:HEX→30% EtOAc:Hex) yielded 0.231 g (9.75%) of 2-hydroxy-4-(4-methyl-thiophen-3-yl)-benzonitrile. $^1$HNMR (methylene chloride-d$_2$) δ 7.56 (d, J=8.5 Hz, 1H), 7.31 (d, J=4.2 Hz, 1H), 7.25-7.03 (m, 4H), 2.29 (s, 3H). LC-MS RT: 3.34 min, [M+H]+:: 216.1.

Step 2: Preparation of [3-amino-6(4-methyl-thiophen-3-yl)-benzofuran-2-yl]-(2,4-dichloro-phenyl)-methanone

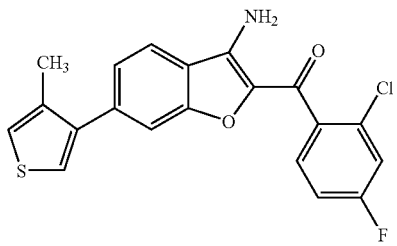

To a stirred solution of 2-hydroxy-4-(4-methyl-thiophen-3-yl)-benzonitrile from step 1 (0.050 g, 0.23 mmol) and 2-bromo-1-(2-chloro-4-fluoro-phenyl)-ethanone (0.071 g, 0.28 mmol, 1.2 eq) in anhydrous N,N-dimethylformamide (2 mL) was added potassium carbonate (0.048 g, 0.35 mmol, 1.5 eq), and the orange reaction mixture was stirred at 80° C. for 18 h. The resulting dark, wine-colored reaction was poured into ethyl acetate (5 mL) and water (5 mL). The ethyl acetate layer was washed with water and brine. The organic layer was then dried (MgSO$_4$), filtered, and evaporated in vacuo. The crude product was taken up in acetonitrile (2 mL) and purified by HPLC (10% acetonitrile:water→90% acetonitrile:water). The benzofuran product was collected as a yellow solid (0.066 g, 40.0%). $^1$H-NMR (CD$_2$Cl$_2$) δ 7.72 (d, J=7.6 Hz, 1H), 7.63-7.584 (m, 1H), 7.38-7.30 (m, 4H), 7.18-7.09 (m, 2H), 6.05 (s, 2H), 2.30 (s, 3H); MS LC-MS (MH$^+$=386.2), RT=4.12 min.

Additional compounds illustrated in Table 1 were prepared as described above by choosing the appropriate starting materials that are readily available and/or the synthesis of which is taught herein, and using the processes of Methods A and/or B described above or other standard chemical processes known in the art.

TABLE 1

Examples Synthesized using Method B

| Example | Structure | R$_f$(TLC solvent) Or RT (min)* | LC/MS ([M + H]+) | Synthesis of (III)** | Synthesis of (I) |
|---|---|---|---|---|---|
| 30 | 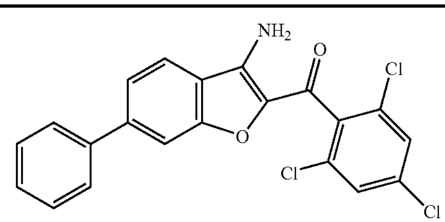 | R$_f$ = 0.41 [25% EtOAc/HEX] | 416.0 | A-1 | B-1 |
| 31 | 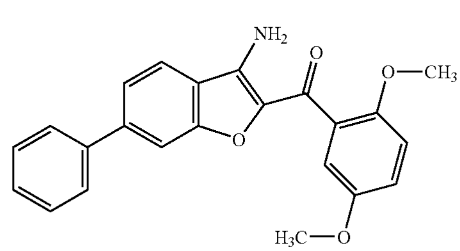 | R$_f$ = 0.50 [30% EtOAc/HEX] | 374.0 | comm | B-1 |

TABLE 1-continued

Examples Synthesized using Method B

| Example | Structure | R_f (TLC solvent) Or RT (min)* | LC/MS ([M + H]+) | Synthesis of (III)** | Synthesis of (I) |
|---|---|---|---|---|---|
| 32 | 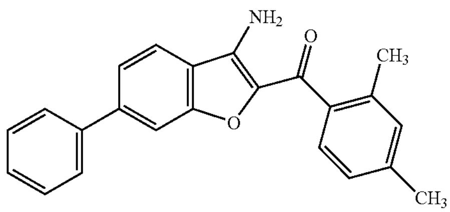 | R_f = 0.45 [30% EtOAc/HEX] | 342.0 | comm | B-1 |
| 33 | 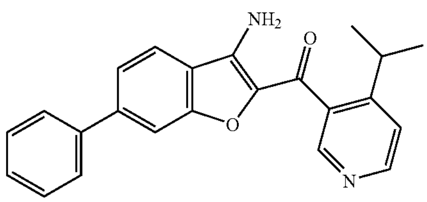 | R_f = 0.30 [30% EtOAc/HEX] | 357.0 | A-4 | B-1 |
| 34 | 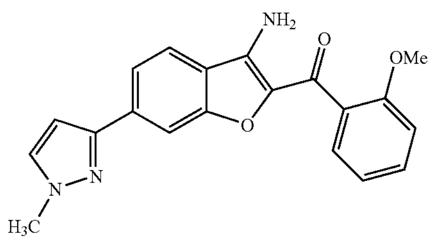 | R_f = 0.14 @ N 50/50 EtOAc/HEX | 348.2 | comm | B-2 |
| 35 | 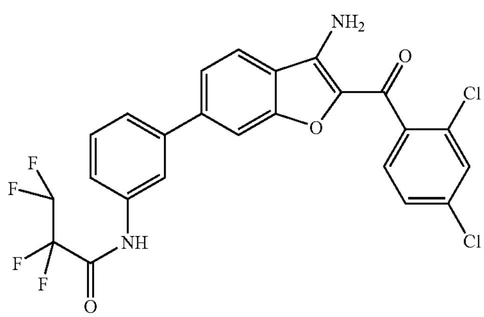 | R_f = 0.43, HEX/EtOAc = 70/30 | 525.0 | comm | B-4 |
| 36 | 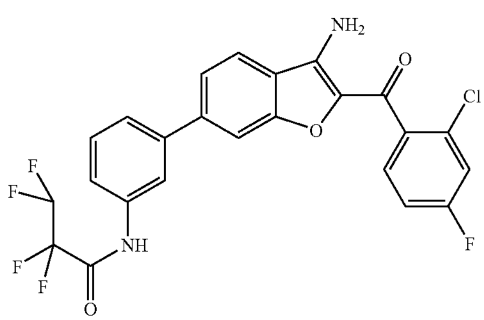 | R_f = 0.42, HEX/EtOAc = 70/30 | 509.0 | comm | B-4 |

TABLE 1-continued

Examples Synthesized using Method B

| Example | Structure | $R_f$(TLC solvent) Or RT (min)* | LC/MS ([M + H]+) | Synthesis of (III)** | Synthesis of (I) |
|---|---|---|---|---|---|
| 37 | 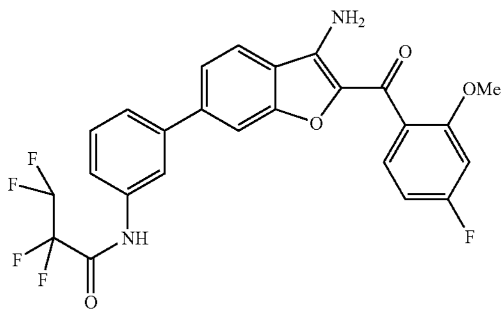 | $R_f$ = 0.28, HEX/EtOAc = 70/30 | 505.0 | comm | B-4 |
| 38 | 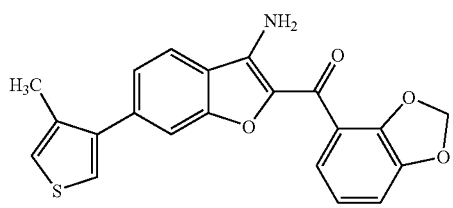 | RT = 3.91 | 378.2 | A-5 | B-5 |
| 39 | 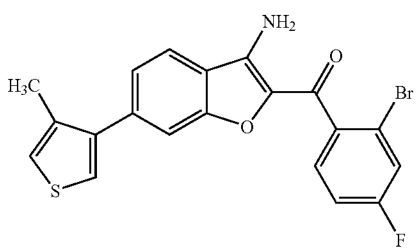 | RT = 4.09 | 430/432 | A-2 | B-5 |
| 40 | 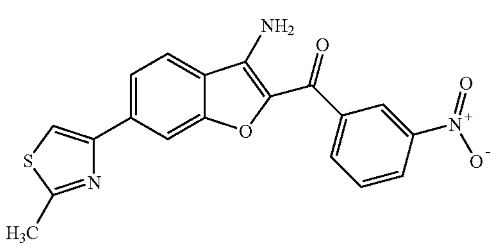 | $R_f$ = 0.51 [50% EtOAc/HEX] | 380 | comm | B-2 |
| 41 | 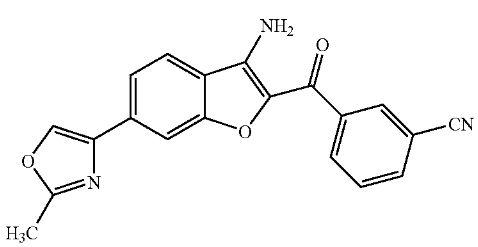 | $R_f$ = 0.4 [50% EtOAc/HEX] | 344 | comm | B-2 |

TABLE 1-continued

Examples Synthesized using Method B

| Example | Structure | $R_f$(TLC solvent) Or RT (min)* | LC/MS ([M + H]+) | Synthesis of (III)** | Synthesis of (I) |
|---|---|---|---|---|---|
| 42 | 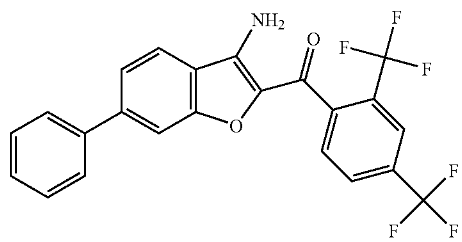 | $R_f$ = 0.34 [25% EtOAc/Hex] | 450 | A-2 | B-1 |
| 43 | 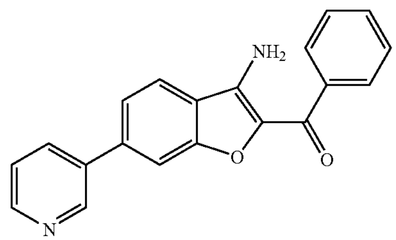 | RT = 2.81 | 315.0 | comm | B-3 |

Footnotes:
*The following are the LCMS conditions: HPLC - electrospray mass spectra (HPLC ES-MS) were obtained using a Gilson HPLC system equipped with two Gilson 306 pumps, a Gilson 215 Autosampler, a Gilson diode array detector, a YMC Pro C-18 column (2 × 23 mm, 120 A), and a Micromass LCZ single quadrupole mass spectrometer with z-spray electrospray ionization. Spectra were scanned from 120-1000 amu over 2 seconds. ELSD (Evaporative Light Scattering Detector) data was also acquired as an analog channel. Gradient elution was used with Buffer A as 2% acetonitrile in water with 0.02% TFA and Buffer B as 2% water in Acetonitrile with 0.02% TFA at 1.5 mL/min. Samples were eluted as follows: 90% A for 0.5 min ramped to 95% B over 3.5 min and held at 95% B for 0.5 min and then the column is brought back to initial conditions over 0.1 min. Total run time is 4.8 min.
**comm means commercially available.

General Method C: Preparation of Formula (I) Compounds Via 6-Iodo-Benzofurans (IV)

Illustrated in the Reaction Scheme for General Method C below is a generally applicable method for the preparation of compounds of formula (I) via intermediates of formulas (IV) and (V). The condensation of properly substituted 2-cyano-5-iodo-phenol (II) and 1-aryl-2-haloethanone (III) under basic conditions (such as cesium carbonate, potassium carbonate, sodium carbonate, DBU), in a solvent such as DMF, MeCN at temperatures between room temperature to 100° C. to give 6-iodo-benzofuran (IV). Palladium mediated coupling reactions between (IV) and arylboronic acids or boronates (VI) afford the desired compounds. Alternatively, 6-iodo-benzofuran (IV) was converted to boronate (V), which was then used to prepare the desired compounds via palladium mediated coupling with arylhalides (VII).

Reaction Scheme for General Method C

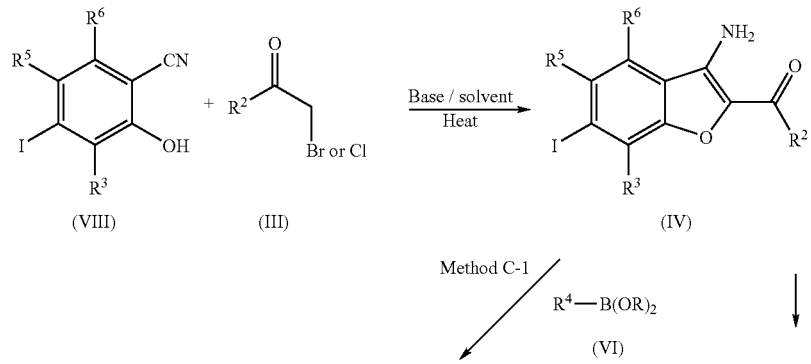

-continued

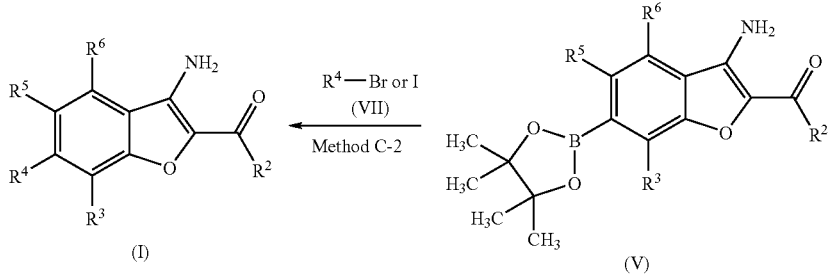

Example 44

Method C-1a

Preparation of [3-amino-6-(3-pyridinyl)-1-benzofuran-2-yl](2,4-dichlorophenyl)methanone

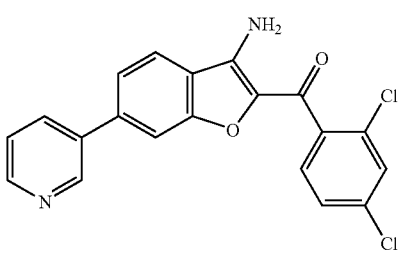

Step 1: Preparation of the starting material: 2-Cyano-5-iodophenol

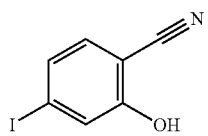

To a stirred solution of 3-iodophenol (20.0 g, 90.9 mmol) in anhydrous dichloroethane (60 mL) was added, at 0° C., 1.0 M boron trichloride in dichloromethane (100 mL, 100.0 mmol, 1.1 eq), followed by methyl thiocyanate (6.85 mL, 100.0 mmol, 1.1>eq) and aluminum chloride (12.1 g, 90.9 mmol, 1.0 eq). The reaction mixture was stirred at room temperature for 3 days and then cooled to 0° C. To the dark brown reaction mixture was added 50% aqueous sodium hydroxide solution (150 mL) until pH 11. The resulting yellow biphasic layers were stirred at reflux for 3 h and then cooled to room temperature. The biphasic layers were separated, and the aqueous layer was adjusted to pH 1 with 50% aqueous hydrogen chloride solution at 0° C. The acidified aqueous mixture was extracted with ethyl acetate (3×400 mL), and the combined organic layers were dried ($Na_2SO_4$), filtered, and concentrated under reduced pressure. Crystallization from ether-hexane (200 mL) gave 2-cyano-5-iodophenol as a white solid (14.8 g, 66.4%). $^1$H-NMR (DMSO-$d_6$) δ 11.43 (s, 1H), 7.38 to 7.36 (m, 2H), 7.29 (dd, J=8.4, 1.5 Hz, 1H); MS GC-MS ($M^+$=245; RT=7.45 min); $R_f$=0.16, 25% ethyl acetate-hexane.

Step 2: Preparation of the intermediate: (3-amino-6-iodo-1-benzofuran-2-yl)(2,4-dichlorophenyl)methanone

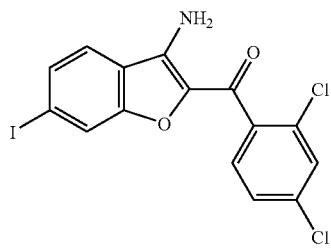

To a stirred solution of 2-cyano-5-iodophenol (3.68 g, 15.0 mmol) and 2,2',4'-trichloroacetophenone (4.02 g, 18.0 mmol, 1.2 eq) in anhydrous N,N-dimethylformamide (15 mL) was added potassium carbonate (3.11 g, 22.5 mmol, 1.5 eq), and the orange reaction mixture was stirred at 80° C. for 16 h. The resulting dark wine color reaction was poured into ethyl acetate (500 mL) and water (300 mL). The ethyl acetate layer was washed with saturated aqueous ammonium chloride, water, and brine. The organic layer was then dried ($Na_2SO_4$), filtered, and evaporated under reduced pressure. The crude product was purified on the MPLC (Biotage) eluted with 20% ethyl acetate-hexane. Crystallization from dichloromethane-hexane afforded the benzofuran as a yellow solid (6.16 g, 95.0%). $^1$H-NMR (DMSO-$d_6$) δ 7.88 (d, J=1.2 Hz, 1H), 7.82 (d, J=8.4 Hz, 1H), 7.74 (dd, J=1.5, 0.9 Hz, 1H), 7.61 (dd, J=8.4, 1.5 Hz, 1H), 7.55 to 7.51 (m, 4H); LC-MS (ES $MH^+$=432/434).

Step 3: Preparation of the title compound: [3-amino-6-(3-pyridinyl)-1-benzofuran-2-yl](2,4-dichlorophenyl)methanone

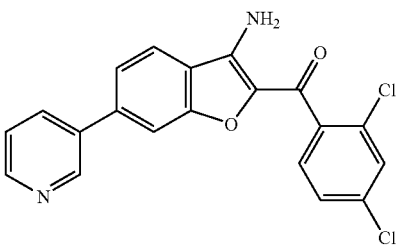

A solution of (3-amino-6-iodo-1-benzofuran-2-yl)(2,4-dichlorophenyl)methanone (2.0 g, 4.63 mmol) in toluene (10 mL) and ethanol (10 mL) was degassed with argon for 10 min. At this time, pyridine-3-boronic acid (740 mg, 6.02 mmol, 1.3 eq) was added followed by [1,1'-bis(diphenylphosphino)-ferrocene]dichloro-palladium(II), complex with dichloromethane (1:1) (378 mg, 0.46 mmol, 0.1 eq) and 2M aqueous $Na_2CO_3$ (11.6 mL). The reaction was bubbled with argon for another 10 min and then heated to 80° C. overnight. The reaction was diluted with ethyl acetate, washed with water, brine, and dried over magnesium sulfate. The solvent was removed at reduced pressure and purified on the MPLC (Biotage) eluted with 45 to 65% ethyl acetate-hexane to afford 1.69 g (95.3%) of a yellow solid as the product. $^1$H-NMR (DMSO-$d_6$) δ 8.95 (d, J=2.4 Hz, 1H), 8.56 (dd, J=4.5, 1.5 Hz, 1H), 8.14 (d, J=8.4 Hz, 2H), 7.83 (s, 1H), 7.76 (d, J=1.8 Hz, 1H), 7.66 (dd, J=8.1, 1.2 Hz, 1H), 7.58 to 7.53 (m, 4H), 7.47 (dd, J=8.4, 4.8 Hz, 1H); LC-MS (ES MH$^+$=383/385, RT=2.58 min). Anal. calculated for $C_{20}H_{12}Cl_2N_2O_2$: C, 62.68%; H, 3.16%; N, 7.31%. found C, 62.41%; H, 3.18%; N, 7.23%.

Example 45a

Method C-1b

Preparation of (3-Amino-5-fluoro-6-pyridin-3-yl-benzofuran-2-yl)-(2,4-dichloro-phenyl)-methanone

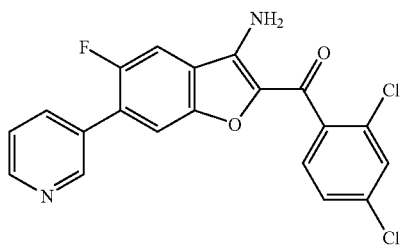

Step 1: Preparation of starting material: 4-amino-2-benzyloxy-5-fluorobenzonitrile

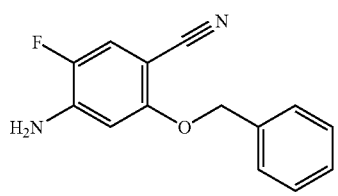

A mixture of 4-amino-2,5-difluorobenzonitrile (500 mg, 3.24 mmol), benzyl alcohol (385.9 mg, 3.57 mmol, 1.1 eq), potassium carbonate (896.2 mg, 6.49 mmol, 2.0 eq), and 4 angstroms molecular sieves (500 mg) in anhydrous N,N-dimethylformamide (6.5 mL) was stirred at 100° C. under argon for 24 h. The reaction was diluted with ethyl acetate, washed with water, brine, and dried over sodium sulfate. The solvent was removed at reduced pressure, and the crude material was purified on the MPLC (Biotage) eluted with 15% ethyl acetate-hexane to afford 155.0 mg (19.7%) of the product. $^1$H-NMR (DMSO-$d_6$) δ 7.42 to 7.32 (m, 6H), 6.49 (d, J=7.5 Hz, 1H), 6.27 (broad s, 2H), 5.09 (s, 2H); LC-MS (ES MH$^+$=243, RT=2.75 min); $R_f$=0.27 (25% ethyl acetate-hexane).

Step 2: Preparation of starting material: 5-fluoro-2-hydroxy-4-iodobenzonitrile

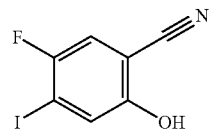

To a slurry of 4-amino-2-benzyloxy-5-fluorobenzonitrile (155.0 mg, 0.64 mmol) in concentrated aq. HCl (2.6 mL) at 0° C. was added sodium nitrite (66.2 mg, 0.96 mmol, 1.5 eq) dissolved in water (1.0 mL). After stirring at 0° C. for 1 h, a solution of potassium iodide (159.3 mg, 0.96 mmol, 1.5 eq) dissolved in water (5.1 mL) was added, and the reaction mixture was stirred at ambient temperature for 3 days. The reaction was diluted with ethyl acetate, washed with water, brine, and dried over sodium sulfate. The solvent was removed at reduced pressure, and the crude material was purified on the MPLC (Biotage) eluted with 25% ethyl acetate-hexane to afford 63.0 mg (37.4%) of the product. $^1$H-NMR (DMSO-$d_6$) δ 10.20 (broad s, 1H), 7.54 (d, J=5.1 Hz, 1H), 7.47 (d, J=7.2 Hz, 1H); $R_f$=0.16 (25% ethyl acetate-hexane).

Step 3: Preparation of starting material: 3-amino-6-iodo-1-benzofuran-2-yl)(2,4-dichlorophenyl)methanone

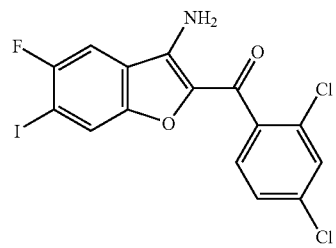

To a stirred solution of 5-fluoro-2-hydroxy-4-iodobenzonitrile (60 mg, 0.23 mmol) and 2,2',4'-trichloroacetophenone (76.5 mg, 0.34 mmol, 1.5 eq) anhydrous N,N-dimethylformamide (3.3 mL) was added potassium carbonate (47.3 mg, 0.34 mmol, 1.5 eq), and the orange reaction mixture was stirred at 80° C. for 16 h. The resulting dark wine color reaction was poured into ethyl acetate (100 mL) and water (50 mL). The ethyl acetate layer was washed with saturated aqueous ammonium chloride, water, and brine. The organic layer was then dried over sodium sulfate, filtered, and evaporated under reduced pressure. The crude product was purified on the MPLC (Biotage) eluted with 15% ethyl acetate-hexane to afford 41.0 mg (39.9%) of the product. $^1$H-NMR (Acetone-d6) δ 7.95 (d, J=4.5 Hz, 1H), 7.83 (d, J=7.5 Hz, 1H), 7.65 (d, J=2.1 Hz, 1H), 7.61 (s, 1H), 7.56 (d, J=1.8 Hz, 1H), 7.00 (broad s, 2H); LC-MS (ES MH$^+$=450, RT=3.78 min); $R_f$=0.39 (25% ethyl acetate-hexane).

Step 4: Preparation of the title compound: (3-Amino-5-fluoro-6-pyridin-3-yl-benzofuran-2-yl)-(2,4-dichloro-phenyl)-methanone

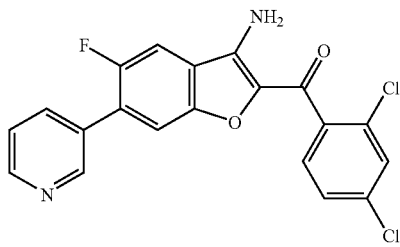

This compound was prepared from (3-amino-6-iodo-1-benzofuran-2-yl)(2,4-dichlorophenyl)methanone (38.0 mg, 0.08 mmol) in the manner described for [3-amino-6-(pyridin-3-yl)-1-benzofuran-2-yl](2,4-dichlorophenyl)methanone, affording 13.0 mg (38.4%) of the product. $^1$H-NMR (Acetone-d$_6$) δ 8.84 (t, J=1.8 Hz, 1H), 8.64 (dd, J=4.8 Hz, 1.5 Hz, 1H), 8.06 to 8.01 (m, 1H), 7.92 (d, J=10.2 Hz, 1H), 7.66 (d, J=1.8 Hz, 1H), 7.63 (s, 1H), 7.62 (d, J=6.0 Hz, 1H), 7.56 (dd, J=8.1 Hz, 2.1 Hz, 1H), 7.45 (ddd, J=7.2 Hz, 4.8 Hz, 0.9 Hz, 1H), 7.05 (broad s, 2H); LC-MS (ES MH$^+$=401, RT=2.66 min).

There may be slight variations in the above step 3 procedure with respect to the palladium catalyst used in the palladium-mediated coupling reactions, as illustrated by the following example:

Example 45b

Preparation of [3-Amino-6-(2-methyl-phenyl)-benzofuran-2-yl]-(2,4-dichloro-phenyl)-methanone

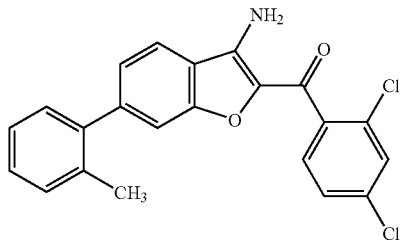

In a 7 mL vial with stirring was placed 75 mg (0.17 mmol, 1 eq) of (3-amino-6-iodo-1-benzofuran-2-yl)(2,4-dichlorophenyl)methanone in 2.5 mL of argon degassed DME. To this was added 10 mg (0.01 mmol, 0.05 eq) of Pd(PPh$_3$)$_4$ and the vial allowed to shake for 5 min. At this point, 29.1 mg (0.21 mmol, 1.2 eq) of 2-methylphenyl boronic acid and 0.43 mL (0.43 mmol, 2.5 eq) of 1 M Na$_2$CO$_3$ were added and the reaction allowed to shake at 80° C. overnight under argon. The volatiles were then removed and the residue purified via Prep TLC (25% EtOAc/Hex) to provide 42.9 mg (62%) of the desired product as a yellow solid. $^1$H-NMR (DMSO-d$_6$) δ 7.91 (d, 1H), 7.63 (d, 1H), 7.56 (d, 1H), 7.49 (dd, 1H), 7.34-7.24 (m, 8H), 2.28 (s, 3H), LC-MS (+esi MH$^+$=396.3, RT=3.86 min), TLC R$_f$=0.48 (25% EtOAc/Hex).

Example 46

Method C-2

Preparation of [3-amino-6-(2-methyl-3-pyridinyl)-1-benzofuran-2-yl](2,4-di-chlorophenyl)methanone

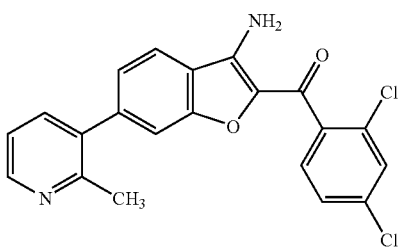

Step 1: Preparation of starting material: [3-amino-6-(4,4,5,5-tetramethyl-1,3,2-dioxaborolan-2-yl)-1-benzofuran-2-yl](2,4-dichlorophenyl)methanone

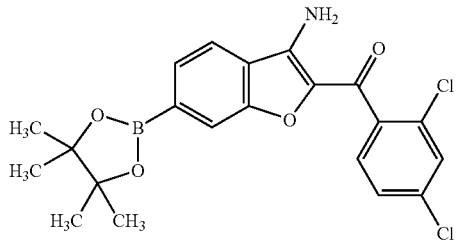

A solution of (3-amino-6-iodo-1-benzofuran-2-yl)(2,4-dichlorophenyl)methanone (225 mg, 0.52 mmol) in 1,4-dioxane (2.6 mL) was degassed with argon for 30 min. At this time, [1,1'-bis(diphenylphosphino)-ferrocene]dichloropalladium (II), complex with dichloromethane (1:1) (12.8 mg, 0.02 mmol, 0.03 eq) was added followed by triethylamine (0.22 mL, 1.56 mmol, 3.0 eq) and pinacolborane (0.13 mL, 0.89 mmol, 1.7 eq). The reaction was bubbled with argon for another 10 min and then heated to 80° C. overnight. The reaction was diluted with ethyl acetate, washed with water, brine, and dried over sodium sulfate. The solvent was removed at reduced pressure and purified on the MPLC (Biotage) eluted with 15% ethyl acetate-hexane to afford 154.5 mg (68.7%) of an orange foam. $^1$H-NMR (DMSO-d$_6$) δ 8.05 (d, J=7.8 Hz, 1H), 7.76 (d, J=2.4 Hz, 1H), 7.58 to 7.48 (m, 6H), 1.28 (s, 12H); LC-MS (ES MH$^+$=432/434, RT=3.97 min).

Step 2: Preparation of the tile compound: [3-amino-6-(2-methyl-3-pyridinyl)-1-benzofuran-2-yl](2,4-dichlorophenyl)methanone

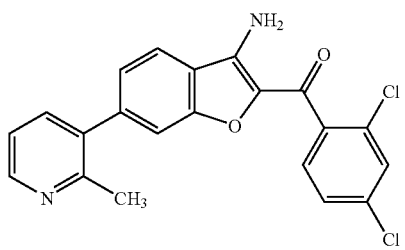

A solution of [3-amino-6-(4,4,5,5-tetramethyl-1,3,2-dioxaborolan-2-yl)-1-benzo-furan-2-yl](2,4-dichlorophenyl)methanone (65 mg, 0.15 mmol) in toluene (1.0 mL) and ethanol (1.0 mL) was degassed with argon for 30 min. At this time, 3-bromo-2-methylpyridine (33.6 mg, 0.20 mmol, 1.3 eq) was added followed by [1,1'-bis(diphenylphosphino)-ferrocene]dichloro-palladium(II), complex with dichloromethane (1:1) (12.3 mg, 0.02 mmol, 0.1 eq) and 2M aqueous $Na_2CO_3$ (0.38 mL). The reaction was bubbled with argon for another 15 min and then heated to 80° C. overnight. The reaction was diluted with ethyl acetate, washed with water, brine, and dried over magnesium sulfate. The solvent was removed at reduced pressure and purified on the MPLC (Biotage) eluted with 45 to 65% ethyl acetate-hexane to afford 23 mg (38.5%) of a yellow solid as the product. $^1$H-NMR (DMSO-$d_6$) δ 8.46 (dd, J=4.5, 1.5 Hz, 1H), 8.11 (d, J=8.4 Hz, 1H), 7.75 (d, J=2.1 Hz, 1H), 7.64 to 7.56 (m, 5H), 7.46 (s, 1H), 7.31 to 7.27 (m, 2H), 2.41 (s, 3H); LC-MS (ES $MH^+$=397/399, RT=2.34 min).

Additional compounds, illustrated in Table 2 below, were prepared in like manner as described above by choosing the appropriate starting materials that are readily available and/or the synthesis of which is taught herein, and using the process described above or other standard chemical processes known in the art.

TABLE 2

Examples of Formula (I) Compounds Synthesized using General Method C

| Example | Structure | $R_f$ (TLC solvent) Or RT (min)* | LC/MS ([M + H]+) | Synthesis of (III)** | Synthesis of (VI) or (VII)** | Synth. of (I) |
|---|---|---|---|---|---|---|
| 47 | 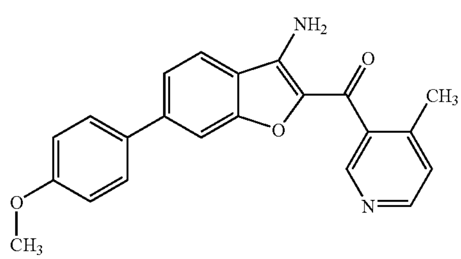 | $R_f$ = 0.213 [50% EtOAc/HEX] | 359.0 | A-3 | comm | C-1 |
| 48 | 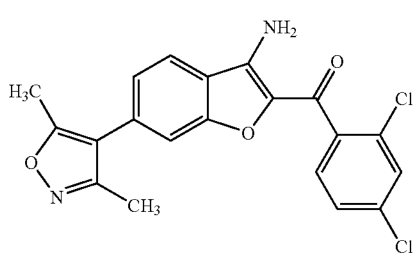 | $R_f$ = 0.14 [25% EtOAc/HEX] | 401/403 | comm | comm | C-1 |
| 49 | 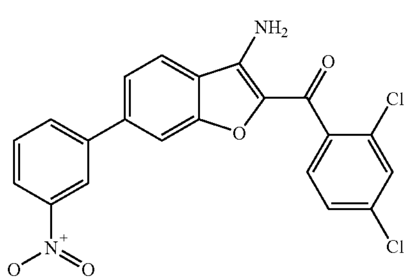 | $R_f$ = 0.14 {25% EtOAc/HEX) | 427/429 | comm | comm | C-1 |

TABLE 2-continued

Examples of Formula (I) Compounds Synthesized using General Method C

| Example | Structure | $R_f$ (TLC solvent) Or RT (min)* | LC/MS ([M + H]+) | Synthesis of (III)** | Synthesis of (VI) or (VII)** | Synth. of (I) |
|---|---|---|---|---|---|---|
| 50 | 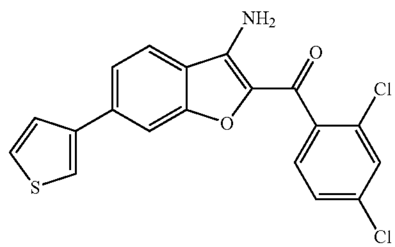 | $R_f$ = 0.35 (25% EtOAc/HEX) | 388/390 | comm | comm | C-1 |
| 51 | 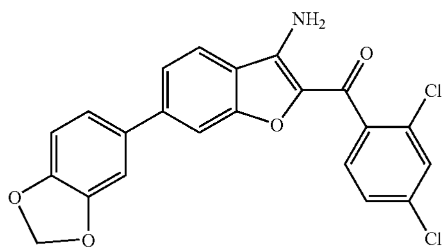 | $R_f$ = 0.245 (25% EtOAc/HEX) | 426.0 | comm | comm | C-1 |
| 52 | 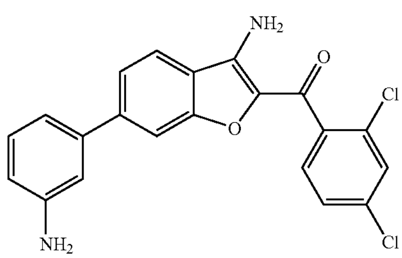 | $R_f$ = 0.34 (50% EtOAc/HEX) | 397.0 | comm | comm | C-1 |
| 53 | 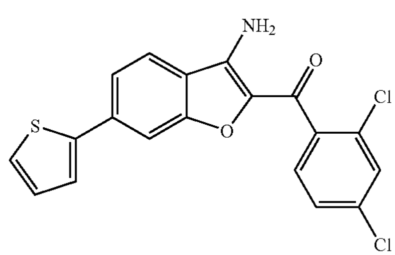 | $R_f$ = 0.25 (25% EtOAc/HEX) | 388/390 | comm | comm | C-1 |
| 54 | 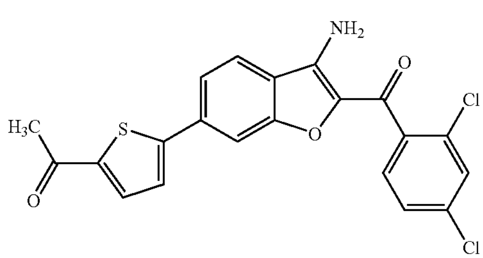 | $R_f$ = 0.13 (25% EtOAc/HEX) | 430/432 | comm | comm | C-1 |

TABLE 2-continued

Examples of Formula (I) Compounds Synthesized using General Method C

| Example | Structure | $R_f$ (TLC solvent) Or RT (min)* | LC/MS ([M + H]+) | Synthesis of (III)** | Synthesis of (VI) or (VII)** | Synth. of (I) |
|---|---|---|---|---|---|---|
| 55 | 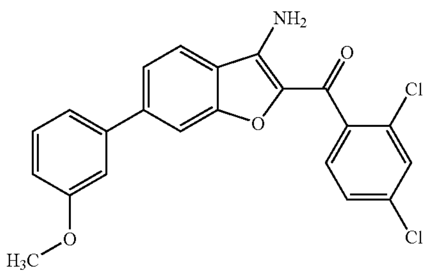 | $R_f$ = 0.30 (25% EtOAc/HEX) | 412/414 | comm | comm | C-1 |
| 56 | 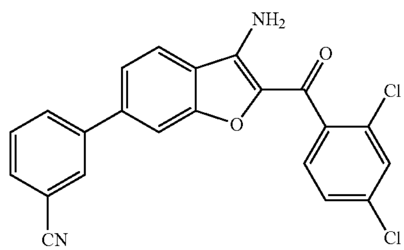 | $R_f$ = 0.08 (25% EtOAc/HEX) | 407/409 | comm | comm | C-1 |
| 57 | 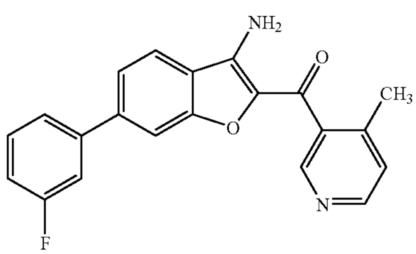 | $R_f$ = 0.10, HEX/EtOAc = 50/50 | 347.0 | A-3 | comm | C-1 |
| 58 | 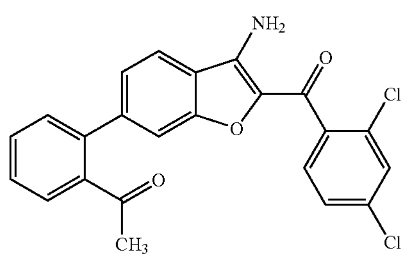 | $R_f$ = 0.21 (25% EtOAc/HEX) RT = 3.45 | 424.3 | comm | comm | C-1 |
| 59 | 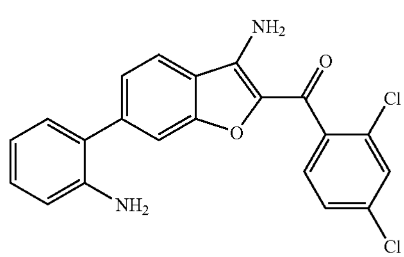 | $R_f$ = 0.15 (25% EtOAc/HEX) RT = 3.25 | 397.3 | comm | comm | C-1 |

TABLE 2-continued

Examples of Formula (I) Compounds Synthesized using General Method C

| Example | Structure | $R_f$ (TLC solvent) Or RT (min)* | LC/MS ([M + H]+) | Synthesis of (III)** | Synthesis of (VI) or (VII)** | Synth. of (I) |
|---|---|---|---|---|---|---|
| 60 | (3-amino-6-(2-methylphenyl)benzofuran-2-yl)(2,4-dichlorophenyl)methanone | $R_f$ = 0.48 (25% EtOAc/HEX) RT = 3.86 | 396.3 | comm | comm | C-1 |
| 61 | (3-amino-6-(2-methoxyphenyl)benzofuran-2-yl)(2,4-dichlorophenyl)methanone | $R_f$ = 0.35 (25% EtOAc/HEX) RT = 3.69 | 412.3 | comm | | C-1 |
| 62 | (3-amino-6-(3-fluorophenyl)benzofuran-2-yl)(2,4-dichlorophenyl)methanone | $R_f$ = 0.75 [50% EtOAc/HEX] | 400/402 | comm | comm | C-1 |
| 63 | (3-amino-6-(3-acetylphenyl)benzofuran-2-yl)(2,4-dichlorophenyl)methanone | $R_f$ = 0.65 [50% EtOAc/HEX] | 424/426 | comm | comm | C-1 |
| 64 | (3-amino-6-(3-(methylsulfonamido)phenyl)benzofuran-2-yl)(2,4-dichlorophenyl)methanone | $R_f$ = 0.35 [50% EtOAc/HEX] | 475/477 | comm | comm | C-1 |

TABLE 2-continued

Examples of Formula (I) Compounds Synthesized using General Method C

| Example | Structure | $R_f$(TLC solvent) Or RT (min)* | LC/MS ([M + H]+) | Synthesis of (III)** | Synthesis of (VI) or (VII)** | Synth. of (I) |
|---|---|---|---|---|---|---|
| 65 | 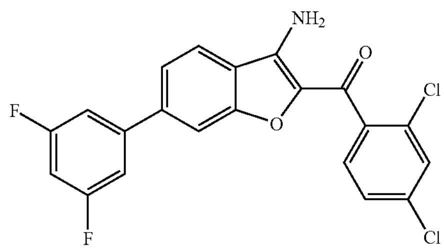 | $R_f$ = 0.75 [50% EtOAc/HEX] | 418/420 | comm | comm | C-1 |
| 66 | 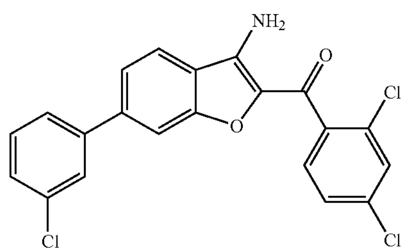 | $R_f$ = 0.75 [50% EtOAc/HEX] | 416/418 | comm | comm | C-1 |
| 67 | 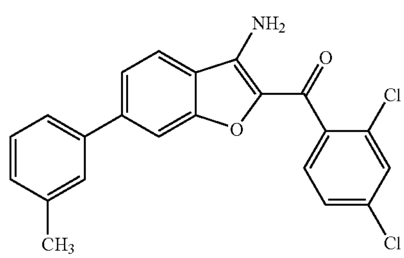 | $R_f$ = 0.75 [50% EtOAc/HEX] | 396/398 | comm | comm | C-1 |
| 68 | 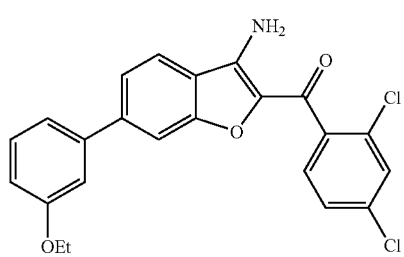 | $R_f$ = 0.75 [50% EtOAc/HEX] | 426/428 | comm | comm | C-1 |
| 69 | 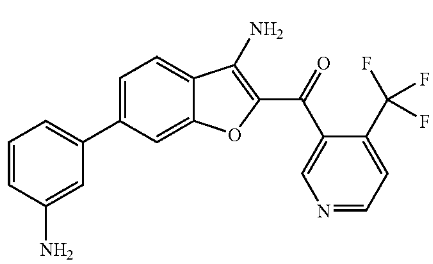 | $R_f$ = 0.27 (50% EtOAc/HEX) RT = 2.13 | 398.0 | A-4 | comm | C-1 |

TABLE 2-continued

Examples of Formula (I) Compounds Synthesized using General Method C

| Example | Structure | $R_f$ (TLC solvent) Or RT (min)* | LC/MS ([M + H]+) | Synthesis of (III)** | Synthesis of (VI) or (VII)** | Synth. of (I) |
|---|---|---|---|---|---|---|
| 70 | 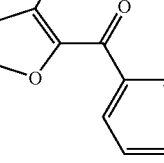 | $R_f$ = 0.33 [30% EtOAc/HEX] | 375.0 | comm | comm | C-1 |
| 71 | 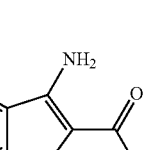 | $R_f$ = 0.25, HEX/EtOAc = 70/30 | 392.0 | comm | comm | C-1 |
| 72 | 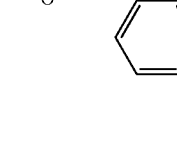 | $R_f$ = 0.33, HEX/EtOAc = 70/30 | 380.0 | comm | comm | C-1 |
| 73 | 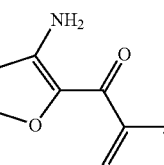 | $R_f$ = 0.40 [30% EtOAc/HEX] | 364.0 | comm | comm | C-1 |
| 74 | 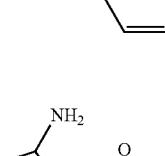 | $R_f$ = 0.46 (50% EtOAc/HEX) RT = 3.12 | 373.4 | A-4 | comm | C-1 |
| 75 | 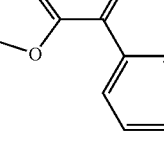 | $R_f$ = 0.51 (50% EtOAc/HEX) RT = 3.25 | 389.4 | A-4 | comm | C-1 |

TABLE 2-continued

Examples of Formula (I) Compounds Synthesized using General Method C

| Example | Structure | R$_f$ (TLC solvent) Or RT (min)* | LC/MS ([M + H]+) | Synthesis of (III)** | Synthesis of (VI) or (VII)** | Synth. of (I) |
|---|---|---|---|---|---|---|
| 76 | 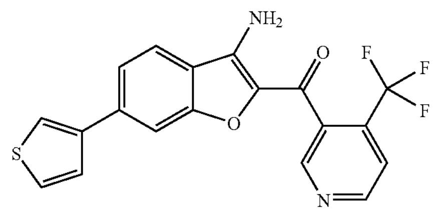 | R$_f$ = 0.46 (50% EtOAc/HEX) RT = 3.26 | 389.4 | A-4 | comm | C-1 |
| 77 | 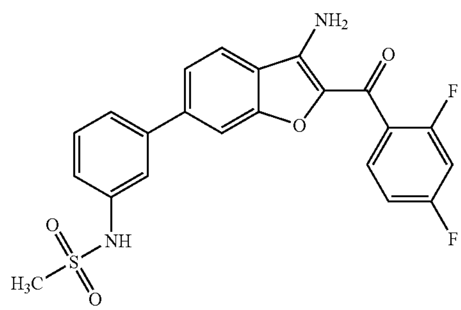 | R$_f$ = 0.15, HEX/EtOAc = 50/50 | 443.0 | comm | comm | C-1 |
| 78 | 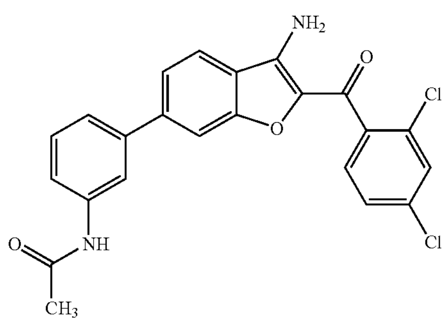 | R$_f$ = 0.14 [50% EtOAc/HEX] | 439/441 | comm | comm | C-1 |
| 79 | 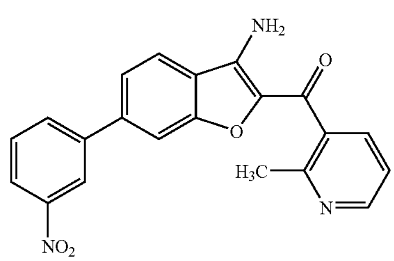 | R$_f$ = 0.43 (75% EtOAc/HEX) RT = 2.26 | 374.1 | A-4 | comm | C-1 |
| 80 | 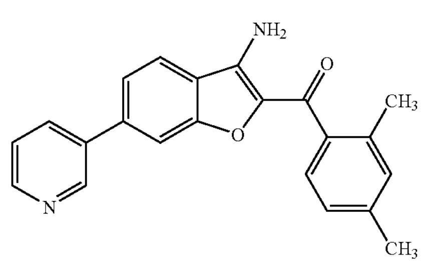 | R$_f$ = 0.10 [30% EtOAc/HEX] | 343.0 | comm | comm | C-1 |

TABLE 2-continued

Examples of Formula (I) Compounds Synthesized using General Method C

| Example | Structure | R_f (TLC solvent) Or RT (min)* | LC/MS ([M + H]+) | Synthesis of (III)** | Synthesis of (VI) or (VII)** | Synth. of (I) |
|---|---|---|---|---|---|---|
| 81 | 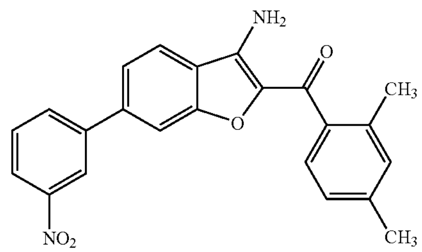 | R_f = 0.45 [30% EtOAc/HEX] | 387.0 | comm | comm | C-1 |
| 82 | 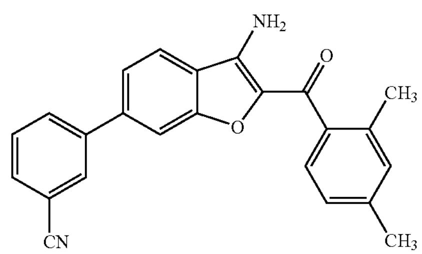 | R_f = 0.43 [30% EtOAc/HEX] | 367.0 | comm | comm | C-1 |
| 83 | 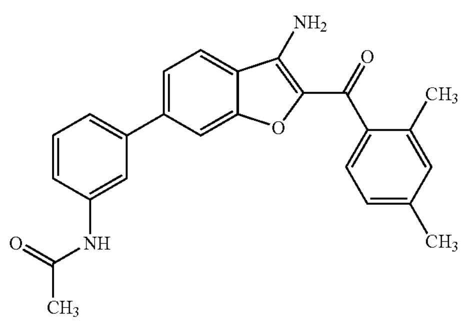 | R_f = 0.10 [30% EtOAc/HEX] | 399.0 | comm | comm | C-1 |
| 84 | 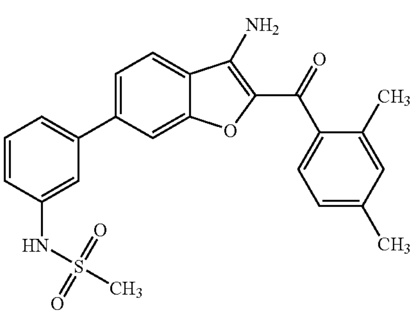 | R_f = 0.15 [30% EtOAc/HEX] | 435.0 | comm | comm | C-1 |
| 85 | 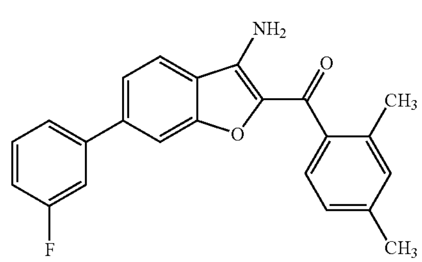 | R_f = 0.50 [30% EtOAc/HEX] | 360.0 | comm | comm | C-1 |

TABLE 2-continued

Examples of Formula (I) Compounds Synthesized using General Method C

| Example | Structure | R$_f$ (TLC solvent) Or RT (min)* | LC/MS ([M + H]+) | Synthesis of (III)** | Synthesis of (VI) or (VII)** | Synth. of (I) |
|---|---|---|---|---|---|---|
| 86 | 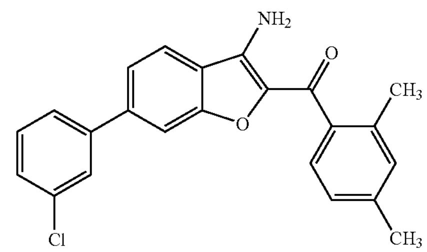 | R$_f$ = 0.50 [30% EtOAc/HEX] | 376.0 | comm | comm | C-1 |
| 87 | 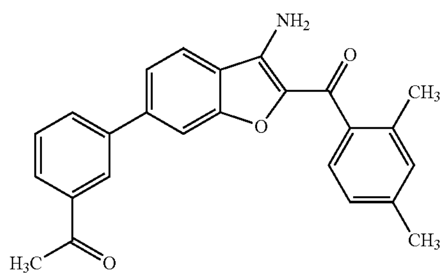 | R$_f$ = 0.35 [30% EtOAc/HEX] | 384.0 | comm | comm | C-1 |
| 88 | 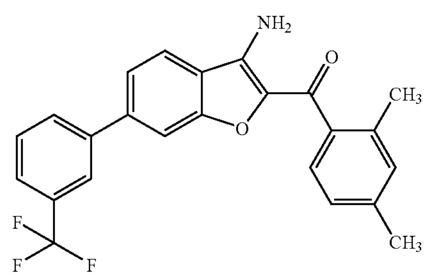 | R$_f$ = 0.46 [30% EtOAc/HEX] | 410.0 | comm | comm | C-1 |
| 89 | 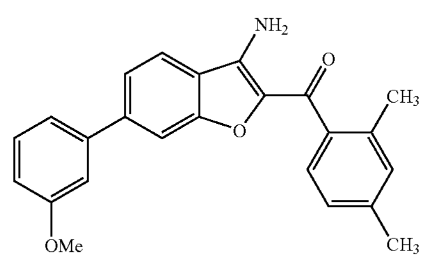 | R$_f$ = 0.40 [30% EtOAc/HEX] | 372.0 | comm | comm | C-1 |
| 90 | 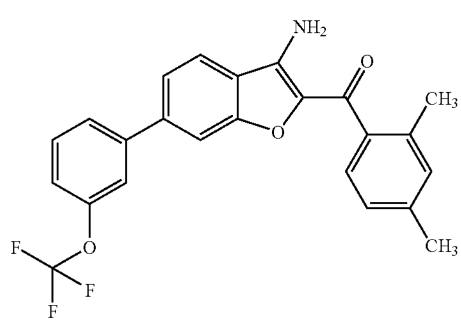 | R$_f$ = 0.45 [30% EtOAc/HEX] | 426.0 | comm | comm | C-1 |

TABLE 2-continued

Examples of Formula (I) Compounds Synthesized using General Method C

| Example | Structure | $R_f$(TLC solvent) Or RT (min)* | LC/MS ([M + H]+) | Synthesis of (III)** | Synthesis of (VI) or (VII)** | Synth. of (I) |
|---|---|---|---|---|---|---|
| 91 | 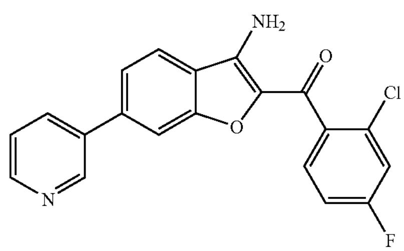 | $R_f$ = 0.05, HEX/EtOAc = 70/30 | 367.0 | A-4 | comm | C-1 |
| 92 | 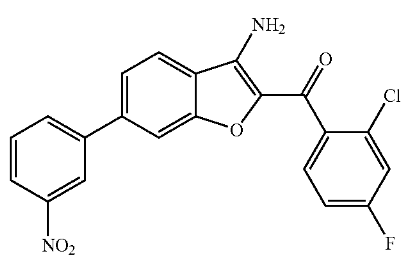 | $R_f$ = 0.28, HEX/ET)AC = 70/30 | 411.0 | A-4 | comm | C-1 |
| 93 | 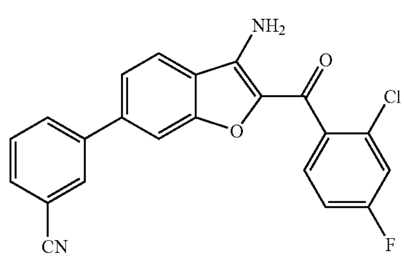 | $R_f$ = 0.28, HEX/EtOAc = 70/30 | 391.0 | A-4 | comm | C-1 |
| 94 | 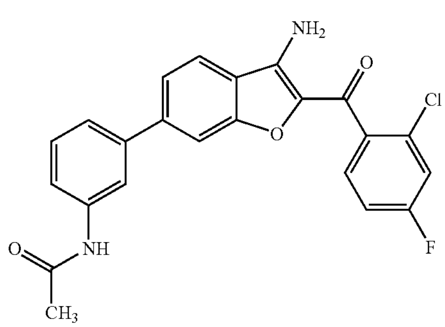 | $R_f$ = 0.10, HEX/EtOAc = 70/30 | 423.0 | A-4 | comm | C-1 |
| 95 | 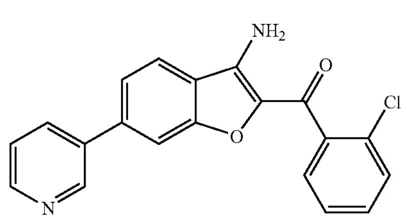 | $R_f$ = 0.08, HEX/EtOAc = 70/30 | 349.0 | A-2 | comm | C-1 |

TABLE 2-continued

Examples of Formula (I) Compounds Synthesized using General Method C

| Example | Structure | $R_f$ (TLC solvent) Or RT (min)* | LC/MS ([M + H]+) | Synthesis of (III)** | Synthesis of (VI) or (VII)** | Synth. of (I) |
|---|---|---|---|---|---|---|
| 96 | 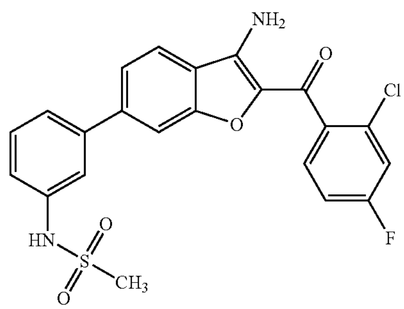 | $R_f$ = 0.05, HEX/EtOAc = 70/30 | 459.0 | A-4 | comm | C-1 |
| 97 | 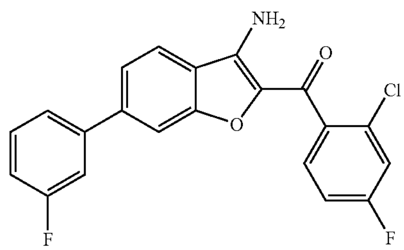 | $R_f$ = 0.30, HEX/EtOAc = 70/30 | 384.0 | A-4 | comm | C-1 |
| 98 | 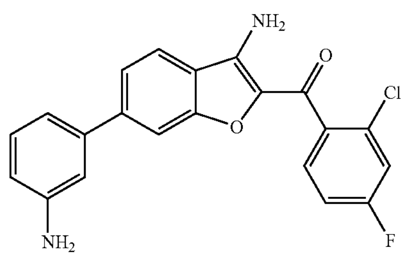 | $R_f$ = 0.08, HEX/EtOAc = 70/30 | 381.0 | A-4 | comm | C-1 |
| 99 | 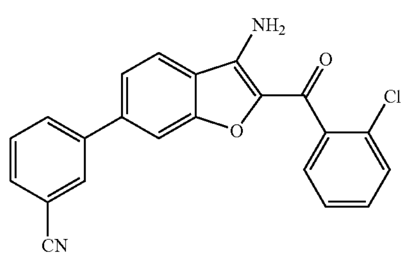 | $R_f$ = 0.30, HEX/EtOAc = 70/30 | 373.0 | A-2 | comm | C-1 |
| 100 | 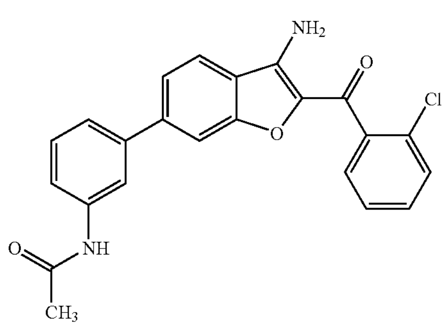 | $R_f$ = 0.05, HEX/EtOAc = 70/30 | 405.0 | A-2 | comm | C-1 |

TABLE 2-continued

Examples of Formula (I) Compounds Synthesized using General Method C

| Example | Structure | $R_f$ (TLC solvent) Or RT (min)* | LC/MS ([M + H]+) | Synthesis of (III)** | Synthesis of (VI) or (VII)** | Synth. of (I) |
|---|---|---|---|---|---|---|
| 101 | 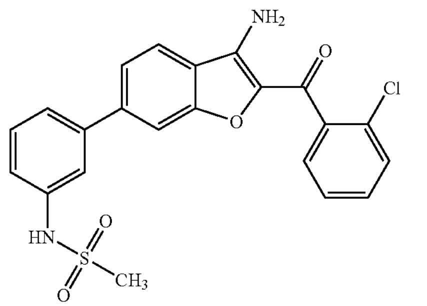 | $R_f$ = 0.05, HEX/EtOAc = 70/30 | 441.0 | A-2 | comm | C-1 |
| 102 | 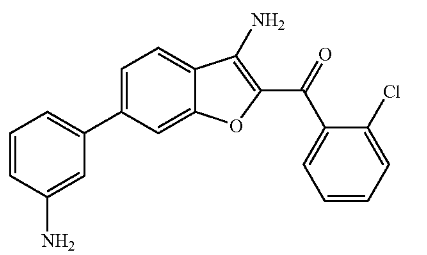 | $R_f$ = 0.10, HEX/EtOAc = 70/30 | 363.0 | A-2 | comm | C-1 |
| 103 | 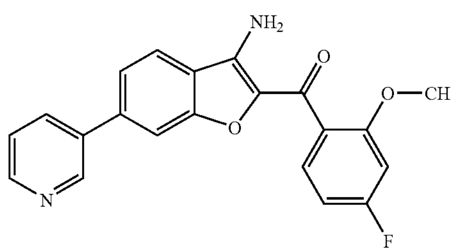 | $R_f$ = 0.14 (50% EtOAc/HEX) RT = 2.50 | 363.4 | A-2 | comm | C-1 |
| 104 | 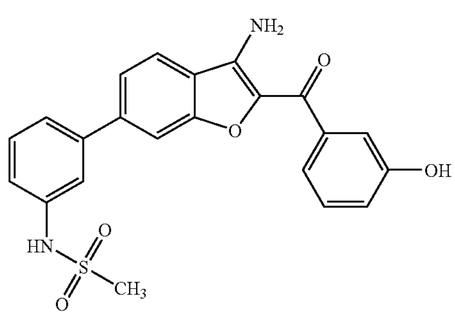 | $R_f$ = 0.10, HEX/EtOAc = 50/50 | 423.0 | A-6 | comm | C-1 |
| 105 | 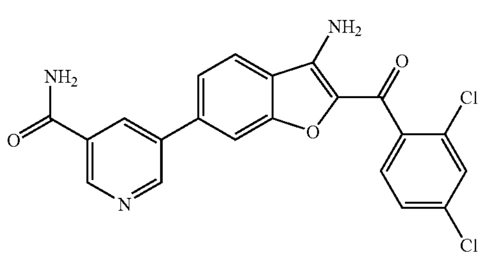 | $R_f$ = 0.11 (100% EtOAc) | 426.0 | comm | comm | C-2 |

TABLE 2-continued

Examples of Formula (I) Compounds Synthesized using General Method C

| Example | Structure | $R_f$(TLC solvent) Or RT (min)* | LC/MS ([M + H]+) | Synthesis of (III)** | Synthesis of (VI) or (VII)** | Synth. of (I) |
|---------|-----------|----------------------------------|------------------|----------------------|-------------------------------|---------------|
| 106 | 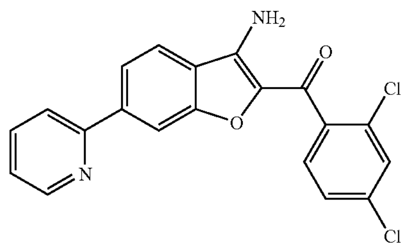 | $R_f$ = 0.10 (25% EtOAc/HEX) | 383.0 | comm | comm | C-2 |
| 107 | 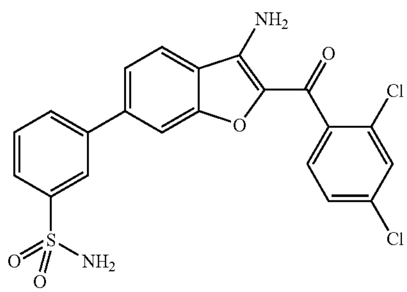 | $R_f$ = 0.15 (SILICA, EtOAc:HEX, 4:6) | 461.0 | comm | comm | C-2 |
| 108 | 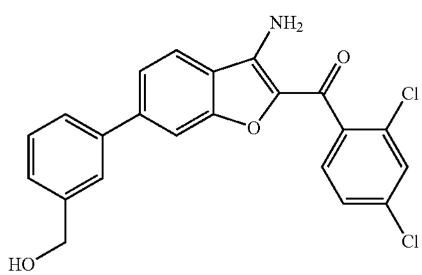 | $R_f$ = 0.13 (SILICA, EtOAc/HEX, 3/7) | 412.0 | comm | comm | C-2 |
| 109 | 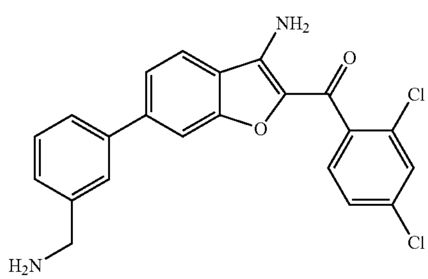 | $R_f$ = 0.11 (SILICA, MeOH/CH$_2$Cl$_2$, 6/94) | 435 | comm | comm | C-2 |
| 110 | 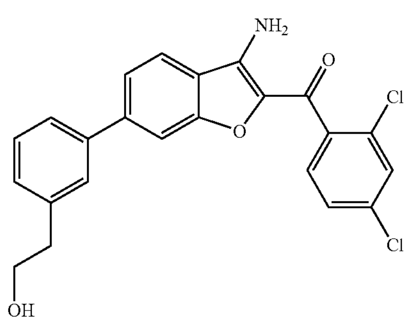 | $R_f$ = 0.09 (SILICA, EtOAc/HEX, 3/7) | 426.0 | comm | comm | C-2 |

TABLE 2-continued

Examples of Formula (I) Compounds Synthesized using General Method C

| Example | Structure | $R_f$(TLC solvent) Or RT (min)* | LC/MS ([M + H]+) | Synthesis of (III)** | Synthesis of (VI) or (VII)** | Synth. of (I) |
|---|---|---|---|---|---|---|
| 111 | 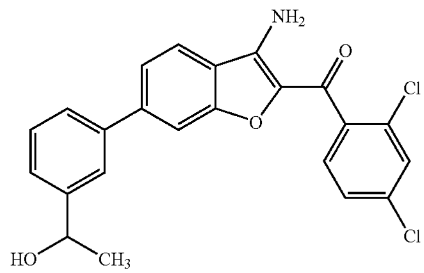 | $R_f$ = 0.26 (SILICA, EtOAc/HEX, 3/7) | 426.0 | comm | comm | C-2 |
| 112 | 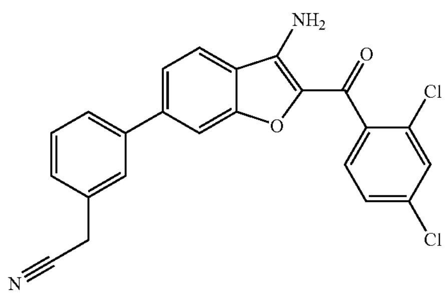 | $R_f$ = 0.23 (SILICA, EtOAc/HEX, 3/7) | 421.0 | comm | comm | C-2 |
| 113 | 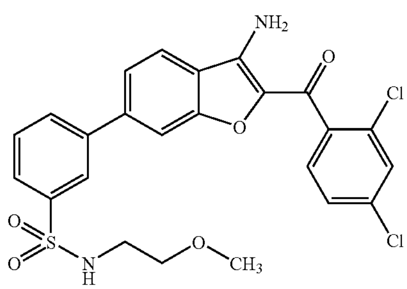 | $R_f$ = 0.29 (SILICA, EtOAc/HEX, 3/7) | 519.0 | comm | H-11 | C-2 |
| 114 | 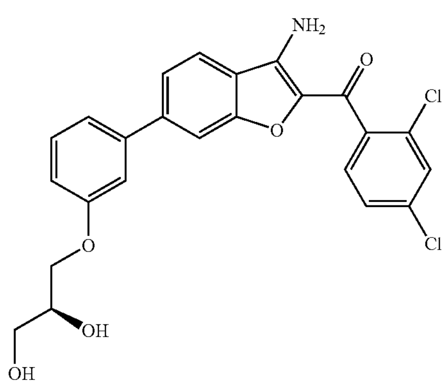 | $R_f$ = 0.55, 100% EtOAc | 472/474 | comm | H-6 | C-2 |

TABLE 2-continued

Examples of Formula (I) Compounds Synthesized using General Method C

| Example | Structure | R_f (TLC solvent) Or RT (min)* | LC/MS ([M + H]+) | Synthesis of (III)** | Synthesis of (VI) or (VII)** | Synth. of (I) |
|---|---|---|---|---|---|---|
| 115 | 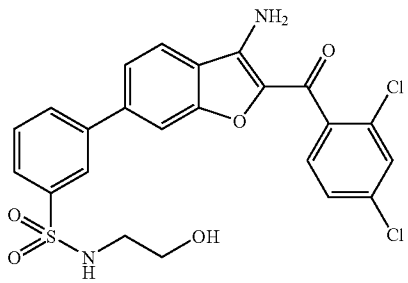 | R_f = 0.18 (SILICA, EtOAc/HEX, 6/4) | 505.0 | comm | H-11 | C-2 |
| 116 | 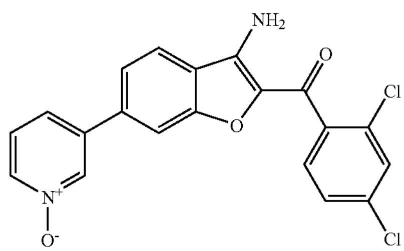 | R_f = 0.15 (10% MeOH/EtOAc) | 399.0 | comm | comm | C-2 |
| 117 | 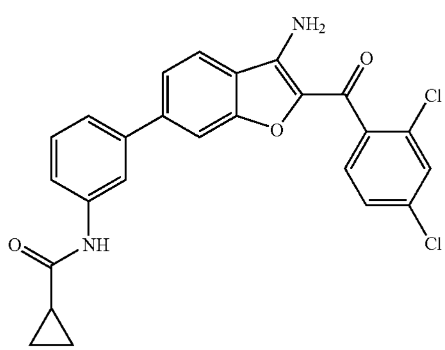 | R_f = 0.23, HEX/EtOAc = 70/30 | 465/467 | comm | H-10 | f |
| 118 | 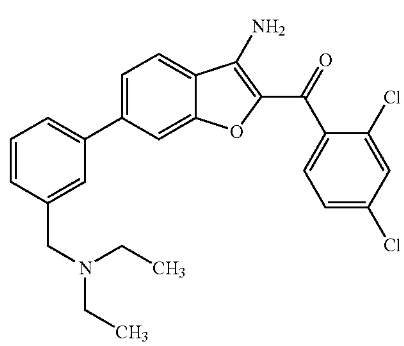 | R_f = 0.14 (SILICA, EtOAc/HEX, 1/1) | 467.0 | comm | H-12 | C-2 |
| 119 | 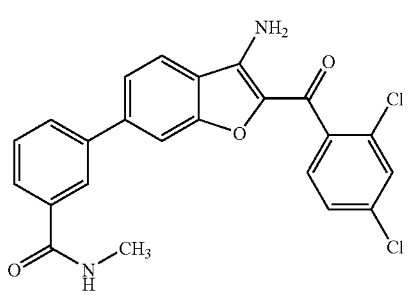 | R_f = 0.24 (SILICA, EtOAc/HEX, 3/2) | 439.0 | comm | H-13 | C-2 |

TABLE 2-continued

Examples of Formula (I) Compounds Synthesized using General Method C

| Example | Structure | $R_f$ (TLC solvent) Or RT (min)* | LC/MS ([M + H]+) | Synthesis of (III)** | Synthesis of (VI) or (VII)** | Synth. of (I) |
|---|---|---|---|---|---|---|
| 120 | 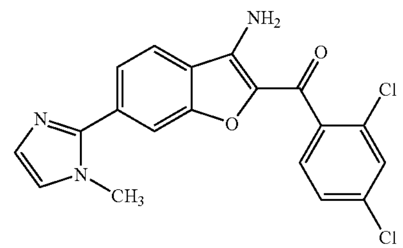 | $R_f$ = 0.33 (100% EtOAc) | 386.0 | comm | comm | C-2 |
| 121 | 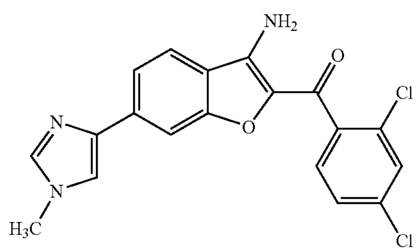 | $R_f$ = 0.32 (100% EtOAc) | 386.0 | comm | comm | C-2 |
| 122 | 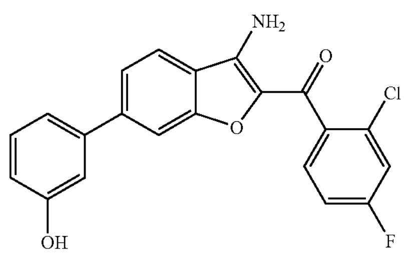 | $R_f$ = 0.12, HEX/EtOAc = 70/30 | 382.0 | A-4 | comm | C-2 |
| 123 | 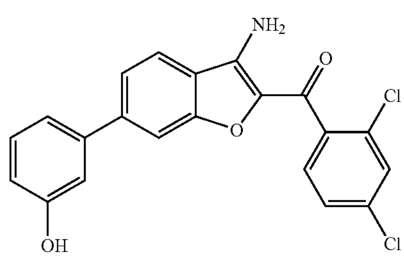 | $R_f$ = 0.14, HEX/EtOAc = 70/30 | 398/400 | comm | comm | C-2 |
| 124 | 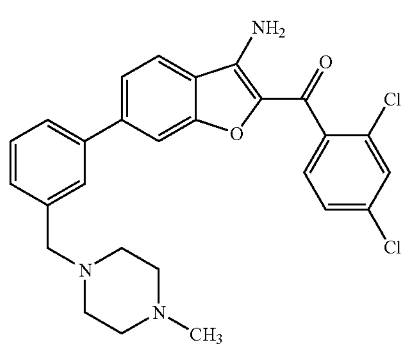 | $R_f$ = 0.30 (SILICA, MeOH/CH$_2$Cl$_2$, 8/92) | 494.0 | comm | H-12 | C-2 |

TABLE 2-continued

Examples of Formula (I) Compounds Synthesized using General Method C

| Example | Structure | $R_f$ (TLC solvent) Or RT (min)* | LC/MS ([M + H]+) | Synthesis of (III)** | Synthesis of (VI) or (VII)** | Synth. of (I) |
|---|---|---|---|---|---|---|
| 125 | 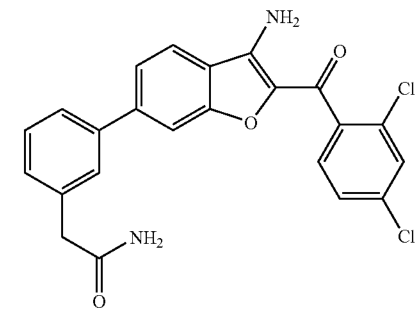 | $R_f$ = 0.17 (SILICA, EtOAc/HEX, 4/1) | 439.0 | comm | H-14 | C-2 |
| 126 | 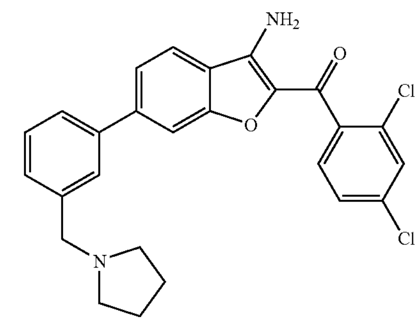 | $R_f$ = 0.07 (SILICA, EtOAc/HEX, 7/3) | 465.0 | comm | H-12 | C-2 |
| 127 | 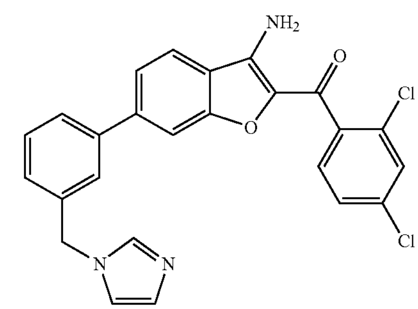 | $R_f$ = 0.30 (SILICA, MeOH/CH$_2$Cl$_2$, 6/94) | 462.0 | comm | H-12 | C-2 |
| 128 | 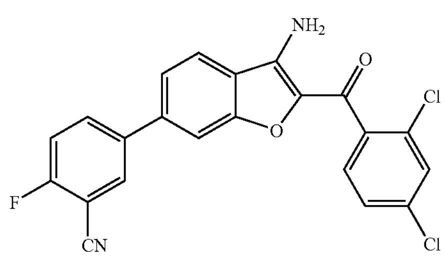 | $R_f$ = 0.32, HEX/EtOAc = 70/30 | 425/427 | comm | comm | C-2 |

TABLE 2-continued

Examples of Formula (I) Compounds Synthesized using General Method C

| Example | Structure | $R_f$ (TLC solvent) Or RT (min)* | LC/MS ([M + H]+) | Synthesis of (III)** | Synthesis of (VI) or (VII)** | Synth. of (I) |
|---|---|---|---|---|---|---|
| 129 | 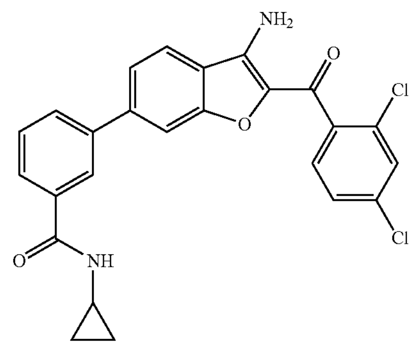 | $R_f$ = 0.13 (SILICA, EtOAc/HEX, 4/6) | 465.0 | comm | H-13 | C-2 |
| 130 | 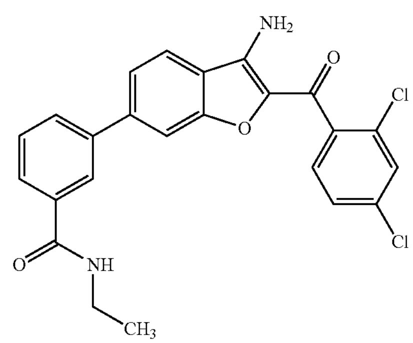 | $R_f$ = 0.24 (SILICA, EtOAc/HEX, 4/6) | 453.0 | comm | H-13 | C-2 |
| 131 | 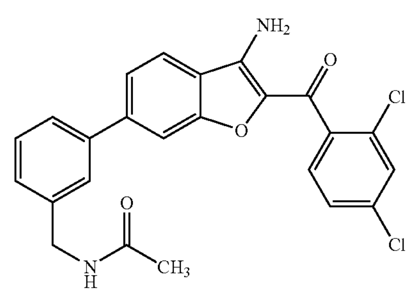 | $R_f$ = 0.10 (SILICA, EtOAc/HEX, 6/4) | 453.0 | comm | H-4 | C-2 |
| 132 | 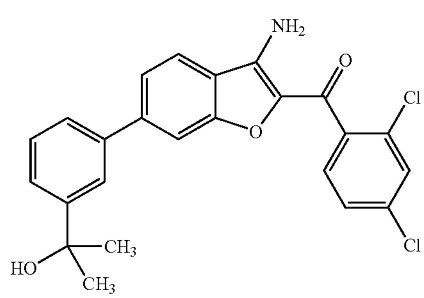 | $R_f$ = 0.35 (SILICA, EtOAc/HEX, 4/6) | 440.0 | comm | H-15 | C-2 |

TABLE 2-continued

Examples of Formula (I) Compounds Synthesized using General Method C

| Example | Structure | $R_f$ (TLC solvent) Or RT (min)* | LC/MS ([M + H]+) | Synthesis of (III)** | Synthesis of (VI) or (VII)** | Synth. of (I) |
|---|---|---|---|---|---|---|
| 133 | 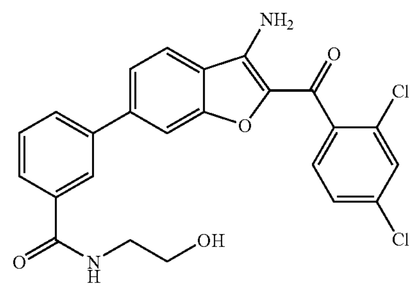 | $R_f$ = 0.17 (SILICA, EtOAc/HEX, 8/1) | 469.0 | comm | H-13 | C-2 |
| 134 | 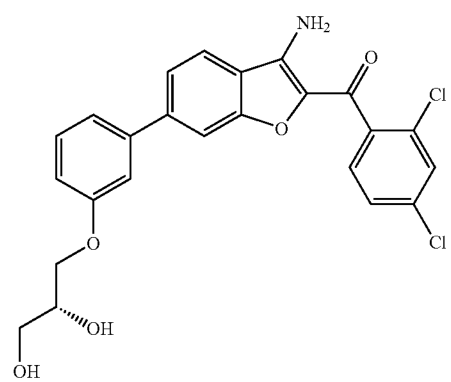 | $R_f$ = 0.55, 100% EtOAc | 472/474 | comm | H-6 | C-2 |
| 135 | 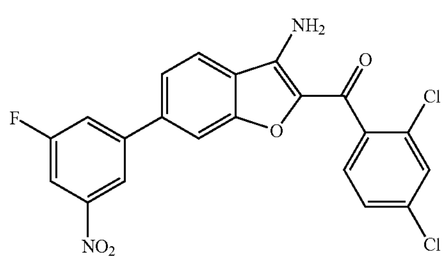 | $R_f$ = 0.45, HEX/EtOAc = 70/30 | 445/447 | comm | comm | C-2 |
| 136 | 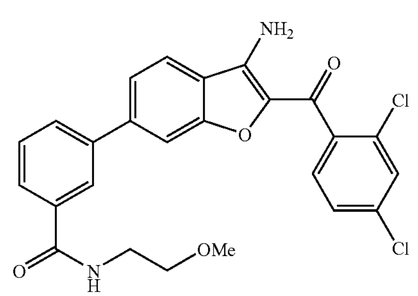 | $R_f$ = 0.14 (SILICA, EtOAc/HEX, 1/1) | 483.0 | comm | H-13 | C-2 |

TABLE 2-continued

Examples of Formula (I) Compounds Synthesized using General Method C

| Example | Structure | R$_f$(TLC solvent) Or RT (min)* | LC/MS ([M + H]+) | Synthesis of (III)** | Synthesis of (VI) or (VII)** | Synth. of (I) |
|---|---|---|---|---|---|---|
| 137 | 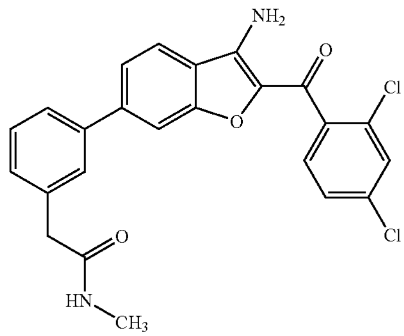 | R$_f$ = 0.17 (SILICA, EtOAc/HEX, 7/3) | 453.0 | comm | H-13 | C-2 |
| 138 | 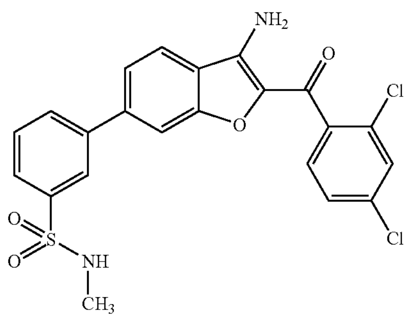 | R$_f$ = 0.10 (SILICA, EtOAc/HEX, 3/7) | 475.0 | comm | H-11 | C-2 |
| 139 | 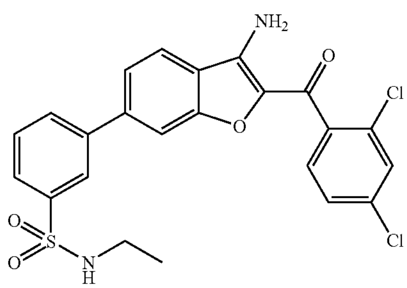 | R$_f$ = 0.15 (SILICA, EtOAc/HEX, 3/7) | 489.0 | comm | H-11 | C-2 |
| 140 | 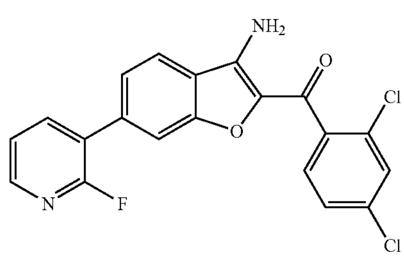 | R$_f$ = 0.23, HEX/EtOAc = 70/30 | 401/403 | comm | H-7 | C-2 |
| 141 | 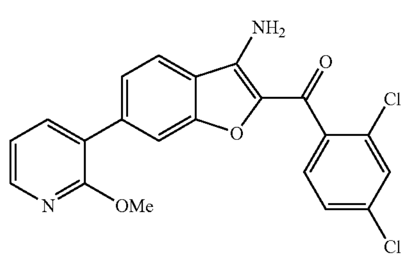 | R$_f$ = 0.30, HEX/EtOAc = 70/30 | 413.0 | comm | H-8 | C-2 |

TABLE 2-continued

Examples of Formula (I) Compounds Synthesized using General Method C

| Example | Structure | $R_f$ (TLC solvent) Or RT (min)* | LC/MS ([M + H]+) | Synthesis of (III)** | Synthesis of (VI) or (VII)** | Synth. of (I) |
|---|---|---|---|---|---|---|
| 142 | 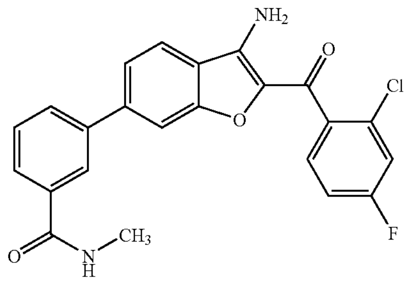 | $R_f$ = 0.26 (SILICA, EtOAc/HEX, 3/2) | 423.0 | A-2 | H-13 | C-2 |
| 143 | 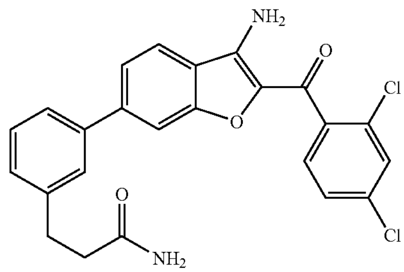 | $R_f$ = 0.12 (SILICA, EtOAc/HEX, 4/1) | 453.0 | Comm | H-14 | C-2 |
| 144 | 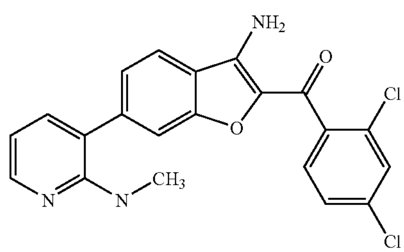 | $R_f$ = 0.33, HEX/EtOAc = 70/30 | 412/414 | comm | H-9 | C-2 |
| 145 | 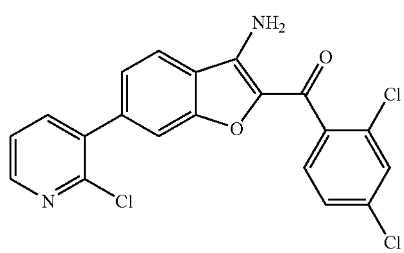 | $R_f$ = 0.29 (40% EtOAc/HEX) | 419.0 | comm | comm | C-2 |

Footnotes:
*The following are the LCMS conditions: HPLC - electrospray mass spectra (HPLC ES-MS) were obtained using a Gilson HPLC system equipped with two Gilson 306 pumps, a Gilson 215 Autosampler, a Gilson diode array detector, a YMC Pro C-18 column (2 × 23 mm, 120 A), and a Micromass LCZ single quadrupole mass spectrometer with z-spray electrospray ionization. Spectra were scanned from 120-1000 amu over 2 seconds. ELSD (Evaporative Light Scattering Detector) data was also acquired as an analog channel. Gradient elution was used with Buffer A as 2% acetonitrile in water with 0.02% TFA and Buffer B as 2% water in Acetonitrile with 0.02% TFA at 1.5 mL/min. Samples were eluted as follows: 90% A for 0.5 min ramped to 95% B over 3.5 min and held at 95% B for 0.5 min and then the column is brought back to initial conditions over 0.1 min. Total run time is 4.8 min.
** comm means commercially available.

General Method D: Preparation of Formula (I) Compounds Via 6-Bromo-Benzofuran Intermediates (VIII) and Boronates (V) and (VI).

Alternative methods for the preparation of compounds of formula (I), are illustrated in the Reaction Schemes for General Method D-1 and D-2 and the Reaction Scheme for General Method D-3, below.

In General methods D-1 and D-2, the common intermediate, [(3-Amino-6-bromo-benzofuran-2-yl)-(2,4-dichlorophenyl)-methanone (VIII) was used to prepare the 6-substituted benzofuran analogs with formula (I). Compound (VIII) was synthesized from 4-bromo-2-fluoro-benzonitrile using three simple chemical conversions (see experimental) as illustrated in the Reaction Scheme below. Palladium mediated coupling reactions between (VIII) and arylboronic acids or boronates (VI) afforded the desired compounds with the formula (I). Alternatively, 6-bromo-benzofuran (VIII) was converted to boronate (V), which was then used to prepare the desired compounds via palladium mediated coupling with arylhalides (VII).

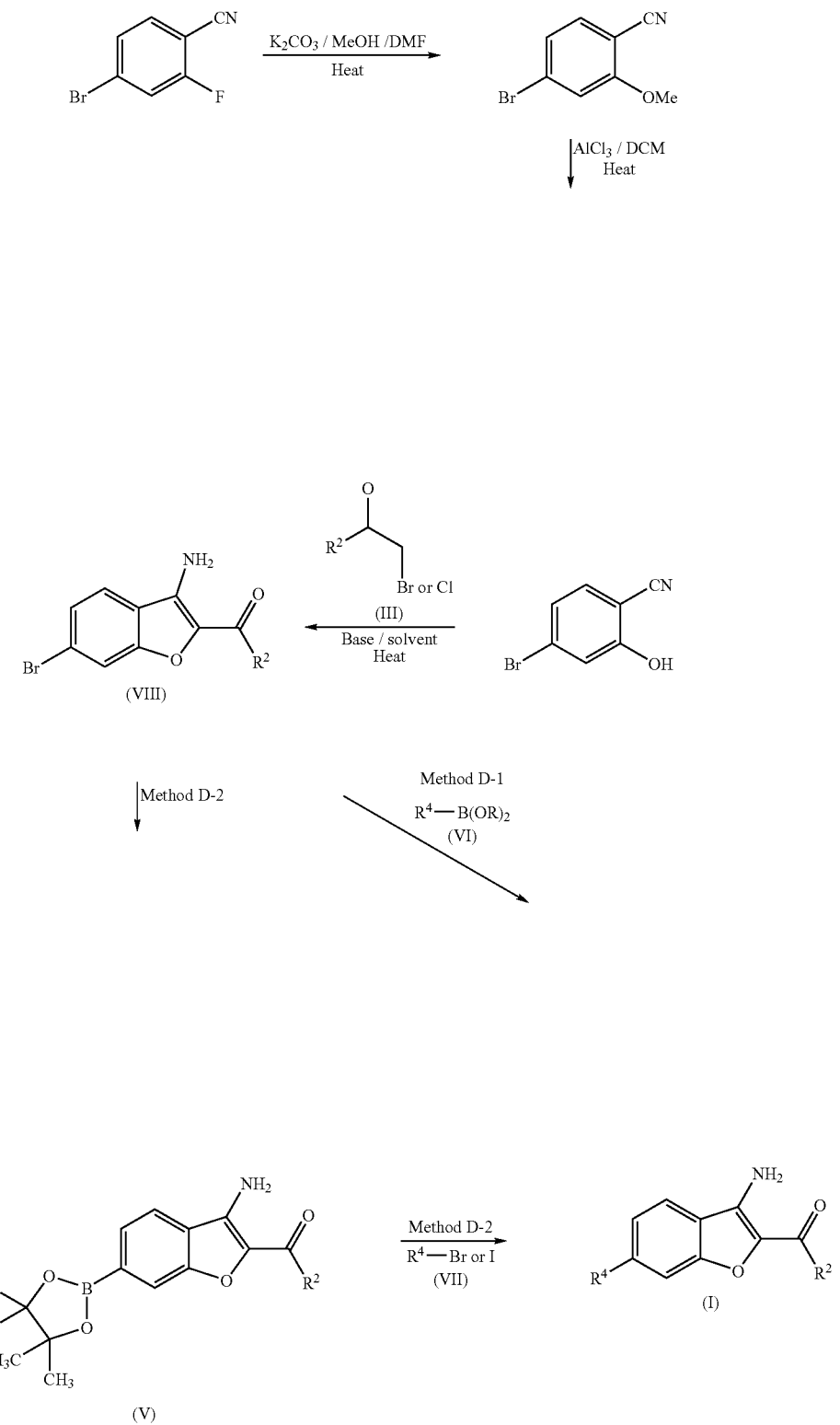
When $R^1$=low alkyl in formula (I), it was prepared according to General Method D-3. Intermediate (VIII) was acylated by the conventional methods followed by borane reduction to form intermediate (IX). Palladium mediated coupling reactions between (IX) and arylboronic acids or boronates (VI) afforded the desired compounds with the formula (I).

Reaction Scheme for General Method D-3

Method D-3

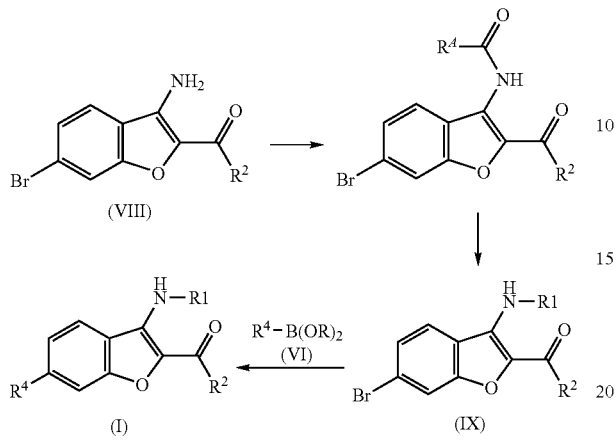

Example 146

Preparation of [(3-Amino-6-bromo-benzofuran-2-yl)-(2,4-dichloro-phenyl)-methanone

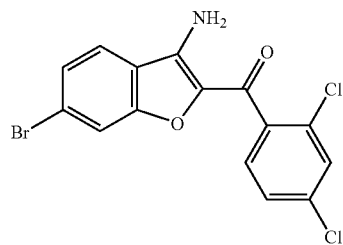

Step 1: Preparation of the starting material: 4-bromo-2-methoxy-benzonitrile

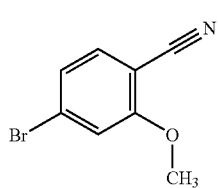

A mixture of 4-bromo-2-fluoro-benzonitrile (15.0 g, 75.0 mmol), methanol (30.4 mL, 350 mmol) and potassium carbonate (31.1 g, 225 mmol) in DMF (150 mL) was stirred under argon at 55° C. overnight. At this point TLC (100% methylene chloride) revealed no starting material, and the reaction mixture was poured into ether (300 mL) and water (150 mL). The layers were separated, and the organic layer was washed with water (150 mL) and brine (50 mL), dried over $Mg_2SO_4$, filtrated, and concentrated under reduced pressure, providing (15.2 g, 95.5%) of 4-bromo-2-methoxy-benzonitrile as a white solid. $^1$H-NMR (CDCl$_3$) δ7.41 (d, J=8.1 Hz, 1H), 7.16 (dd, J=8.1, 1.6 Hz, 1H), 7.13 (d, J=1.6 Hz, 1H), 3.93 (s, 3H); MS GC-MS (M$^+$=211; RT=6.15 min).

Step 2: Preparation of the intermediate: 4-bromo-2-hydroxy-benzonitrile

To a stirred solution of 4-bromo-2-methoxy-benzonitrile (4.60 g, 21.7 mmol) in methylene chloride (20 mL) was added aluminum chloride (14.5 g, 108 mmol). After stirring under an argon atmosphere for 10 min, more methylene chloride (30 mL) was added, and the mixture left to reflux under argon overnight. The reaction was then diluted with ethyl acetate, washed with water, brine, and dried over magnesium sulfate. The solvent was removed at reduced pressure, providing (4.09 g, 95.2%) of 4-bromo-2-hydroxy-benzonitrile as a slightly gray-colored product. $^1$H-NMR (CDCl$_3$) δ 7.35 (d, J=8.4 Hz, 1H), 7.19 (d, J=1.4 Hz, 1H), 7.14 (dd, J=8.4, 1.4 Hz, 1H), 6.15 (s, 1H); TLC R$_f$=0.78 (50% ethyl acetate-hexane).

Step 3: [(3-Amino-6-bromo-benzofuran-2-yl)-(2,4-dichloro-phenyl)-methanone

This compound was prepared from 4-bromo-2-hydroxy-benzonitrile (4.0 g, 20.3 mmol) in the manner described for [(3-amino-6-iodo-benzofuran-2-yl)-(2,4-dichloro-phenyl)-methanone (Example C-1 step 2), affording 6.1 g (78%) of [(3-amino-6-bromo-benzofuran-2-yl)-(2,4-dichloro-phenyl)-methanone as a yellow solid. $^1$H-NMR (DMSO-d$_6$) δ 7.96 (d, J=8.3 Hz, 1H), 7.74 (d, J=1.6 Hz, 1H), 7.72 (dd, J=1.7 Hz, 1.0 Hz, 1H), 7.56-7.49 (m, 4H), 7.44, (dd, J=8.5 Hz, 1.7 Hz, 1H). MS LC-MS (MH$^+$=386.1), LC MS RT: 3.68 min.

Example 147

Method D-1

Palladium mediated coupling between [(3-amino-6-bromo-benzofuran-2-yl)-(2,4-dichloro-phenyl)-methanone and arylboronic acids or boronates The exact procedures described in Example C-1 step 3 were followed except using [(3-amino-6-bromo-benzofuran-2-yl)-(2,4-dichloro-phenyl)-methanone (VIII) instead of [(3-amino-6-iodo-benzofuran-2-yl)-(2,4-dichloro-phenyl)-methanone (IV). Similar reaction also can be found in Example D-3 step 2.

Example 148

Method D-2

Preparation of [3-amino-6-(3-ethyl-phenyl)-benzofuran-2-yl]-(2,4-dichloro-phenyl)-methanone

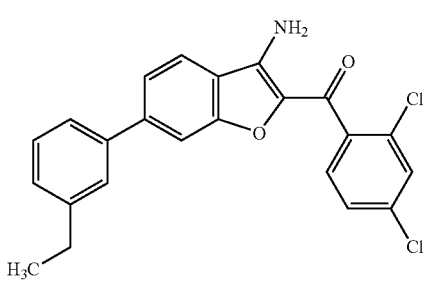

Step 1: Preparation of [3-Amino-6-(4,4,5,5-tetramethyl-[1,3,2]dioxaborolan-2-yl)-benzofuran-2-yl]-(2,4-dichloro-phenyl)-methanone

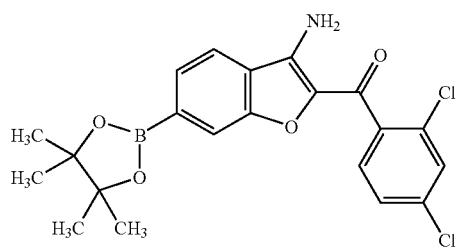

A mixture of [(3-amino-6-bromo-benzofuran-2-yl)-(2,4-dichloro-phenyl)-methanone (2.5 g, 6.5 mmol), potassium acetate (1.97 g, 19.5 mmol), bis(pinacolato)diboron (1.99 g, 7.79 mmol), in anhydrous DMSO was degassed under Ar for 30 min. Then Pd(dppf)$_2$Cl$_2$ (0.53 g, 0.65 mmol) was added, and the mixture degassed an additional 10 min. The reaction was then heated to 100° C. for 3.5 h. The reaction mixture was then poured into ethyl acetate and water. The organic layer was dried with magnesium sulfate, filtered and concentrated in vacuo. The crude residue was purified by silica-column eluting with 25% ethyl acetate-hexane and providing 1.2 g (43%) of 3-amino-6-(4,4,5,5-tetramethyl-[1,3,2]dioxaborolan-2-yl)-benzofuran-2-yl]-(2,4-dichloro-phenyl)-methanone as a brown solid. $^1$H-NMR (CDCl$_2$) δ 7.81 (s, 1H), 7.67 (d, J=7 Hz, 1H), 7.60 (d, J=7 Hz, 1H), 7.55-7.46 (m, 2H), 7.34, (dd, J=8.2 Hz, 2.0 Hz, 1H), 5.93 (bs, 2H), 1.33 (3, 12H). MS LC-MS (MH$^+$=432.3, 434.2), LC MS RT: 3.95 min.

Step 2: preparation of [3-amino-6-(3-ethyl-phenyl)-benzofuran-2-yl]-(2,4-dichloro-phenyl)-methanone

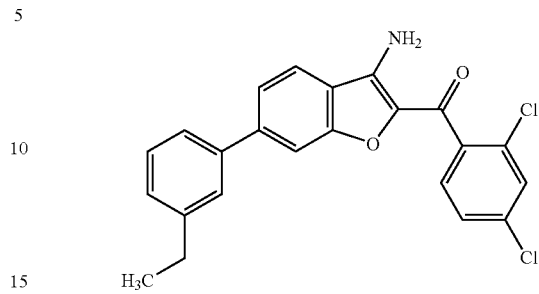

This compound was prepared from 1-bromo-3-ethyl-benzene (0.06 g, 0.30 mmol) using the manner described for [3-amino-6-(2-methyl-pyridydinyl)-1-benzofuran-2-yl](2,4-dichlorophenyl)methanone (Example C-2 step 2), affording 35.1 mg (37%) of [3-amino-6-(3-ethyl-phenyl)-benzofuran-2-yl]-(2,4-dichloro-phenyl)-methanone as a yellow solid. $^1$H-NMR (CDCl$_3$) δ 7.67 (dd, J=8.1 Hz, 1H), 7.56-7.53 (m, 1H), 7.55-7.49 (m, 3H), 7.45-7.34 (m, 4H), 7.25-7.21 (dm, J=4 Hz, 1H), 6.04 (bs, 2H), 2.72 (q, J=6 Hz, 2H), 1.28 (t, J=6 Hz, 3H). MS LC-MS (MH$^+$=410.3, 412.1), LC MS RT: 4.17 min.

Example 149

Method D-3

Preparation of N-{3-[2-(2,4-Dichloro-benzoyl)-3-methylamino-benzofuran-6-yl]-phenyl}-acetamide

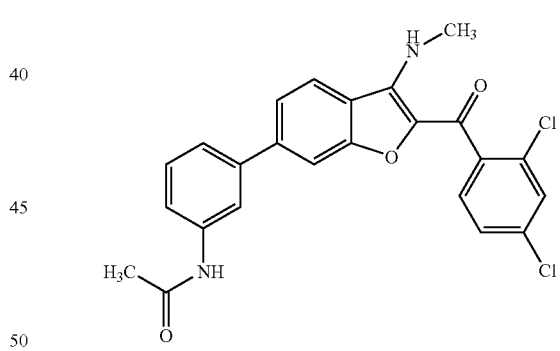

Step 1: Preparation of intermediate (6-Bromo-3-methylamino-benzofuran-2-yl)-(2,4-dichloro-phenyl)-methanone

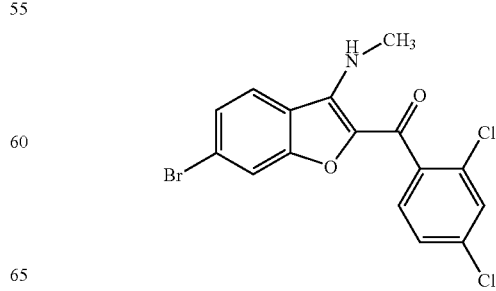

Acetic formic anhydride was made by the following method: Formic acid (1.5 mL, 39 mmol) was added dropwise into acetic anhydride (3 mL, 32 mmol) in a 250 mL flask in an ice bath, followed by gentle heating at 60° C. for 2 h. To the cooled flask of acetic formic anhydride (2.5 eq) was added the solution of (3-Amino-6-bromo-benzofuran-2-yl)-(2,4-dichloro-phenyl)-methanone prepared according to method D (5 g, 13 mmol, 1 eq) in 20 mL anhydrous THF. The reaction was refluxed at 70° C. for 40 h. Lots of solid precipitated while cooling the reaction. The white solid was filtered out, washed with THF and dried in vacuum oven. The product was thus formed was suspended in 40 mL THF and borane methyl sulfide (3 mL, 32 mmol, 2.5 eq) was added dropwise in an ice bath. The reaction mixture was stirred in the ice bath for 3 h, 10 mL methanol was added, stirred for another 30 min. The reaction mixture was evaporated to give green sticky material. White solid was formed while adding EtOAc to the mixture and the solid was removed by filtration. The filtrate was concentrated and the residue was purified by MPLC (Biotage). 700 mg (14%) of 6-Bromo-3-methylamino-benzofuran-2-yl)-(2,4-dichloro-phenyl)-methanone was obtained as a yellow solid. $^1$H-NMR (CDCl$_3$) δ 7.98 (broad, m, 1H), 7.82 (d, J=8 Hz, 1H), 7.52 (d, J=2 Hz, 1H), 7.48 (d, J=2 Hz, 1H), 7.44 (d, J=8 Hz, 1H), 7.35 (t, J=2 Hz, 1H), 7.33 (t, J=2 Hz, 1H), 2.40 (s, 3H). MS LC-MS MH$^+$=398/400/402; R$_f$=0.72, 50% EtOAc-HEX.

Step 2: Preparation of N-{3-[2-(2,4-Dichloro-benzoyl)-3-methylamino-benzofuran-6-yl]-phenyl}-acetamide A solution of (6-Bromo-3-methylamino-benzofuran-2-yl)-(2,4-dichloro-phenyl)-methanone (100 mg, 0.25 mmol) in ethylene glycol dimethyl ether (1 mL) was degassed with argon for 10 min. At this time degassed 3-acetamidobenzene boronic acid (49 mg, 0.28 mmol, 1.1 eq) in ethylene glycol dimethyl ether (4 mL) was added followed by [1,1'-bis(diphenylphosphino)-ferrocene]dichloro-palladium(II) complex (20 mg, 0.03 mmol, 0.1 eq) and 2M aqueous sodium carbonate (0.63 mL, 1.25 mmol, 5 eq). The reaction was bubbled with argon for 10 min and it was heated to 80° C. for 5 h. The reaction was diluted with EtOAc, washed with water and brine. The organic layer was dried in vacuo. Purification using preparative TLC gave 66.4 mg (59%) N-{3-[2-(2,4-dichloro-benzoyl)-3-methylamino-benzofuran-6-yl]-phenyl}-acetamide as a yellow solid. $^1$H-NMR (CDCl$_3$) δ 8.0 (broad, q, J=5.6 Hz, 1H), 7.91 (d, J=8.4 Hz, 1H), 7.63 (broad, s, 1H), 7.50 to 7.33 (m, 8H), 3.42 (d, J=5.6 Hz, 3H), 2.21 (s, 3H). MS LC-MS MH$^+$=453.2/455.2; R$_f$=0.13, 50% EtOAc-HEX.

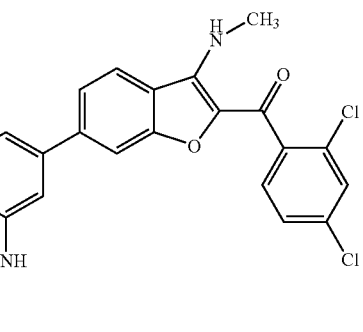

The other compounds in Table 3 can be prepared in like manner as described above by choosing the appropriate starting materials that are readily available and/or the synthesis of which is taught herein, and using the process described above or other standard chemical processes known in the art.

TABLE 3

Examples Synthesized using Method D

| Example | Structure | R$_f$ (TLC solvent) Or RT (min)* | LC/MS ([M + H]+) | Synthesis of (III)** | Synthesis of (VI) or (VII)** | Synth. of (I) |
|---|---|---|---|---|---|---|
| 150 | 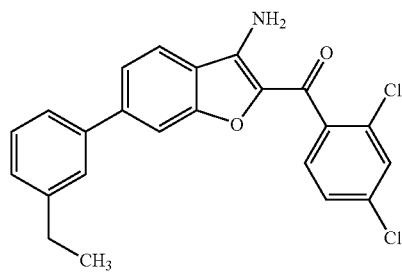 | RT = 4.17 | 410.3 | comm | comm | D-2 |

TABLE 3-continued

Examples Synthesized using Method D

| Example | Structure | R$_f$ (TLC solvent) Or RT (min)* | LC/MS ([M + H]+) | Synthesis of (III)** | Synthesis of (VI) or (VII)** | Synth. of (I) |
|---|---|---|---|---|---|---|
| 151 | 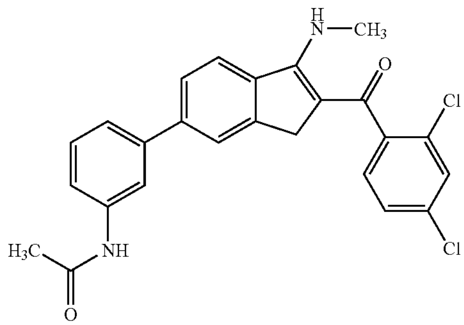 | R$_f$ = 0.13 @ 50/50 EtOAc/HEX | 453.2/455.2 | comm | comm | D-3 |
| 152 | 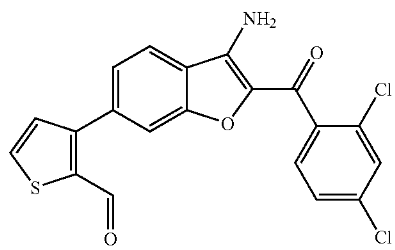 | RT = 3.94 | 416.1 | comm | comm | D-1 |
| 153 | 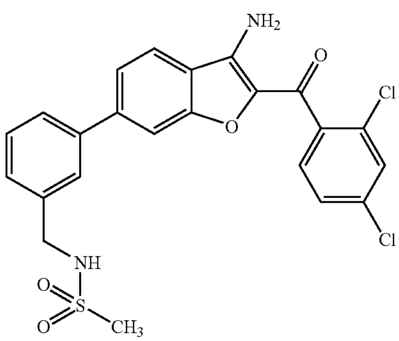 | R$_f$ = 0.09 (50% EtOAc/HEX) | 489.0 | comm | H-4 | D-2 |
| 154 | 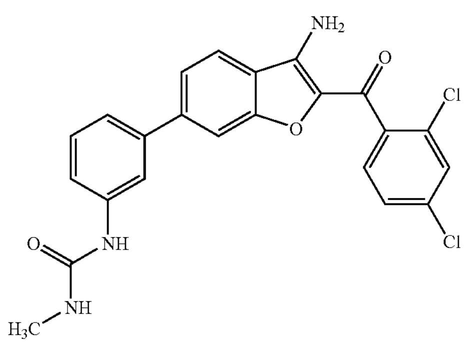 | R$_f$ = 0.19 (75% EtOAc/HEX) | 454.0 | comm | H-5 | D-2 |
| 155 | 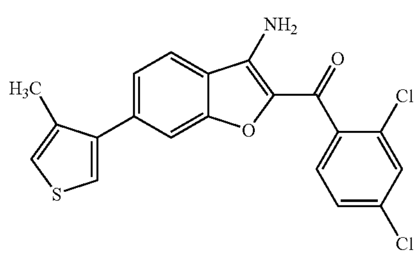 | RT = 4.33 | 402.1 | comm | comm | D-2 |

TABLE 3-continued

Examples Synthesized using Method D

| Example | Structure | $R_f$ (TLC solvent) Or RT (min)* | LC/MS ([M + H]+) | Synthesis of (III)** | Synthesis of (VI) or (VII)** | Synth. of (I) |
|---|---|---|---|---|---|---|
| 156 | 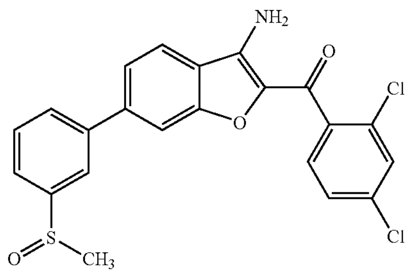 | RT = 3.54 | 444.1 | comm | H-3 | D-2 |
| 157 | 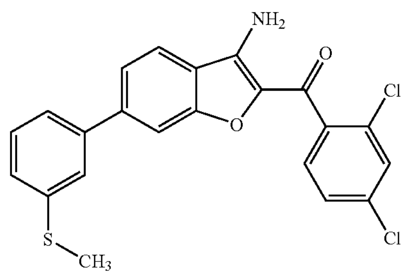 | RT = 4.41 | 428.2 | comm | comm | D-2 |
| 158 | 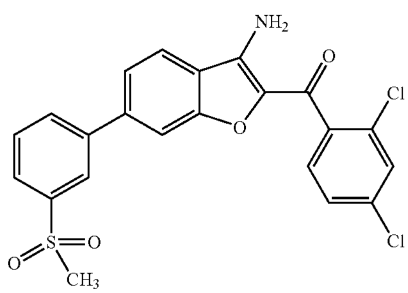 | RT = 3.78 | 460.1 | comm | H-3 | D-2 |
| 159 | 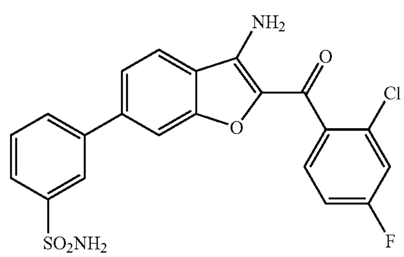 | RT = 2.96 | 445.1 | A-2 | comm | D-2 |
| 160 | 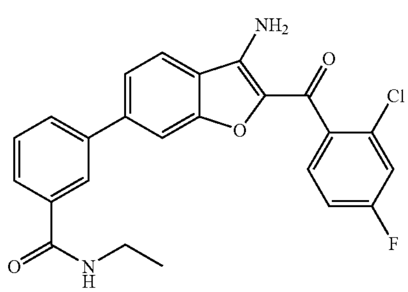 | RT = 3.58 | 437.2 | A-2 | comm | D-2 |

TABLE 3-continued

Examples Synthesized using Method D

| Example | Structure | R$_f$ (TLC solvent) Or RT (min)* | LC/MS ([M + H]+) | Synthesis of (III)** | Synthesis of (VI) or (VII)** | Synth. of (I) |
|---|---|---|---|---|---|---|
| 161 | 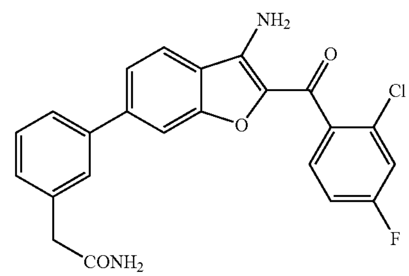 | RT = 2.89 | 423.2 | A-2 | comm | D-2 |
| 162 | 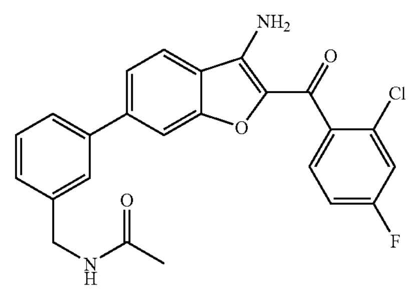 | RT = 3.00 | 437.2 | A-2 | comm | D-2 |
| 163 | 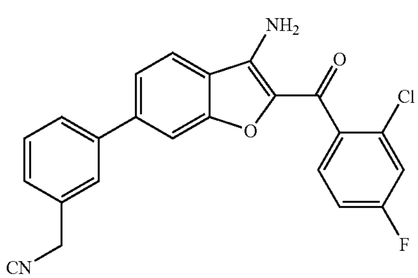 | RT = 3.82 | 405.2 | A-2 | comm | D-2 |
| 164 | 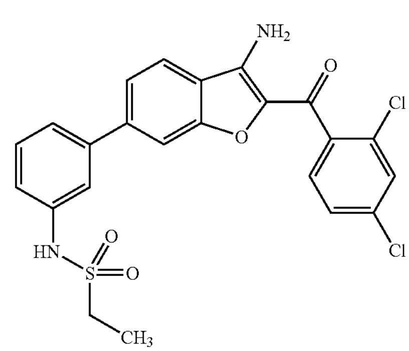 | R$_f$ = 0.21 (50% EtOAc/HEX); CONTAINS ~5% IMPURITY (BIS-ADDUCT D) | 489.0 | comm | H-4 | D-2 |

TABLE 3-continued

Examples Synthesized using Method D

| Example | Structure | $R_f$ (TLC solvent) Or RT (min)* | LC/MS ([M + H]+) | Synthesis of (III)** | Synthesis of (VI) or (VII)** | Synth. of (I) |
|---|---|---|---|---|---|---|
| 165 | 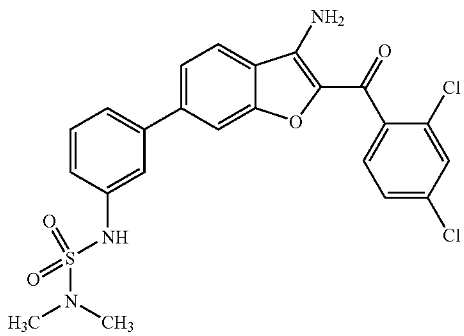 | $R_f$ = 0.3 (50% EtOAc/HEX); CONTAINS ~5% OF THE BIS-ADDUCT D. | 504.0 | comm | H-4 | D-2 |
| 166 | 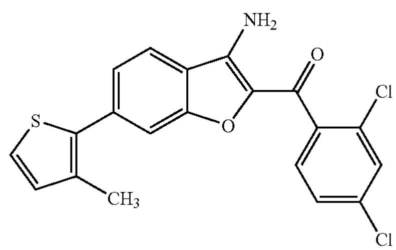 | RT = 4.37 | 402.1 | comm | comm | D-2 |
| 167 | 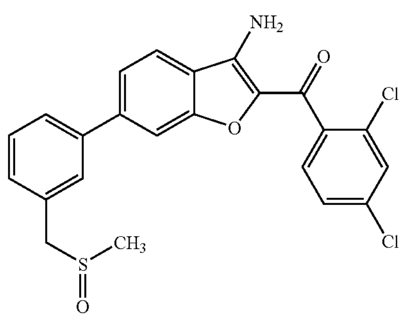 | RT = 3.06 | 458.0 | comm | H-1, H-3 | D-2 |
| 168 | 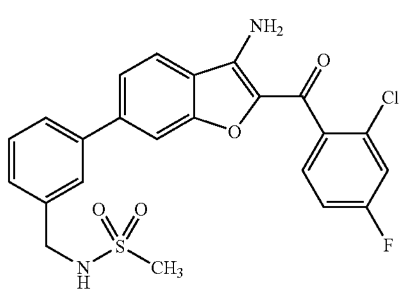 | $R_f$ = 0.08 (50% EtOAc/HEX) | 473.0 | A-2 | H-4 | D-2 |

TABLE 3-continued

Examples Synthesized using Method D

| Example | Structure | R_f (TLC solvent) Or RT (min)* | LC/MS ([M + H]+) | Synthesis of (III)** | Synthesis of (VI) or (VII)** | Synth. of (I) |
|---|---|---|---|---|---|---|
| 169 | 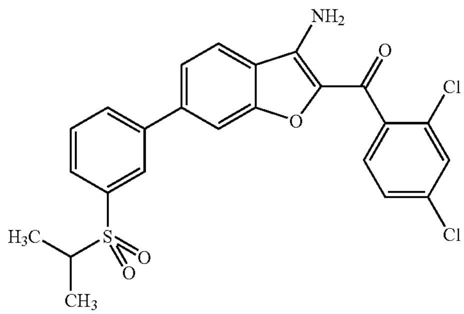 | RT = 4.03 | 488.2 | comm | H-2, H-3 | D-2 |
| 170 | 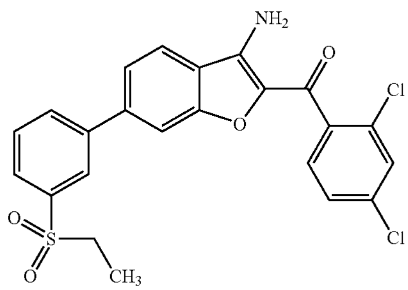 | RT = 3.91 | 474.1 | comm | H-2, H-3 | D-2 |
| 171 | 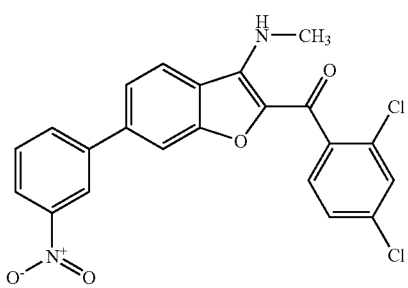 | R_f 0.59 @ 50/50 EtOAc/HEX | 441.1/443.1 | comm | comm | D-3 |
| 172 | 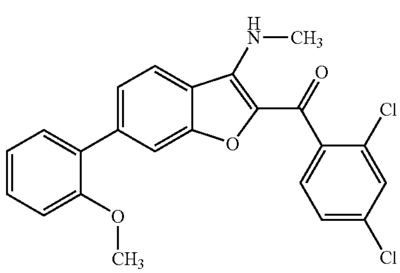 | R_f 0.70 @ 50/50 EtOAc/HEX | 426.2/428.2 | comm | comm | D-3 |
| 173 | 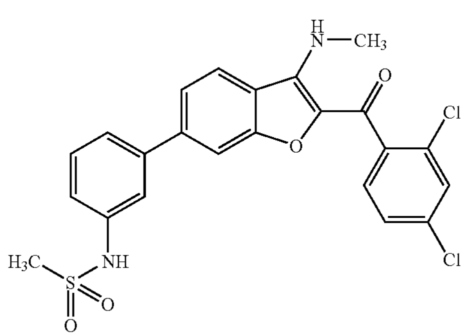 | R_f = 0.28 @ 50/50 EtOAc/HEX | 489.1/491.1 | comm | comm | D-3 |

TABLE 3-continued

Examples Synthesized using Method D

| Example | Structure | $R_f$ (TLC solvent) Or RT (min)* | LC/MS ([M + H]+) | Synthesis of (III)** | Synthesis of (VI) or (VII)** | Synth. of (I) |
|---|---|---|---|---|---|---|
| 174 | 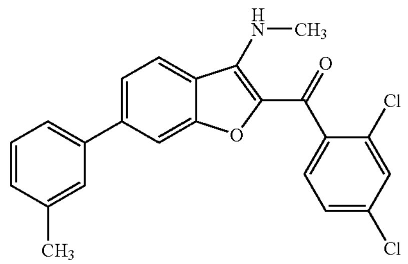 | $R_f$ = 0.76 @ 50/50 EtOAc/HEX | 410.1/412.1 | comm | comm | D-3 |
| 175 | 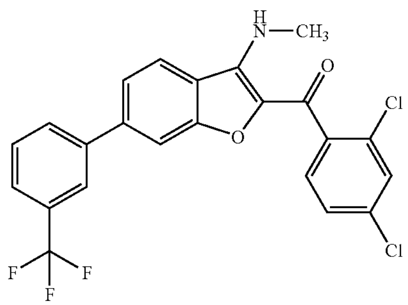 | $R_f$ = 0.74 @ 50/50 EtOAc/HEX | 464.1/466.1 | comm | comm | D-3 |

Footnotes:
*The following are the LCMS conditions: HPLC - elctrospray mass spectra (HPLC ES-MS) were obtained using a Gilson HPLC system equipped with two Gilson 306 pumps, a Gilson 215 Autosampler, a Gilson diode array detector, a YMC Pro C-18 column (2 × 23 mm, 120 A), and a Micromass LCZ single quadrupole mass spectrometer with z-spary electrospray ionization. Spectra were scanned from 120-1000 amu over 2 seconds. ELSD (Evaporative Light Scattering Detector) data was also acquired as an analog channel. Gradient elution was used with Buffer A as 2% acetonitrile in water with 0.02% TFA and Buffer B as 2% water in Acetonitrile with 0.02% TFA at 1.5 mL/min. Samples were eluted as follows: 90% A for 0.5 min ramped to 95% B over 3.5 min and held at 95% B for 0.5 min and then the column is brought back to initial conditions over 0.1 min. Total run time is 4.8 min.
**comm means commercially available.

General Method E: Preparation of N-Heterocyclic-Substituted Benzofurans

Methods E-1 to E-4 as illustrated in the General Reaction Schemes below, were the means used to prepare examples in this invention where $R^4$ substituents are attached to the benzofuran core through a nitrogen atom. Examples E-1 through E-4 describe various ways to prepare the properly substituted 2-cyano phenols (intermediates XI or XIII). The condensation of (XI) or (XIII) with 1-aryl-2-haloethanone (III) under basic conditions (such as cesium carbonate, potassium carbonate, sodium carbonate, DBU), in a solvent such as DMF, MeCN at temperatures between room temperature to 100° C. to give the desired products with formula (I).

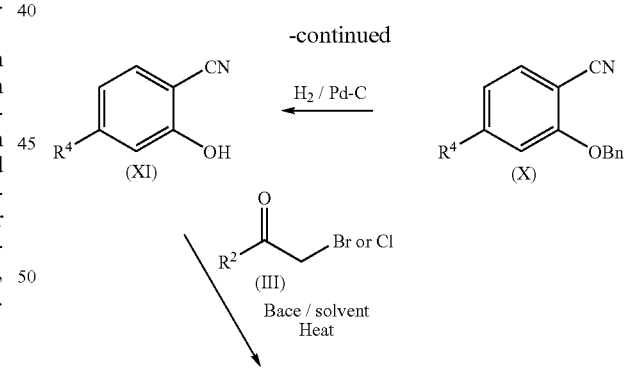

Reaction Scheme for General Methods E-1, E-2, E-4

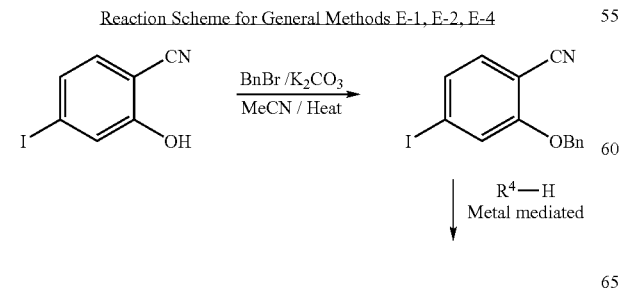

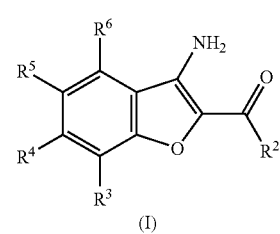

Reaction Scheme for General Method E-3

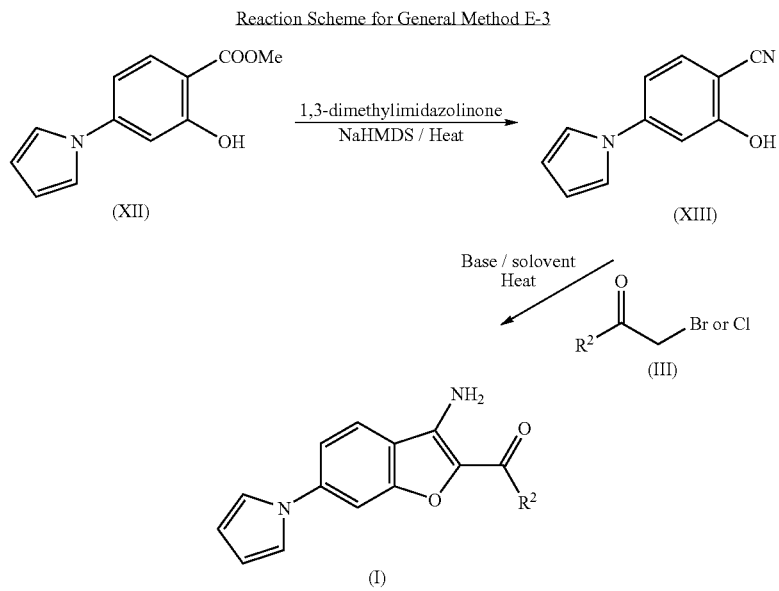

Example 176

Method E-1

Preparation of 3-[3-amino-2-(2,4-dichlorobenzoyl)-1-benzofuran-6-yl]-1,3-oxazolidin-2-one

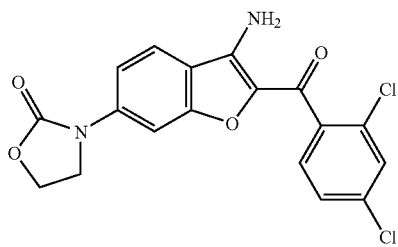

Step 1: Preparation of starting material: 2-(benzyloxy)-4-iodobenzonitrile

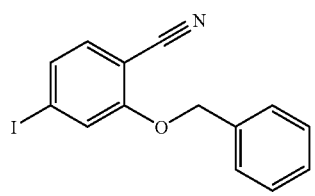

A mixture of 2-cyano-5-iodophenol (963 mg, 3.93 mmol), benzyl bromide (0.51 mL, 4.32 mmol, 1.1 eq), and potassium carbonate (597.5 mg, 4.32 mmol, 1.1 eq) in anhydrous acetonitrile was stirred at reflux under argon for 17 h. The resulting reaction was poured into ethyl acetate (300 mL) and water (150 mL). The ethyl acetate layer was washed with saturated aqueous ammonium chloride, water, and brine. The organic layer was then dried over sodium sulfate, filtered, and evaporated under reduced pressure to give a white solid (1.31 g, 99.5%). GC-MS (ES MH$^+$=336); TLC R$_f$=0.27 (5% ethyl acetate-hexane).

Step 2: Preparation of starting material: 2-(benzyloxy)-4-(2-oxo-1,3-oxazolidin-3-yl)benzonitrile

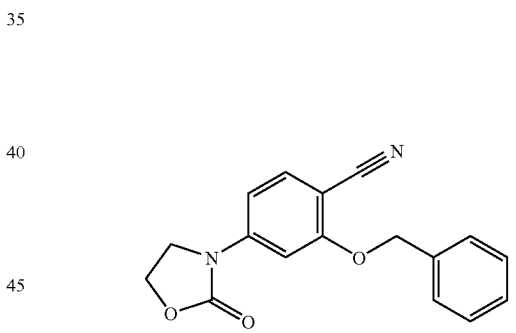

A solution of 2-(benzyloxy)-4-iodobenzonitrile (400 mg, 1.19 mmol), 2-oxazolidone (519.6 mg, 5.97 mmol, 5.0 eq), copper (140.3 mg, 2.21 mmol, 1.85 eq), potassium carbonate (240.8 mg, 1.74 mmol, 1.46 eq), and potassium iodide (309.1 mg, 1.86 mmol, 1.56 eq) in anhydrous N,N-dimethylformamide (4.8 mL) was stirred at 150° C. for 19 h. The resultant orange reaction was diluted with ethyl acetate, washed with water, brine, and dried over magnesium sulfate. The solvent was removed at reduced pressure and purified on the MPLC (Biotage) eluted with 4:1:5 v/v ethyl acetate-dichloromethane-hexane to afford 142.6 mg (40.6%) of the product. $^1$H-NMR (DMSO-d$_6$) δ 7.73 (d, J=9 Hz, 1H), 7.54 (d, J=2.4 Hz, 1H), 7.49 to 7.34 (m, 5H), 7.25 (dd, J=8.7 Hz, 2.1 Hz, 1H), 5.27 (s, 2H), 4.45 (t, J=8.1 Hz, 2H), 4.07 (t, J=8.7 Hz, 2H); LC-MS (ES MH$^+$=294.9, RT=2.82 min).

Step 3: Preparation of 2-hydroxy-4-(2-oxo-1,3-oxazolidin-3-yl)benzonitrile

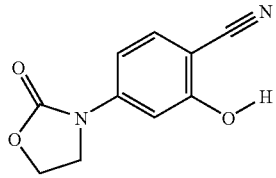

To a dry flask charged with 10% Pd/C (14.0 mg, 0.05 mmol, 0.1 eq) was added a solution of 2-(benzyloxy)-4-(2-oxo-1,3-oxazolidin-3-yl)benzonitrile (140 mg, 0.48 mmol) in 1:1 v/v tetrahydrofuran-ethanol (16 mL). The reaction mixture was hydrogenated under an atmosphere of hydrogen supplied by an attached balloon for 16 h. The reaction was filtered through a pad of celite, and the filtrate was concentrated to afford 90.5 mg (93%) of a white solid. $^1$H-NMR (DMSO-$d_6$) δ 7.53 (d, J=8.4 Hz, 1H), 7.31 (s, 1H), 6.95 (dd, J=8.7 Hz, 1.8 Hz, 1H), 4.40 (t, J=8.7 Hz, 2H), 4.00 (t, J=8.4 Hz, 2H), 3.25 (broad s, 1H); TLC $R_f$=0.14 (75% ethyl acetate-hexane)

Step 4: Preparation of 3-[3-amino-2-(2,4-dichlorobenzoyl)-1-benzofuran-6-yl]-1,3-oxazolidin-2-one

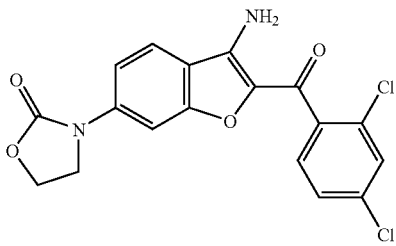

To a stirred solution of 2-hydroxy-4-(2-oxo-1,3-oxazolidin-3-yl)benzonitrile (62 mg, 0.30 mmol) and 2,2',4'-trichloroacetophenone (101.8 mg, 0.46 mmol, 1.5 eq) in anhydrous N,N-dimethylformamide (3.0 mL) was added potassium carbonate (63.0 mg, 0.46 mmol, 1.5 eq), and the orange reaction mixture was stirred at 80° C. for 16 h. The resulting dark wine color reaction was poured into ethyl acetate (100 mL) and water (50 mL). The ethyl acetate layer was washed with saturated aqueous ammonium chloride, water, and brine. The organic layer was then dried over sodium sulfate, filtered, and evaporated under reduced pressure. The crude product was purified on the MPLC (Biotage) eluted with 60% ethyl acetate-hexane. Crystallization from dichloromethane-hexane afforded the benzofuran as an orange solid (43 mg, 36.2%). $^1$H-NMR (DMSO-$d_6$) δ 8.01 (d, J=6.0 Hz, 1H), 7.93 (s, 1H), 7.73 (dd, J=1.8, 0.9 Hz, 1H), 7.63 (dd, J=8.7, 1.8 Hz, 1H), 7.55 to 7.52 (m, 4H), 4.43 (t, J=8.7 Hz, 2H), 4.07 (t, J=8.7 Hz, 2H); LC-MS (ES MH$^+$=391/393, RT=3.00 min.).

Example 177

Method E-2

Preparation of (3-Amino-6-morpholin-4-yl-benzofuran-2-yl)-(2,4-dichloro-phenyl)-methanone

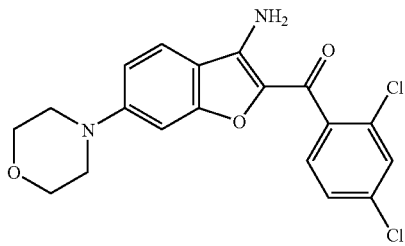

Step 1: 2-(benzyloxy)-4-(morpholin-4-yl)benzonitrile

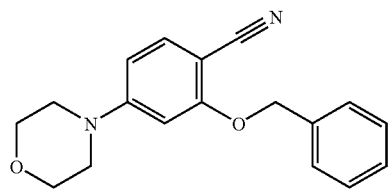

A solution of 2-(benzyloxy)-4-iodobenzonitrile (350 mg, 1.04 mmol), tris(dibenzylideneacetone)dipalladium(0) (95.6 mg, 0.10 mmol, 0.1 eq), tritolyl phosphate (95.3 mg, 0.31 mmol, 0.3 eq), potassium tent-butoxide (281.0 mg, 2.92 mmol, 2.8 eq) in anhydrous dioxane (5.2 mL) was degassed under argon. After 20 min, morpholine (0.22 mL, 2.51 mmol, 2.4 eq) was added, and the reaction mixture was stirred at 90° C. for 4 h. The reaction was diluted with ethyl acetate, washed with water, brine, and dried over magnesium sulfate. The solvent was removed at reduced pressure, and the crude material was purified on the MPLC (Biotage) eluted with 30% ethyl acetate/hexane to afford 220.5 mg (71.7%) of the product. $^1$H-NMR (DMSO-$d_6$) δ 7.48 to 7.33 (m, 6H), 6.70 (d, J=2.1 Hz, 1H), 6.59 (dd, J=8.7 Hz, 2.1 Hz, 1H), 5.24 (s, 2H), 3.70 (t, J=5.1 Hz, 4H), 3.29 (t, J=5.1 Hz, 4H); LC-MS (ES MH$^+$=295, RT=3.09 min); $R_f$=0.17 (30% ethyl acetate-hexane).

Step 2: Preparation of 2-hydroxy-4-(morpholin-4-yl)benzonitrile

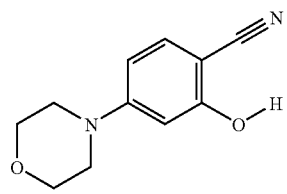

To a dry flask charged with 10% Pd/C (25.0 mg, 0.08 mmol, 0.1 eq) was added a solution of 2-(benzyloxy)-4-(morpholin-4-yl)benzonitrile (250 mg, 0.85 mmol) in 1:1 v/v ethyl acetate-ethanol (8.5 mL). The reaction mixture was hydrogenated under an atmosphere of hydrogen supplied by an attached balloon for 16 h. The reaction was filtered through a pad of celite, and the filtrate was concentrated. Crystallization from dichloromethane-hexanes gave 164.2 mg (94.7%) of a white solid. $^1$H-NMR (DMSO-$d_6$) δ 10.64 (broad s, 1H), 7.33 (d, J=9.0 Hz, 1H), 6.49 (dd, J=9.0 Hz, 2.1 Hz, 1H), 6.34 (d, J=2.1 Hz, 1H), 3.68 (t, J=5.1 Hz, 4H), 3.15 (t, J=5.1H, 4H); LC-MS (ES MH$^+$=205, RT=2.01 min); R$_f$=0.21 (50% ethyl acetate-hexane).

Step 3: Preparation of (3-Amino-6-morpholin-4-yl-benzofuran-2-yl)-(2,4-dichloro-phenyl)-methanone

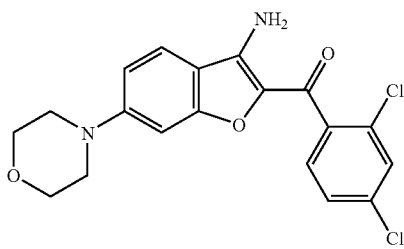

To a stirred solution of 2-hydroxy-4-(morpholin-4-yl)benzonitrile (75 mg, 0.37 mmol) and 2,2',4'-trichloroacetophenone (123.1 mg, 0.55 mmol, 1.5 eq) in anhydrous N,N-dimethylformamide (3.7 mL) was added potassium carbonate (76.1 mg, 0.46 mmol, 1.5 eq), and the orange reaction mixture was stirred at 80° C. for 17 h. The resulting dark wine color reaction was poured into ethyl acetate (100 mL) and water (50 mL). The ethyl acetate layer was washed with saturated aqueous ammonium chloride, water, and brine. The organic layer was then dried over sodium sulfate, filtered, and evaporated under reduced pressure. The crude product was purified on the MPLC (Biotage) eluted with 30% ethyl acetate-hexane. Crystallization from ether-hexane afforded the benzofuran as a yellow solid (37 mg, 25.8%). $^1$H-NMR (DMSO-$d_6$) δ 7.80 (d, J=9.3 Hz, 1H), 7.70 (m, 1H), 7.75 (m, 2H), 7.43 (broad s, 2H), 6.98 (dd, J=9 Hz, 1.8 Hz, 1H), 6.78 (d, J=1.8 Hz, 1H), 3.69 (t, J=4.5 Hz, 4H), 3.18 (t, J=4.5 Hz, 4H); LC-MS (ES MH$^+$=391/393, RT=3.11 min).

Example 178

Method E-3

Preparation of (3-Amino-6-pyrrol-1-yl-benzofuran-2-yl)-(2,4-dichloro-phenyl)-methanone

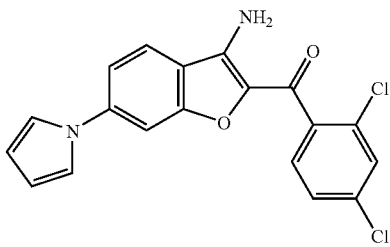

Step 1: Preparation of starting material: 2-hydroxy-4-(1H-pyrrol-1-yl)benzonitrile

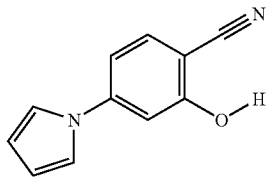

In a sealed tube was added methyl 2-hydroxy-4-(1H-pyrrol-1-yl)benzenecarboxylate (960 mg, 4.42 mmol), 1M sodium bis(trimethylsilyl)amide in THF (7.1 mL, 7.1 mmol, 1.6 eq), and 1,3-dimethylimidazolinone (1.77 mL), and the reaction mixture was heated to 185° C. for 17 h. The cooled reaction was quenched with 10% aqueous HCl solution and poured into ethyl acetate (200 mL) and water (100 mL). The ethyl acetate layer was washed with water and brine, dried over sodium sulfate, filtered, and evaporated under reduced pressure. The crude product was purified on the MPLC (Biotage) eluted with 25% ethyl acetate-hexane to give a white solid (585 mg, 71.9%). $^1$H-NMR (DMSO-$d_6$) δ 11.36 (s, 1H), 7.66 (d, J=8.4 Hz, 1H), 7.34 (t, J=2.4 Hz, 2H), 7.16 (dd, J=8.4 Hz, 2.4 Hz, 1H), 7.05 (d, J=1.8 Hz, 1H), 6.29 (t, J=2.4 Hz, 2H); R$_f$=0.18 (25% ethyl acetate-hexane).

Step 2: Preparation of the title compound: (3-Amino-6-pyrrol-1-yl-benzofuran-2-yl)-(2,4-dichloro-phenyl)-methanone

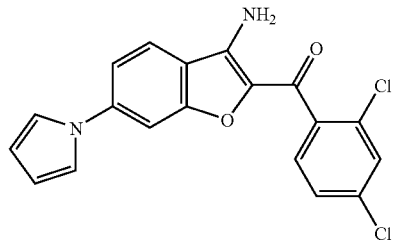

To a stirred solution of 2-hydroxy-4-(1H-pyrrol-1-yl)benzonitrile (60 mg, 0.33 mmol) and 2,2',4'-trichloroacetophenone (109.2 mg, 0.49 mmol, 1.5 eq) in anhydrous N,N-dimethylformamide (3.2 mL) was added potassium carbonate (67.5 mg, 0.49 mmol, 1.5 eq), and the orange reaction mixture was stirred at 80° C. for 16 h. The resulting dark wine color reaction was poured into ethyl acetate (100 mL) and water (50 mL). The ethyl acetate layer was washed with saturated aqueous ammonium chloride, water, and brine. The organic layer was then dried over sodium sulfate, filtered, and evaporated under reduced pressure. The crude product was purified on the MPLC (Biotage) eluted with 25% ethyl acetate-hexane. Crystallization from dichloromethane-hexane afforded the benzofuran as a yellow solid (89.0 mg, 73.6%). $^1$H-NMR (DMSO-$d_6$) δ 8.08 (d, J=8.7 Hz, 1H), 7.73 (d, J=10.0 Hz, 2H), 7.60 to 7.53 (m, 5H), 7.48 (t, J=2.4 Hz, 2H), 6.26 (t, J=2.1 Hz, 2H); LC-MS (ES MH⁺=371, RT=3.74 min).

Example 179

Method E-4

Preparation of (3-Amino-6-imidazol-1-yl-benzofuran-2-yl)-(2,4-dichloro-phenyl)-methanone

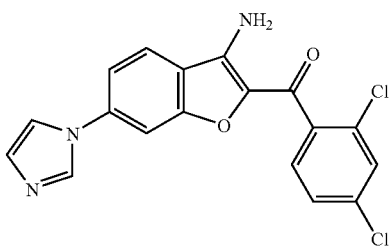

Step 1: Preparation of starting material: 2-benzyloxy-4-(imidazol-1-yl)benzonitrile

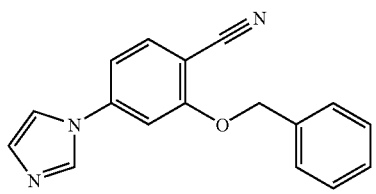

A mixture of 2-benzyloxy-4-iodo-benzonitrile (500 mg, 1.49 mmol); imidazole (152.3 mg, 2.24 mmol, 1.5 eq), cesium carbonate (534.7 mg, 1.64 mmol, 1.1 eq), copper (II) triflate (75.0 mg, 0.15 mmol, 0.1 eq), 1,10-phenanthroline (269 mg, 1.49 mmol, 1.0 eq), and trans, trans-dibenzylideneacetone (95.6 mg, 0.10 mmol, 0.1 eq) in anhydrous xylenes (6.0 mL) was sonicated for 2 min, and the reaction mixture was stirred at 110° C. for 19 h. The reaction was diluted with ethyl acetate, washed with water, brine, and dried over sodium sulfate. The solvent was removed at reduced pressure, and the crude material was purified on the MPLC (Biotage) eluted with 60% followed by 100% ethyl acetate. Crystallization from ethyl acetate-hexane afforded 240 mg (58.4%) of the product. ¹H-NMR (DMSO-d₆) δ 8.47 (t, J=0.9 Hz, 1H), 1.93 (t, J=1.5 Hz, 1H), 7.90 (d, J=8.4 Hz, 1H), 7.65 (d, J=2.1 Hz, 1H), 7.52 to 7.36 (m, 6H), 7.15 (t, J=1.5 Hz, 1H), 5.39 (s, 2H); LC-MS (ES MH⁺=276, RT=2.07 min); R$_f$=0.13 (75% ethyl acetate-hexane).

Step 2: Preparation of starting material: 2-hydroxy-4-(imidazol-1-yl)benzonitrile

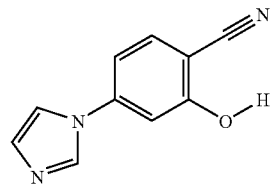

To a dry flask charged with 10% Pd/C (20.0 mg, 0.07 mmol, 0.1 eq) was added a solution of 2-benzyloxy-4-(imidazol-1-yl)benzonitrile (200 mg, 0.73 mmol) in 1:1 v/v ethyl acetate-ethanol (7.3 mL). The reaction mixture was hydrogenated under an atmosphere of hydrogen supplied by an attached balloon for 16 h. The reaction was filtered through a pad of celite, and the filtrate was concentrated. Recrystallization from ethyl acetate-hexane gave 120 mg (89.2%) of a white solid. ¹H-NMR (DMSO-d₆) δ 8.23 (s, 1H), 7.68 (s, 1H), 7.65 (d, J=8.1 Hz, 1H), 7.09 (s, 1H), 7.06 to 6.98 (m, 3H); R$_f$=0.13 (20% methanol-ethyl acetate).

Step 3: Preparation of the title compound: (3-Amino-6-imidazol-1-yl-benzofuran-2-yl)-(2,4-dichloro-phenyl)-methanone

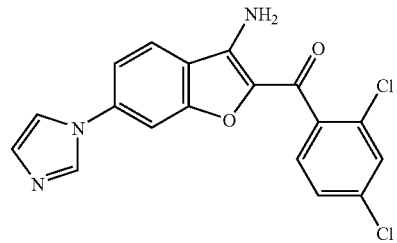

To a stirred solution of 2-hydroxy-4-(imidazol-1-yl)benzonitrile (60 mg, 0.32 mmol) and 2, 2',4'-trichloroacetophenone (108.6 mg, 0.49 mmol, 1.5 eq) in anhydrous N,N-dimethylformamide (3.2 mL) was added potassium carbonate (67.2 mg, 0.49 mmol, 1.5 eq), and the orange reaction mixture was stirred at 80° C. for 16 h. The resulting dark wine color reaction was poured into ethyl acetate (100 mL) and water (50 mL). The ethyl acetate layer was washed with saturated aqueous ammonium chloride, water, and brine. The organic layer was then dried over sodium sulfate, filtered, and evaporated under reduced pressure. The crude product was purified on the MPLC (Biotage) eluted with 75% ethyl acetate-hexane followed by 100% ethyl acetate. Crystallization from dichloromethane-hexane afforded the benzofuran as an orange solid (32.5 mg, 27.0%). ¹H-NMR (DMSO-d₆) δ 8.37 (s, 1H), 8.16 (d, J=8.4 Hz, 1H), 7.86 (d, J=1.8 Hz, 1H), 7.84 (t, J=1.3 Hz, 1H), 7.76 (d, J=1.5 Hz, 1H), 7.65 (dd, J=8.4 Hz, J=1.8 Hz, 1H), 7.58 to 7.57 (m, 4H), 7.11 (s, 1H); LC-MS (ES MH⁺=372, RT=2.37 min).

The other compounds in Table 4 can be prepared in like manner as described above by choosing the appropriate starting materials that are readily available and/or the synthesis of which is taught herein, and using the process described above or other standard chemical processes known in the art.

TABLE 4

Examples Synthesized using Method E

| Example | Structure | R_f (TLC solvent) Or RT (min)* | LC/MS ([M + H]+) | Synthesis of (III)** | Synthesis of R4-H** | Synthesis of (I) |
|---|---|---|---|---|---|---|
| 180 | (structure) | R_f = 0.41 (75% EtOAc/HEX) | 355/357 | A-2 | comm | E-1 |
| 181 | (structure) | R_f = 0.14 (50% EtOAc/HEX) | 389/391 | comm | comm | E-1 |
| 182 | (structure) | R_f = 0.18 (75% EtOAc/HEX) | 390/392 | comm | comm | E-1 |
| 183 | (structure) | R_f = 0.16 (50% EtOAc/HEX) | 404/406 | comm | comm | E-1 |
| 184 | (structure) | R_f = 0.23 (75% EtOAc/HEX) | 384.0 | A-2 | comm | E-1 |
| 185 | (structure) | R_f = 0.16 (25% EtOAc/HEX) | 375.0 | comm | comm | E-2 |

TABLE 4-continued

Examples Synthesized using Method E

| Example | Structure | $R_f$ (TLC solvent) Or RT (min)* | LC/MS ([M + H]+) | Synthesis of (III)** | Synthesis of R4-H** | Synthesis of (I) |
|---|---|---|---|---|---|---|
| 186 | 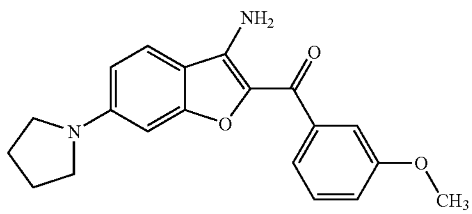 | $R_f$ = 0.30 (50% EtOAc/HEX) | 337.0 | comm | comm | E-2 |
| 187 | 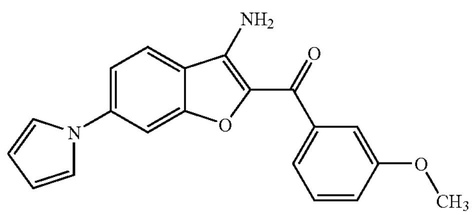 | $R_f$ = 0.12 (25% EtOAc/HEX) | 333.0 | comm | comm | E-3 |
| 188 | 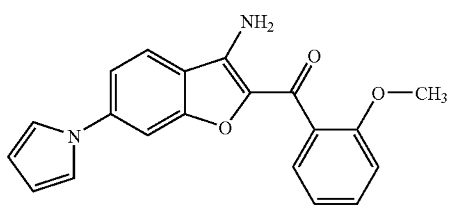 | $R_f$ = 0.1 (25% EtOAc/HEX) | 333.0 | comm | comm | E-3 |
| 189 | 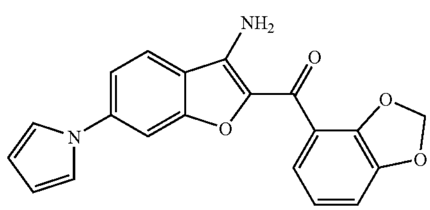 | RT = 3.23 | 347.3 | A-5 | comm | E-3 |
| 190 | 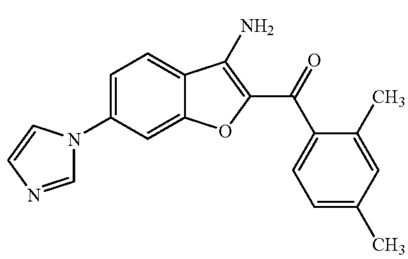 | $R_f$ = 0.26 (5% MeOH/EtOAc) | 332.0 | comm | comm | E-4 |

TABLE 4-continued

Examples Synthesized using Method E

| Example | Structure | R$_f$ (TLC solvent) Or RT (min)* | LC/MS ([M + H]+) | Synthesis of (III)** | Synthesis of R4-H** | Synthesis of (I) |
|---|---|---|---|---|---|---|
| 191 | 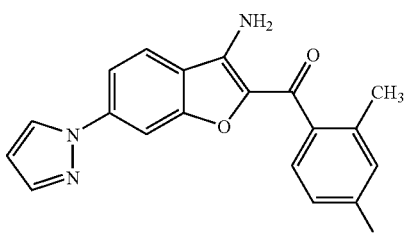 | R$_f$ = 0.11 (25% EtOAc/HEX) | 332.0 | comm | comm | E-4 |
| 192 | 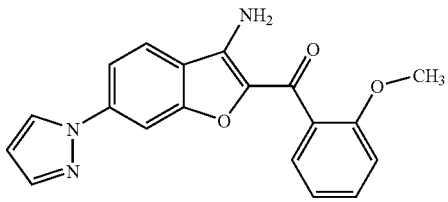 | R$_f$ = 0.17 (25% EtOAc/HEX) | 334.0 | comm | comm | E-4 |
| 193 | 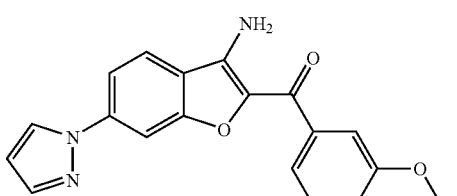 | R$_f$ = 0.08 (25% EtOAc/HEX) | 334.0 | comm | comm | E-4 |
| 194 | 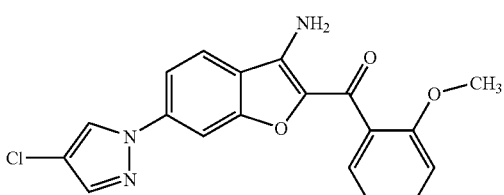 | R$_f$ = 0.345 (50% EtOAc/HEX) | 368.0 | comm | comm | E-4 |

Footnotes:

*The following are the LOMS conditions: HPLC - electrospray mass spectra (HPLO ES-MS) were obtained using a Gilson HPLC system equipped with two Gilson 306 pumps, a Gilson 215 Autosampler, a Gilson diode array detector, a YMC Pro C-18 column (2 × 23 mm, 120 A), and a Micromass LCZ single quadrupole mass spectrometer with z-spray electrospray ionization. Spectra were scanned from 120-1000 amu over 2 seconds. ELSD (Evaporative Light Scattering Detector) data was also acquired as an analog channel. Gradient elution was used with Buffer A as 2% acetonitrile in water with 0.02% TFA and Buffer B as 2% water in Acetonitrile with 0.02% TFA at 1.5 mL/min. Samples were eluted as follows: 90% A for 0.5 min ramped to 95% B over 3.5 min and held at 95% B for 0.5 min and then the column is brought back to initial conditions over 0.1 min. Total run time is 4.8 min.

**comm means commercially available.

General Method F: Preparation of Compounds of Formula (I) from Other Compounds of Formula I The various means used for the further derivatization of compounds of formula I (prepared by means described above) into other compounds of formula (I) are described in the examples below.

Example 195

Method F-1a

Preparation of N-[2-(2,4-Dichloro-benzoyl)-6-phenyl-benzofuran-3-yl]-acetamide

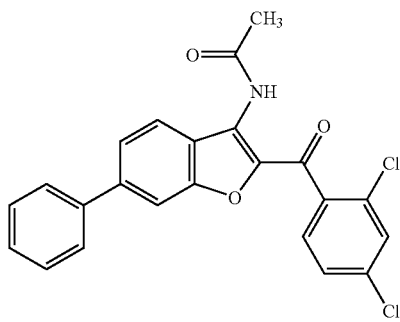

A mixture of (3-amino-6-phenyl-1-benzofuran-2-yl)(2,4-dichlorophenyl)methanone (129 mg, 0.337 mmol), acetyl chloride (0.10 mL, 1.41 mmol, 4.2 eq), diisopropylethylamine polystyrene resin (100 mg, 3.75 mmol/g loading, 1.1 eq) in anhydrous dichloroethane was shaken at 40° C. for 4 days. The reaction mixture was filtered, and the filtrate was concentrated. The crude product was purified on the MPLC (Biotage) eluted with 10% ethyl acetate-hexane. Crystallization from ether-hexane afforded 86.8 mg (60.6%) of the product. $^1$H-NMR (DMSO-$d_5$) δ 10.36 (s, 1H), 8.03 (d, J=8.7 Hz, 1H), 7.95 (d, J=1.0 Hz, 1H), 7.83 (d, J=1.8 Hz, 1H), 7.77 (d, J=6.9 Hz, 1H), 7.72 to 7.62 (m, 4H), 7.49 to 7.39 (m, 3H), 2.12 (s, 3H); LC-MS (ES MH$^+$=423, RT=4.01 min).

Example 196

Method F-1b

Preparation of N-[6-(3-Cyano-phenyl)-2-(2,4-dichloro-benzoyl)-benzofuran-3-yl]-acetamide

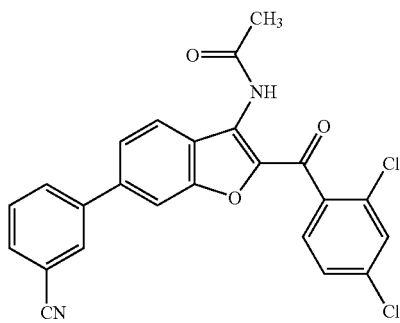

To the solution of 3-[3-amino-2-(2,4-dichloro-benzoyl)-benzofuran-6-yl)]-benzonitrile (prepared according to Method C-1) (200 mg, 0.5 mmol) in anhydrous THF (2 mL) was added acetic anhydride (0.12 mL, 1.2 mmol, 2.5 eq) and sodium acetate (100 mg, 1.2 mmol, 2.5 eq). The reaction mixture was stirred at 60° C. for 40 h. While cooling down to rt, some white solid precipitated and was filtered off. The filtrate was evaporated in vacuo and washed with water and EtOAc. Drying with high vacuum pump gave 120 mg (55%) N-[6-(3-Cyano-phenyl)-2-(2,4-dichloro-benzoyl)-benzofuran-3-yl]-acetamide as a yellow solid. $^1$H-NMR (CDCl$_3$) δ 10.36 (broad, s, 1H), 8.67 (d, J=8.8 Hz, 1H), 7.89 to 7.83 (m, 2H), 7.67 to 7.49 (m, 6H), 7.40 (dd, J=8.8 Hz, 2 Hz, 1H), 2.40 (s, 3H). R$_f$=0.62, 50% EtOAc-HEX.

Example 197

Method F-2

Preparation of 3-[3-Amino-2-(2,4-dichloro-benzoyl)-benzofuran-6-yl]-benzamide

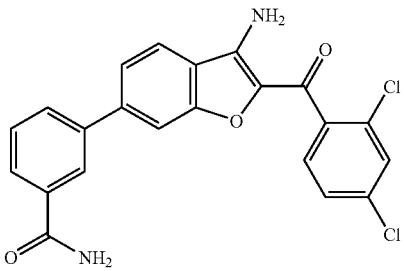

To a solution of 3-amino-6-(3'-cyanophenyl)-1-benzofuran-2-yl)(2,4-dichlorophenyl)methanone (36 mg, 0.09 mmol) in acetone (1.7 mL) and water (0.88 mL) was added sodium percarbonate with 25% hydrogen peroxide (69.4 mg, 0.44 mmol, 5 eq). The reaction mixture was stirred at 60° C. for 7 h. The reaction mixture was cooled and the volatile solvent was evaporated. The residue was diluted with ethyl acetate, washed with water, brine, and dried over sodium sulfate. The solvent was removed at reduced pressure, and the crude product was recrystallized from ethyl acetate-hexane to afford 18.8 mg (50.0%) of the product. $^1$H-NMR (DMSO-$d_6$) δ 8.22 (t, J=1.5 Hz, 1H), 8.14 (d, J=8.7 Hz, 1H), 8.09 (s, 1H), 7.92 to 7.84 (m, 3H), 7.73 (d, J=1.8 Hz, 1H), 7.69 (dd, J=8.1 Hz, 1.5 Hz, 1H), 7.62 to 7.51 (m, 5H), 7.44 (s, 1H); LC-MS (ES MH$^+$ 425, RT=2.99 min).

Example 198

Method F-3

Preparation of N-{3-[3-amino-2-(2,4-dichloro-benzoyl)-benzofuran-6-yl]-phenyl}-2-methoxyacetamide

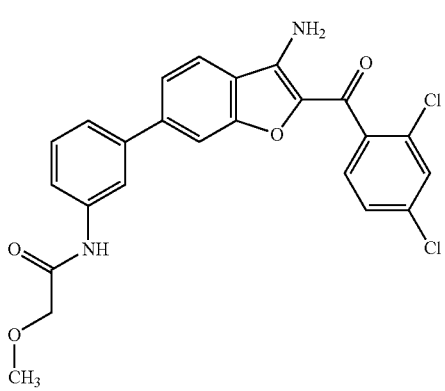

A solution of methoxy acetic acid (27.2 mg, 0.30 mmol, 1.5 eq), 1-(3-dimethylaminopropyl)-3-ethylcarbodiimide hydrochloride (57.9 mg, 0.30 mmol, 1.5 eq), 1-hydroxybenzotriazole hydrate (40.8 mg, 0.30 mmol, 1.5 eq), and diisopropylethylamine (698 mg, 0.60 mmol, 3 eq) in anhydrous 1:1 v/v THF-acetonitrile (5 mL) was stirred at room temperature under argon for 1 h. A solution of [3-amino-6-(3-aminophenyl)-benzofuran-2-yl]-(2,4-dichlorophenyl)methanone (80 mg, 0.20 mmol) in anhydrous THF (5 mL) was then added, and the reaction mixture was stirred at 80° C. for 18 h. The reaction mixture was diluted with ethyl acetate and water, and the organic layer was washed with water, brine, and dried. The crude product was purified via preparative thin-layer chromatography using 50% ethyl acetate-hexane as the eluant. Crystallization from ether-hexane afforded 28.2 mg (29.9%) of the product. $^1$H-NMR (Acetone-$d_6$) δ 9.10 (broad s, 1H), 8.15 (m, 1H), 8.10 (dd, J=8.1 Hz, 1.8 Hz, 1H), 7.83 (m, 1H), 7.65 to 7.41 (m, 7H), 7.11 (broad, s, 2H), 4.03 (s, 2H), 3.47 (s, 3H); MS ES (MH$^+$=496); $R_f$=0.28 (30% ethyl acetate-hexane).

Example 199

Method F-4

Preparation of 2-amino-N-{3-[3-amino-2-(2,4-dichloro-benzoyl)-benzofuran-6-yl]-phenyl}acetamide

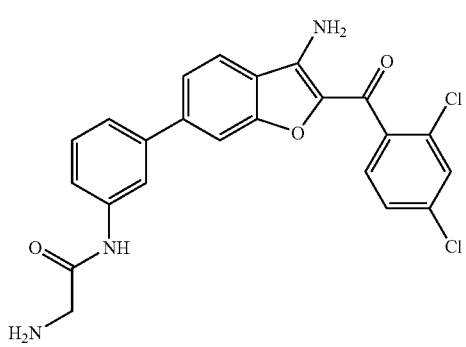

A mixture of N-{3-[3-amino-2-(2,4-dichlorobenzoyl)-benzofuran-6-yl]-phenylcarbamoyl}-methyl)carbamic acid tert-butyl ester prepared according Example 198 F-3 (80 mg, 0.14 mmol) in trifluoroacetic acid (20 mL) and anhydrous THF (40 mL) was stirred under argon at room temperature for 18 h. The reaction mixture was diluted with ethyl acetate and water, and the organic layer was washed with saturated aqueous sodium carbonate, water, brine, and dried over magnesium sulfate. The solvent was evaporated under reduce pressure, and the crude product was purified on the MPLC (Biotage) eluted with 10% dichloromethane-methanol to give 21.3 mg (32.5%) of product. $^1$H-NMR (Acetone-$d_6$) δ 9.96 (broad s, 1H), 8.09 (m, 2H), 8.00 to 7.42 (m, 7H), 7.27 (d, J=7.8 Hz, 1H), 7.10 (broad s, 2H), 4.00 (s, 2H), 2.92 (broad s, 2H); MS ES (MH$^+$=454); $R_f$=0.33 (10% dichloromethane-methanol).

Example 200

Method F-5

Preparation of {3-Amino-6-[3-((R)-2,3-dihydroxy-propylamino)-phenyl]-benzofuran-2-yl}-(2,4-dichloro-phenyl)-methanone

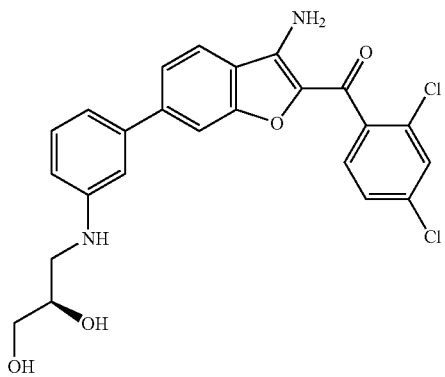

A mixture of 3-amino-6-(3 aminophenyl)-1-benzofuran-2-yl)(2,4-dichlorophenyl)methanone (150.0 mg, 0.38 mmol) and (S)-(−)-glycidol (0.03 mL, 0.38 mmol, 1.0 eq) in 2:1 v/v dioxane-water was stirred at 80° C. for 16 h. The reaction was diluted with ethyl acetate, washed with water, brine, and dried over sodium sulfate. The solvent was removed at reduced pressure, and the crude material was purified on the MPLC (Biotage) eluted with 5% methanol-ethyl acetate to afford 78.2 mg (43.9%) of the product. $^1$H-NMR (Acetone-$d_6$) δ 8.03 (d, J=8.4 Hz, 1H), 7.65 to 7.53 (m, 5H), 7.20 (t, J=8.1 Hz, 1H), 7.70 (broad s, 2H), 7.04 (t, J=2.1 Hz, 1H), 6.95 (d, J=8.1 Hz, 1H), 6.72 (dd, J=7.8 Hz, 2.4 Hz, 1H), 5.03 (broad s, 1H), 3.96 (broad s, 1H), 3.89 (t, J=5.4 Hz, 1H), 3.74 (broad s, 1H), 3.66 to 3.59 (m, 2H), 3.44 to 3.36 (m, 1H), 3.21 to 3.12 (m, 1H); LC-MS (ES MH$^+$=471, RT=2.82 min).

Example 201

Method F-6a

Preparation of (3-Amino-6-piperidin-3-yl-benzofuran-2-yl)-(2,4-dichloro-phenyl)-methanone

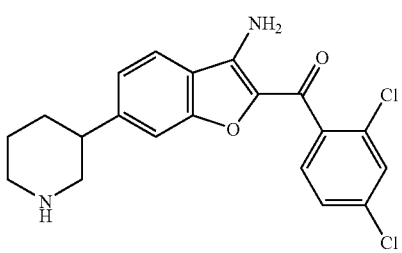

PtO$_2$ (4.0 mg, 0.018 mmol) was added to a dry flask. Methanol (0.6 mL), tetrahydrofuran (0.5 mL), and hydrogen chloride (50 μL, 2N in dioxane) were added after the flask was flushed with argon. (3-amino-6-pyridin-3-yl-benzofuran-2-yl)-(2,4-dichloro-phenyl)-methanone (40 mg, 0.10 mmol) was added to the flask under argon atmosphere. The solution was degassed under vacuum and refilled with argon. Hydrogen gas was introduced to the flask by a balloon. The mixture was stirred under an H₂ atmosphere at room temperature overnight. The mixture was then filtered and the filtrate concentrated in vacuo. The resulting residue was purified by HPLC to afford 15.5 mg (38.2%) of the title compound. ¹H-NMR (CDOD₃) δ 7.89 (d, J=8.1 Hz, 1H), 7.58 (d, J=1.7 Hz, 1H), 7.47 (m, 2H), 7.29 (s, 1H), 7.23 (dd, J=8.2 Hz, 1.7 Hz, 1H), 3.44 (m, 2H), 3.08 (m, 3H), 2.07 (t, 2H), 1.86 (m, 2H); MS LC-MS (MH⁺=389.6).

Example 202

Method F-6b

Preparation of 1-{3-[3-Amino-2-(2,4-dichloro-benzoyl)-benzofuran-6-yl]-piperidin-1-yl}-3-diethylamino-propan-1-one

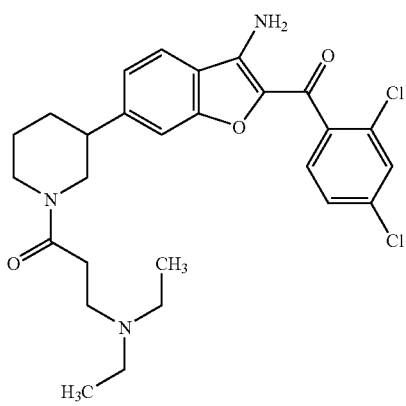

A mixture of (3-amino-6-piperidin-3-yl-benzofuran-2-yl)-(2,4-dichloro-phenyl)-methanone (65 mg, 0.17 mmol), (3-dimethylamino-propyl)-ethyl-carbodiimide hydrochloride (35 mg, 0.18 mmol), and 1-hydroxybenzotriazole (25 mg, 0.18 mmol) in methylene chloride (1.5 mL) was stirred at room temperature for 10 min. Triethylamine (70 μl, 0.50 mmol) and 3-diethylamino-propionic acid (24 mg, 0.17 mmol) were added to the mixture. The solution was stirred at room temperature overnight. The solution was concentrated in vacuo and the resulting residue was purified by HPLC to afford 31 mg (42%) of the title compound. ¹H-NMR (CDCl₃) δ 7.54 (d, J=8.8 Hz, 1H), 7.42 (m, 2H), 7.29 (m, 1H), 7.12 (d, J=4.9 Hz, 1H), 7.06 (d, J=8.4 Hz, 1H), 6.04 (d, 2H), 4.67 (t, J=14.5 Hz, 1H), 3.87 (m, 1H), 2.99 (t, J=12.5 Hz, 1H), 2.76 (m, 3H), 2.49 (m, 6H), 2.00 (m, 1H), 1.79 (m, 1H), 1.62 (m, 1H), 1.54 (m, 1H), 0.96 (m, 6H); MS LC-MS (MH⁺=516.9).

Example 203

Method F-6c

Preparation of [3-Amino-6-(1-isopropyl-piperidin-3-yl)-benzofuran-2-yl]-(2,4-dichloro-phenyl)-methanone

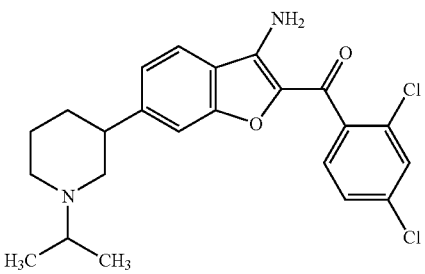

A mixture of (3-amino-6-piperidin-3-yl-benzofuran-2-yl)-(2,4-dichloro-phenyl)-methanone (50 mg, 0.13 mmol), acetone ((10 μl, 0.13 mmol), sodium triacetoxyborohydride (38 mg, 0.18 mmol), triethylamine (27 μl, 0.19 mmol), and acetic acid (7.0 μl, 0.13 mmol) in 1,2-dichloroethane (1.3 mL) was stirred at room temperature overnight. The solution was concentrated. The resulting residue was purified by HPLC to afford 18 mg (32%) of the title compound. ¹H-NMR (CDCl₃) δ 7.53 (d, J=8.4 Hz, 1H), 7.49 (s, 1H), 7.48 (d, J=4.6 Hz, 1H), 7.35 (dd, J=8.7, 2.2 Hz, 1H), 7.21 (s, 1H), 7.15 (d, J=8.7 Hz, 1H), 6.02 (s, 2H), 2.94 (m, 3H), 2.76 (m, 1H), 2.16 (m, 2H), 1.94 (m, 1H), 1.80 (m, 1H), 1.69 (m, 1H), 1.46 (m, 1H), 1.04 (d, J=2.6 Hz, 3H), 1.02 (d, J=2.6 Hz, 3H); MS LC-MS (MH⁺= 431.7).

Example 204

Method F-6d

Preparation of [3-Amino-6-(1-butyl-piperidin-3-yl)-benzofuran-2-yl]-(2,4-dichloro-phenyl)-methanone

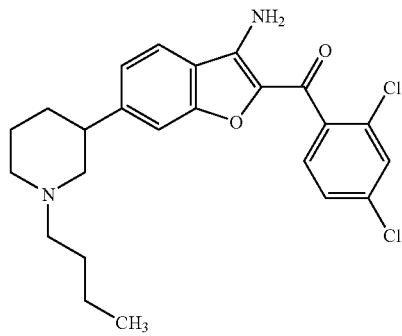

This compound was prepared from (3-amino-6-piperidin-3-yl-benzofuran-2-yl)-(2,4-dichloro-phenyl)-methanone (50 mg, 0.13 mmol) in the manner described for [3-amino-6-(1-isopropyl-piperidin-3-yl)-benzofuran-2-yl]-(2,4-dichloro-phenyl)-methanone affording 27 mg (47%) of the title compound as a yellow solid. ¹H-NMR (CDCl₃) δ 7.53 (d, J=8.3 Hz, 1H), 7.49 (d, J=2.1 Hz, 1H), 7.48 (d, J=4.2 Hz, 1H), 7.34 (dd, J=8.5, 2.1 Hz, 1H), 7.21 (s, 1H), 7.14 (dd, J=8.5, 2.4 Hz, 1H), 6.01 (s, 2H), 2.97 (m, 3H), 2.33 (m, 2H), 1.94 (m, 3H), 1.75 (m, 2H), 1.46 (m, 3H), 1.29 (m, 2H), 0.89 (t, J=7.3 Hz, 3H); MS LC-MS (MH⁺=445.4).

Example 205

Method F-7a

Preparation of 2-{3-[3-Amino-2-(2,4-dichloro-benzoyl)-benzofuran-6-yl]-phenyl}-acetamidine trifluoro-acetic acid

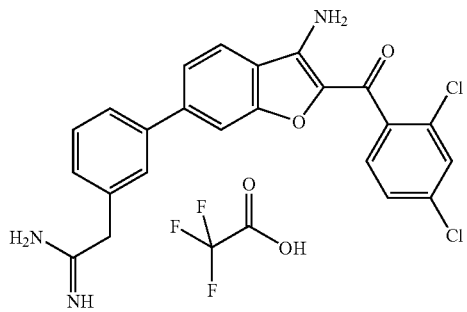

A solution of 3-[3-amino-2-(2,4-dichloro-benzoyl)-benzofuran-6-yl]-benzonitrile (160 mg, 38.0 mmol) in methanol (10 mL) was saturated with hydrochloride gas at 0° C., and stirred at room temperature for 1 h. Then it was saturated with more hydrochloride gas and stirred at room temperature for another 1 h until TLC showed no starting material left. The solvent was removed under reduced pressure. The resulting crude 3-[3-amino-2-(2,4-dichloro-benzoyl)-benzofuran-6-yl]-benzimidic acid methyl ester residue was treated with ammonia in methanol (7 N, 10 mL) and stirred at room temperature overnight. The solvent was removed at reduced pressure. After HPLC separation, a white solid product (34.4 mg, 16.4%) of 2-{3-[3-amino-2-(2,4-dichloro-benzoyl)-benzofuran-6-yl]-phenyl}-acetamidine trifluoro-acetic acid was obtained. ¹H-NMR (CD₃OD) δ 6.34 (d, J=8.7 Hz, 1H), 6.07 (s, 1H), 6.03 (d, J=7.7 Hz, 1H), 5.94 (m, 3H), 5.86 (t, J=8.0 Hz, 2H), 5.82 (s, 1H), 5.77 (t, J=7.4 Hz, 1H), 2.23 (s, 2H); MS LC-MS (MH⁺=438.3), LC MS RT: 2.42 min.

Example 206

Method F-7b

Preparation of 3-[3-Amino-2-(2,4-dichloro-benzoyl)-benzofuran-6-yl]-N,N-dimethyl-benzamidine

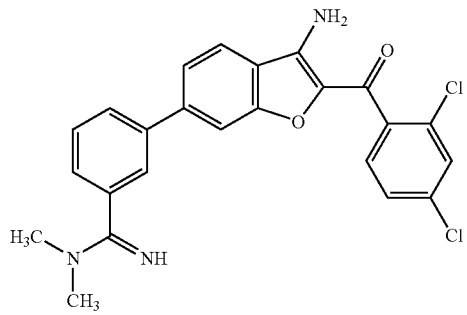

To anhydrous methanol (10 mL) was added 3-[3-amino-2-(2,4-dichloro-benzoyl)-benzofuran-6-yl]-benzonitrile (1.0 g, 2.46 mmol). The solution was then saturated with HCl gas. This was stirred at rt for one h. The solution was then concentrated in vacuo and a portion of the residue (0.070 g, 0.16 mmol) was dissolved in anhydrous MeOH (2 mL) under an inert atmosphere. To this was added dimethylamine (3.1 g, 69 mmol). The solution was then allowed to stir for 72 h at rt. The solution was then concentrated in vacuo, and purified via HPLC to yield 0.025 g (34.7%) of 3-[3-amino-2-(2,4-dichloro-benzoyl)-benzofuran-6-yl]-N,N-dimethyl-benzamidine. ¹HNMR (MeOH-d₄) δ 7.99 (d, J=9.3 Hz, 1H), d 7.78 (d, J=8 Hz 1H), d 7.69 (s, 1H), d 7.62-7.39 (m, 7H), d 2.98 (s, 6H); LC-MS RT: 2.45 min, M+H⁺: 452.3/454.2/456.2.

Example 207

Method F-8

Preparation of [3-Amino-6-(3-methylamino-phenyl)-benzofuran-2-yl]-(2,4-dichloro-phenyl)-methanone

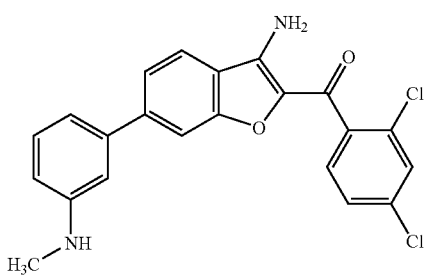

A mixture of [3-amino-6-(3-amino-phenyl)-benzofuran-2-yl]-(2,4-dichloro-phenyl)-methanone (100 mg, 0.25 mmol), formaldehyde (7.5 μL, 0.26 mmol), sodium triacetoxyborohydride (75 mg, 0.35 mmol), and acetic acid (15 mL, 0.25 mmol) in 1,2-dichloroethane was stirred at room temperature overnight. The solvent was removed at reduced pressure and the residue was purified on the MPLC (Biotage) eluted with 5% to 30% ethyl acetate-hexane affording as a yellow solid (13.7 mg, 13.2%). ¹H-NMR (CDCl₃) δ 7.65 (d, J=8.8 Hz, 1H), 7.54 (s, 1H), 7.51 (m, 2H), 7.37 (dd, J=8.2, 2.0 Hz, 1H), 7.27 (t, J=7.8 Hz, 1H), 7.26 (s, 1H), 6.95 (d, J=7.6 Hz, 1H), 6.82 (t, J=2.0 Hz, 1H), 6.75 (dd, J=8.2 Hz, 2.5 Hz, 1H), 6.01 (s, 2H), 2.89 (s, 3H); MS LC-MS (MH⁺=411.2), RT=3.47 min.

Example 208

Method F-9

Preparation of (3-Amino-6-pyridin-3-yl-benzofuran-2-yl)-(2,4-dichlorophenyl)methanone hydrochloride

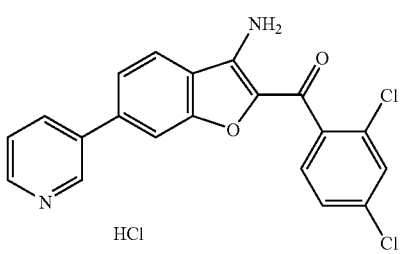

To a solution of (3-Amino-6-pyridin-3-yl-benzofuran-2-yl)-(2,4-dichlorophenyl)methanone (80 mg, 0.21 mmol) in hot ethanol (3 mL) was added concentrated hydrochloric acid (0.16 mL, 5.22 mmol, 25 eq). The reaction mixture was stored at RT for 18 h and at 3° C. for 24 h until crystalline solid is formed. The yellow precipitate was filtered and washed with cold ethanol to afford 37.5 mg (42.8%) of the hydrochloride salt. $^1$H-NMR (DMSO-d$_6$) δ 9.19 (s, 1H), 8.78 (d, J=5.1 Hz, 1H), 8.66 (d, J=7.5 Hz, 1H), 8.22 (d, J=8.4 Hz, 1H), 7.99 (s, 1H), 7.90 (t, J=6.6 Hz, 1H), 7.78 to 7.75 (m, 2H), 7.64 to 7.55 (m, 4H); MS ES (MH$^+$=383; retention time=2.48 min).

Other compounds in Table 5 were be prepared in like manner as described above for Examples 195 F1-208 F-9, starting from the appropriate starting materials that are either readily available and/or the synthesis of which is taught herein, and using the process described above or other standard chemical processes known in the art.

TABLE 5

Examples Synthesized using Method F

| Example | Structure | $R_f$ (TLC solvent) Or RT (min)* | LC/MS ([M + H]+) | Synthesis of (III)** | Synthesis of (VI) or (VII)** | Synthesis of (I) |
|---|---|---|---|---|---|---|
| 209 | 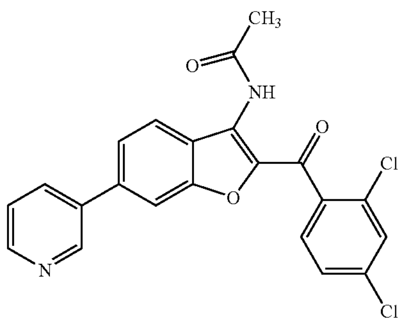 | $R_f$ = 0.37 (75% EtOAc/HEX) | 425.0 | comm | comm | C-1, F-1 |
| 210 | 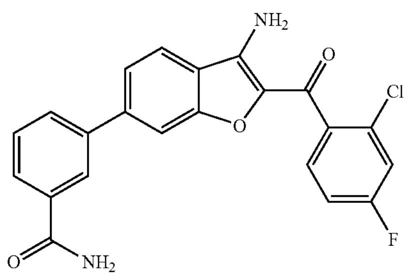 | $R_f$ = 0.29 (100% EtOAc/HEX) | 409.0 | A-2 | comm | C-1, F-2 |
| 211 | 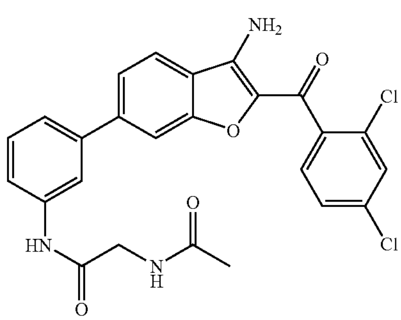 | $R_f$ = 0.10, HEX/EtOAc = 50/50 | 496.0 | comm | comm | C1, F-3 |
| 212 | 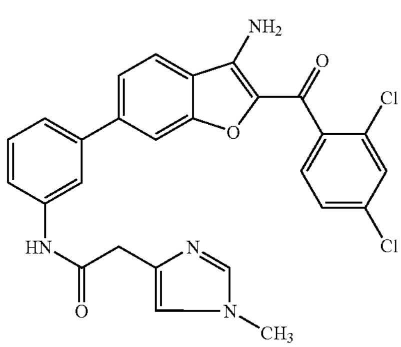 | $R_f$ = 0.08, HEX/EtOAc = 50/50, 90% PURE | 519/521 | comm | comm | C1, F-3 |

TABLE 5-continued

Examples Synthesized using Method F

| Example | Structure | $R_f$ (TLC solvent) Or RT (min)* | LC/MS ([M + H]+) | Synthesis of (III)** | Synthesis of (VI) or (VII)** | Synthesis of (I) |
|---|---|---|---|---|---|---|
| 213 | 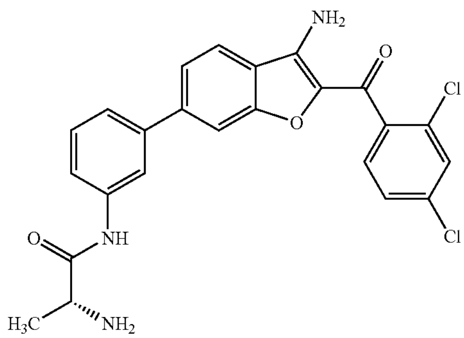 | $R_f$ = 0.30, CH$_2$Cl$_2$//MeOH = 90/10 | 468.0 | comm | comm | C-1, F-3 F-4 |
| 214 | 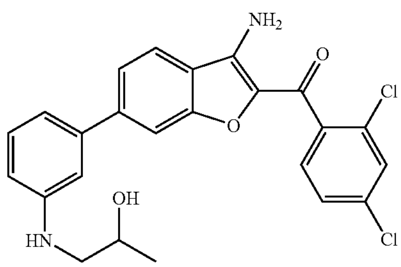 | $R_f$ = 0.22 (50% EtOAc/HEX) | 455.0 | comm | comm | C-1, F-5 |
| 215 | 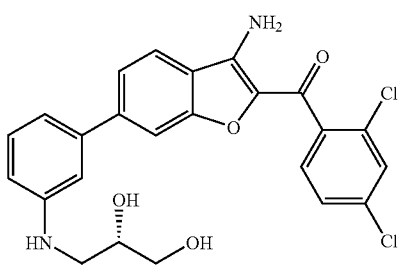 | $R_f$ = 0.28 (100% EtOAc) | 471.0 | comm | comm | C-1, F-5 |
| 216 | 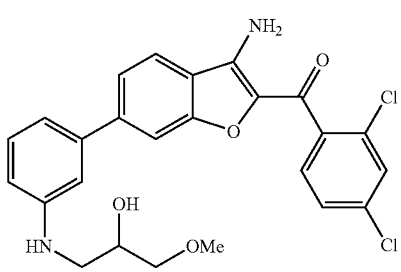 | $R_f$ = 0.13 (50% EtOAc/HEX) | 485.0 | comm | comm | C-1, F-5 |
| 217 | 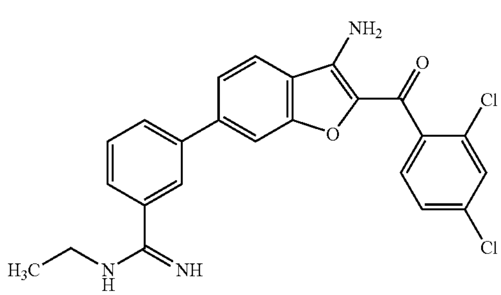 | RT = 2.55 | 452.3 | comm | comm | C-1, F-7 |

TABLE 5-continued

Examples Synthesized using Method F

| Example | Structure | $R_f$ (TLC solvent) Or RT (min)* | LC/MS ([M + H]+) | Synthesis of (III)** | Synthesis of (VI) or (VII)** | Synthesis of (I) |
|---|---|---|---|---|---|---|
| 218 | 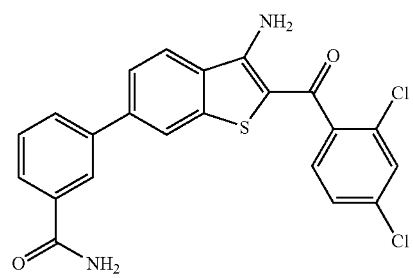 | $R_f$ = 0.10, HEX/EtOAc = 50/50 | 441 | comm | comm | G, F-2 |
| 219 | 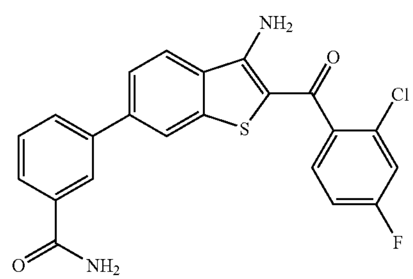 | $R_f$ = 0.08, HEX/EtOAc = 50/50 | 425 | A-4 | comm | G, F-2 |
| 220 | 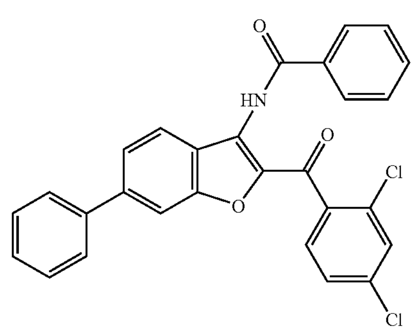 | RF = 0.75 [25% Ea/Hex] | [Elemental Analysis Calcd for $C_{28}H_{17}Cl_2NO_3$: % C 69.15 % H 3.52 % N 2.88, Found: % C 69.01 % H 3.57 % N 2.84] | comm | | B-1, F-1 |

Footnotes:

*The following are the LCMS conditions: HPLC - electrospray mass spectra (HPLC ES-MS) were obtained using a Gilson HPLC system equipped with two Gilson 306 pumps, a Gilson 215 Autosampler, a Gilson diode array detector, a YMC Pro C-18 column (2 × 23 mm, 120 A), and a Micromass LCZ single quadrupole mass spectrometer with z-spray electrospray ionization. Spectra were scanned from 120-1000 amu over 2 seconds. ELSD (Evaporative Light Scattering Detector) data was also acquired as an analog channel. Gradient elution was used with Buffer A as 2% acetonitrile in water with 0.02% TFA and Buffer B as 2% water in Acetonitrile with 0.02% TFA at 1.5 mL/min. Samples were eluted as follows: 90% A for 0.5 min ramped to 95% B over 3.5 min and held at 95% B for 0.5 min and then the column is brought back to initial conditions over 0.1 min. Total run time is 4.8 min.

**comm means commercially available.

General Method G: Preparation of Benzothiophenes of Formula (I)

The preparation of benzothiophenes in this invention is illustrated in the General Scheme below and specifically described in preparation of Example 221.

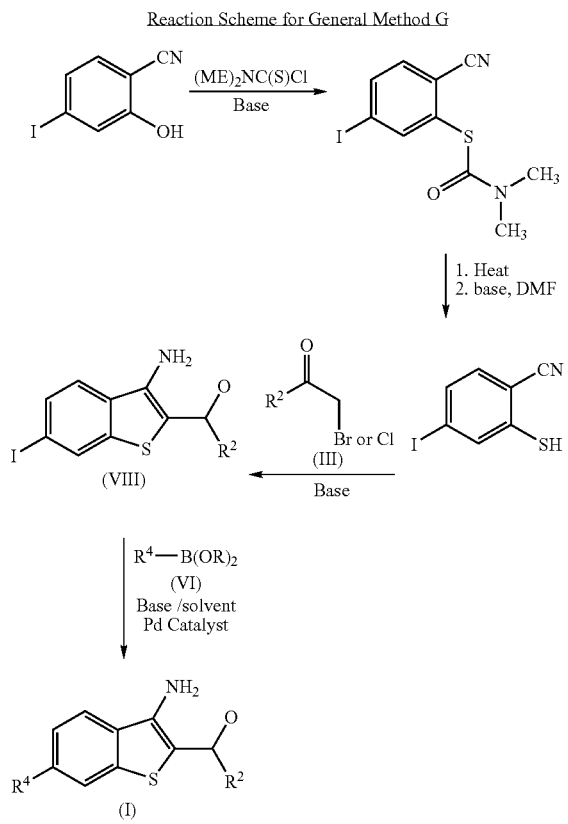

Example 221

Method G

The Preparation of [3-amino-6-(3-pyridinyl)-1-benzothiophene-2-yl](2,4-dichlorophenyl)methanone

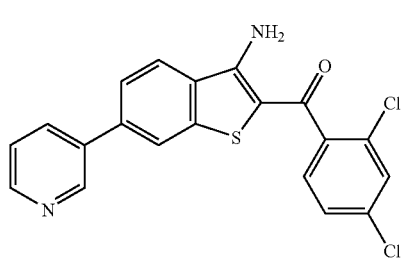

Step 1: Preparation of 2-cyano-5-iodophenyl-(dimethylamino)methanethioate

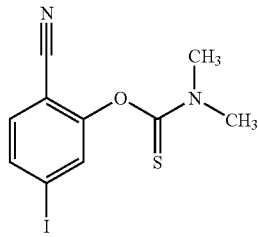

To a solution of 2-cyano-5-iodophenol (10.0 g, 40.8 mmol) in acetone (100 mL) was added dropwise a solution of potassium hydroxide (2.52 g, 44.9 mmol, 1.1 eq) in water (60 mL) at 0° C. After stirring for 45 min, a solution of dimethylthiocarbamoyl chloride (5.55 g, 44.9 mmol, 1.1 eq) in acetone (60 mL) was added at 0° C. over 30 min. The resulted brown reaction mixture was then stirred at room temperature for 16 h, and diluted with ethyl acetate and water. The organic layer was washed with saturated aqueous ammonium chloride, water, and brine. The combined aqueous washes were re-extracted with ethyl acetate, and the organic layers were dried, filtered, and evaporated under reduced pressure. The crude oil was crystallized from ether/hexane to give 2-cyano-5-iodophenyl-(dimethylamino)methanethioate (10.3 g, 76.0%) as a beige solid: $^1$H-NMR (Acetone-$d_6$) δ 7.89 (dd, J=8.4, 1.8 Hz, 1H), 7.79 (d, J=1.5 Hz, 1H), 7.60 (dd, J=8.1 Hz, 1H), 3.44 (s, 6H); MS ES (MH$^+$=333); $R_f$=0.70 (30% ethyl acetate-hexane).

Step 2: Preparation of S-(2-cyano-5-iodo-phenyl)-dimethylthio-carbamic acid

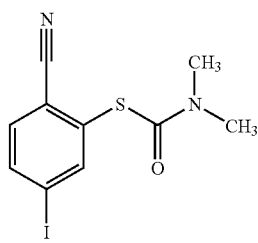

2-Cyano-5-Iodophenyl-(dimethylamino)methanethioate (10.0 g, 30.1 mmol) was heated to a melt at 200° C. under argon for 6 h. The reaction was cooled to room temperature, and the resulted brown solid was purified on the MPLC (Biotage) eluted with 20% ethyl acetate-hexane to give S-(2-cyano-5-iodo-phenyl)-dimethylthio-carbamic acid as a white solid (8.3 g; 83.0%); $^1$H-NMR (Acetone-$d_6$) δ 8.12 (d, J=1.8 Hz, 1H), 8.05 (dd, J=7.8, 1.5 Hz, 1H), 7.66 (d, J=8.1 Hz, 1H), 3.11 (broad s, 3H), 3.08 (broad s, 3H); MS ES (MH$^+$=333.0), $R_f$=0.53 (30% ethyl acetate-hexane).

Step 3: Preparation of 2-cyano-5-iodothiophenol

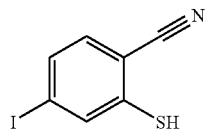

To S-(2-cyano-5-iodo-phenyl)-dimethylthiocarbamic acid (3.0 g, 9.0 mmol) in anhydrous N,N-dimethylformamide (30 mL) under argon was added dropwise 25% sodium methoxide in methanol (6.1 mL, 27.1 mmol, 3.0 eq) at 0° C. The resultant yellow reaction was stirred at room temperature for 1 h. The reaction mixture was poured into cold 2N HCl (100 mL) and then extracted with ethyl acetate. The combined organic layers were dried, filtered, and evaporated under reduced pressure to give crude 2-cyano-5-iodothiophenol. The crude material thus obtained was used directly without further purification.

Step 4: Preparation of the intermediate 2-[(2',4'-dichlorophenyl)carbonyl-3-amino]-6-iodo benzothiophene

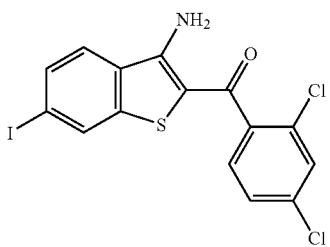

To crude 2-cyano-5-iodothiophenol (3.0 mmol) and 2,2',4'-trichloro-acetophenone (673 mg, 3.0 mmol) in anhydrous N,N-dimethylformamide (10 mL) was added powdered potassium hydroxide (832 mg, 6.0 mmol, 2.0 eq). The reaction mixture was stirred under argon at 80° C. for 16 h. The brown reaction mixture was cooled and diluted with ethyl acetate and water. The organic layer was washed with saturated aqueous ammonium chloride, water, brine, and dried. The solvents were evaporated under reduced pressure, and the crude product was purified on the MPLC (Biotage) eluted with 20% ethyl acetate-hexane, followed by trituration from hexane, to give 1.012 g (75.0%) of the benzothiophene. $^1$H-NMR (Acetone-$d_6$) δ 8.24 (d, J=1.5 Hz, 1H), 8.05 (d, J=8.4 Hz, 1H). 7.94 (broad, s; 2H); 7.79 (dd; J=8.4; 15 Hz, 1H); 7.65 (dd, J=1.5, 0.9 Hz, 1H). 7.56 (m, 2H); MS ES (MH$^+$=448/450); $R_f$=0.58 (30% ethyl acetate-hexane).

Step 5: Preparation of the title compound: [3-amino-6-(3-pyridinyl)-1-benzothiophene-2-yl](2,4-dichloro-phenyl)methanone

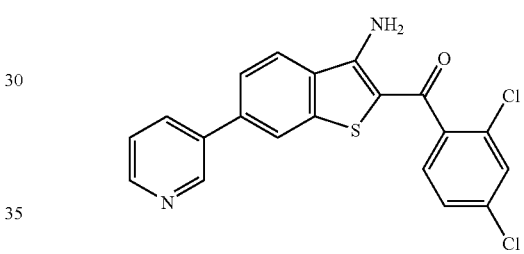

A solution of (3-amino-6-iodo-1-benzothiphene-2-yl)(2,4-dichlorophenyl)methanone (150 mg, 0.33 mmol) in 1,2-dimethoxyethane was degassed with argon for 30 min. At this time, tetrakis(triphenyl phosphine)palladium(0), (39 mg, 0.03 mmol, 0.1 eq) was added, followed by pyridine-3-boronic acid (41 mg, 0.33 mmol, 1.0 eq) and 2M aqueous Na$_2$CO$_3$ (4.0 mL). The reaction was bubbled with argon for another 10 min and then heated to 80° C. overnight (18 h). The reaction was diluted with ethyl acetate, washed with water, brine, and dried over magnesium sulfate. The solvent was removed at reduced pressure, and the crude product was purified on the MPLC (Biotage) eluted with 45 to 65% ethyl acetate-hexane to afford 37.5 mg (28.1%) of a yellow solid as the product. $^1$H-NMR (Acetone-$d_6$) δ 8.84 (dd, J=2.7, 0.6 Hz, 1H), 8.49 (dd, J=4.8, 1.8 Hz, 1H), 8.21 (dd, J=8.4, 0.6 Hz, 1H), 8.00 (m, 2H), 7.87 (broad, s, 2H), 7.68 (dd, J=8.4, 1.5 Hz, 1H), 7.53 (d, J=1.8 Hz, 1H), 7.46 (s, 1H); 7.44 (d, J=1.8 Hz, 1H), 7.36 (m, 1H) LC-MS (ES MH$^+$=399, RT=2.71 min). $R_f$=0.08 (50% ethyl acetate-hexane).

Other compounds, appearing in Table 6 were prepared in like manner as described above by choosing the appropriate starting materials that are readily available and/or the synthesis of which is taught herein, and using the process described above or other standard chemical processes known in the art.

TABLE 6

Examples Synthesized using Method G

| Example | Structure | $R_f$ (TLC solvent) Or RT (min)* | LC/MS ([M + H]+) | Synthesis of (III)** | Synthesis of (VI) or (VII)** | Synthesis of (I) |
|---|---|---|---|---|---|---|
| 222 | 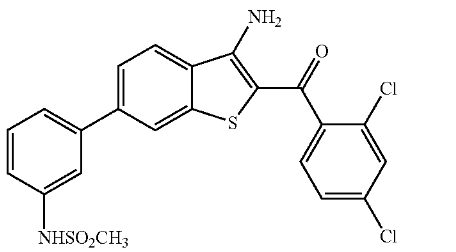 | $R_f$ = 0.08, HEX/EtOAc = 50/50 | 491/493 | comm | comm | G |
| 223 | 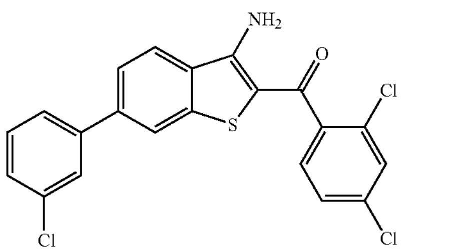 | $R_f$ = 0.58, HEX/EtOAc = 70/30 | 434 | comm | comm | G |
| 224 | 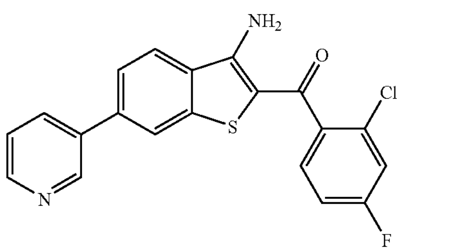 | $R_f$ = 0.08, HEX/EtOAc = 50/50 | 383 | A-4 | comm | G |
| 225 | 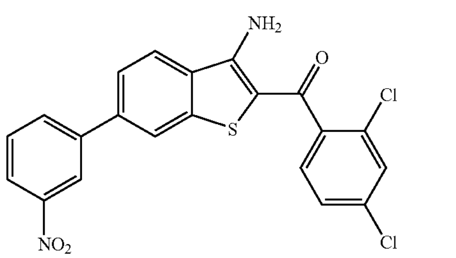 | $R_f$ = 0.45, HEX/EtOAc = 70/30 | 443/445 | comm | comm | G |
| 226 | 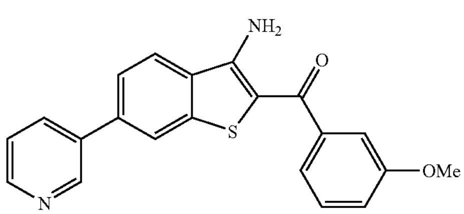 | $R_f$ = 0.08, HEX/EtOAc = 60/40 | 361 | comm | comm | G |
| 227 | 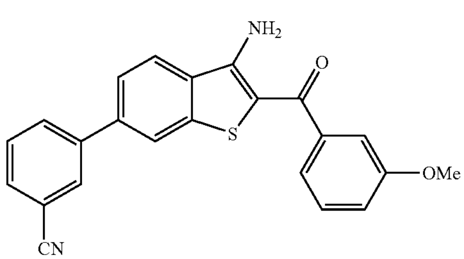 | $R_f$ = 0.32, HEX/EtOAc = 70/30 | 385 | comm | comm | G |

TABLE 6-continued

Examples Synthesized using Method G

| Example | Structure | $R_f$ (TLC solvent) Or RT (min)* | LC/MS ([M + H]+) | Synthesis of (III)** | Synthesis of (VI) or (VII)** | Synthesis of (I) |
|---------|-----------|----------------------------------|------------------|----------------------|------------------------------|------------------|
| 228 | 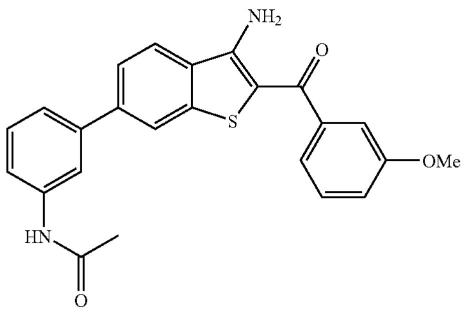 | $R_f$ = 0.12, HEX/EtOAc = 60/40 | 417 | comm | comm | G |
| 229 | 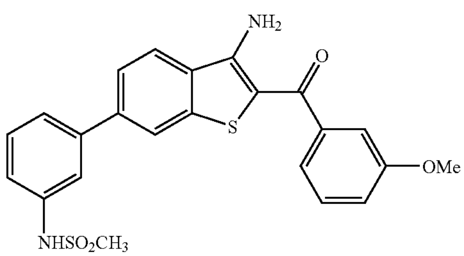 | $R_f$ = 0.14, HEX/EtOAc = 60/40 | 453 | comm | comm | G |
| 230 | 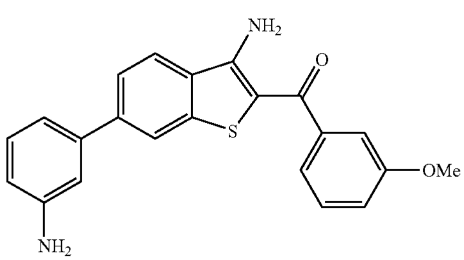 | $R_f$ = 0.10, HEX/EtOAc = 70/30 | 375 | comm | comm | G |

Footnotes:
*The following are the LCMS conditions: HPLC - electrospray mass spectra (HPLC ES-MS) were obtained using a Gilson HPLC system equipped with two Gilson 306 pumps, a Gilson 215 Autosampler, a Gilson diode array detector, a YMC Pro C-18 column (2 × 23 mm, 120 A), and a Micromass LCZ single quadrupole mass spectrometer with z-spray electrospray ionization. Spectra were scanned from 120-1000 amu over 2 seconds. ELSD (Evaporative Light Scattering Detector) data was also acquired as an analog channel. Gradient elution was used with Buffer A as 2% acetonitrile in water with 0.02% TFA and Buffer B as 2% water in Acetonitrile with 0.02% TFA at 1.5 mL/min. Samples were eluted as follows: 90% A for 0.5 min ramped to 95% B over 3.5 min and held at 95% B for 0.5 min and then the column is brought back to initial conditions over 0.1 min. Total run time is 4.8 min.
**comm means commercially available.

Other compounds of Formula I may be prepared using the methods described herein or other methods known in the art, and using the appropriate starting materials and/or intermediates that would be readily recognized by those skilled in the art.

TABLE 7
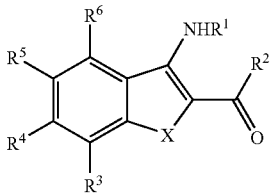
| Example | X | R¹ | R² | R³ | R⁴ | R⁵ | R⁶ |
|---|---|---|---|---|---|---|---|
| 231 | O | PhCO— | 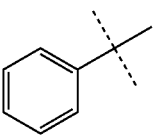 | H | 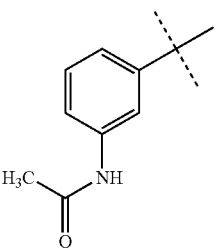 | H | H |
| 232 | O | H | 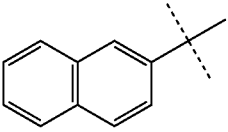 | H | 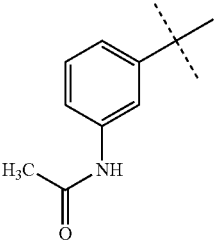 | H | H |
| 233 | S | H | 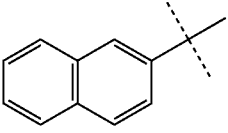 | H | 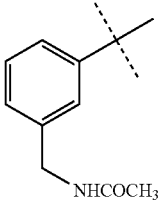 | H | H |
| 234 | O | H | 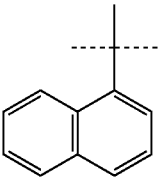 | H | 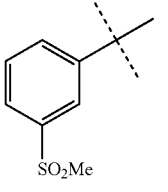 | H | H |
| 235 | O | H | 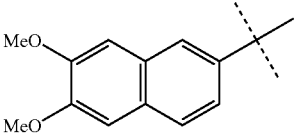 | H | 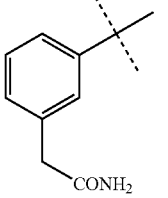 | H | H |

TABLE 7-continued
(I)
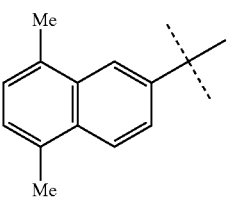
| Example | X | R¹ | R² | R³ | R⁴ | R⁵ | R⁶ |
|---|---|---|---|---|---|---|---|
| 236 | O | H | 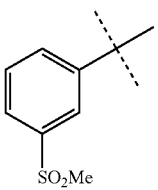 | H | 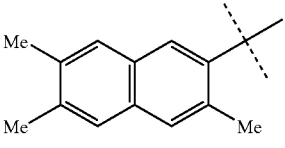 | H | H |
| 237 | S | H | 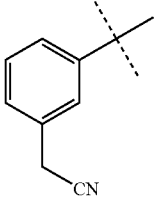 | H | 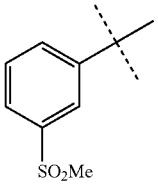 | H | H |
| 238 | O | H | 4-Cl—Ph— | H | 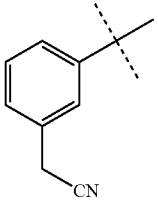 | H | H |
| 239 | O | H | 3-NO₂Ph— | H | 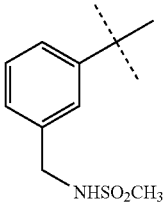 | H | H |
| 240 | S | H | 4-CN—Ph— | H | 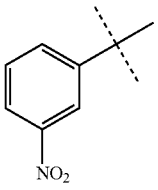 | H | H |
| 241 | S | H | 2,4,6-triCl—Ph— | H |  | H | H |

TABLE 7-continued
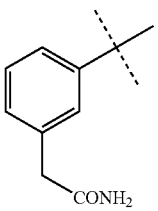
(I)
| Example | X | R¹ | R² | R³ | R⁴ | R⁵ | R⁶ |
|---|---|---|---|---|---|---|---|
| 242 | O | H | 3,4,5-triMe—Ph | H |  | OH | H |
| 243 | O | H | 4-CF₃—Ph— | H | 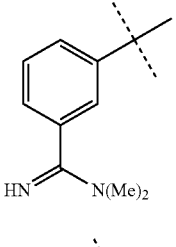 | H | H |
| 244 | O | H | 3-CH₃CO—Ph | H | 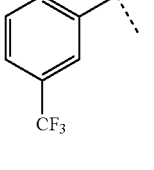 | H | H |
| 245 | O | H | 4-(COOH)—Ph— | H | 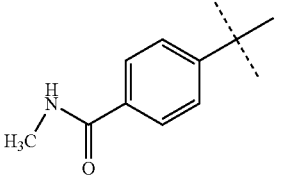 | H | H |
| 246 | O | Et | 3-(CO₂Et)—Ph— | H | 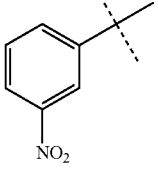 | H | H |
| 247 | O | H | 4-[CON(Me)₂]—Ph | H |  | H | H |

TABLE 7-continued
(I)
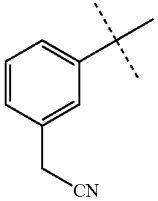
| Ex-ample | X | R¹ | R² | R³ | R⁴ | R⁵ | R⁶ |
|---|---|---|---|---|---|---|---|
| 248 | O | H | 3-(NHCH₂CH₂SO₂Me)—Ph | H | 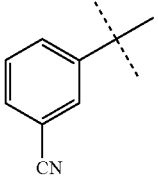 | H | H |
| 249 | O | Me | 4-(NHSO₂Me)—Ph | H | 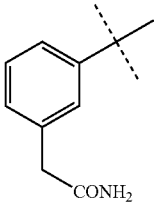 | H | H |
| 250 | O | H | 3-(NHCOEt)—Ph | H | 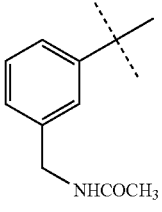 | H | H |
| 251 | O | H | 4-(NH—(CH₂)₄—COMe)—Ph | H | 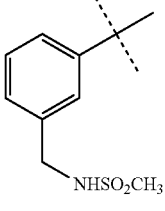 | OMe | H |
| 252 | S | H | 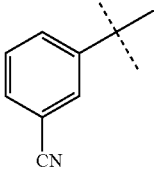 | H | | H | H |
| 253 | S | H | | H | | H | H |

TABLE 7-continued
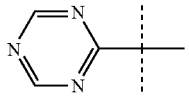
(I)
| Example | X | R¹ | R² | R³ | R⁴ | R⁵ | R⁶ |
|---|---|---|---|---|---|---|---|
| 254 | O | H | 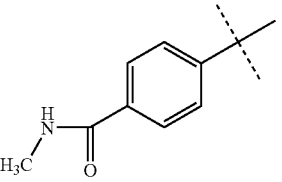 | H | 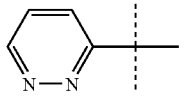 | H | H |
| 255 | O | H | 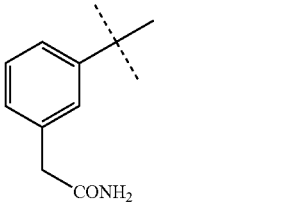 | H | 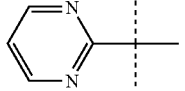 | H | H |
| 256 | O | Ac | 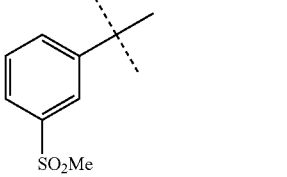 | H | 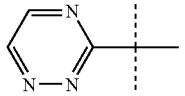 | H | H |
| 257 | O | H | 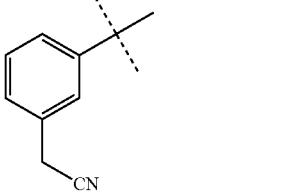 | H | 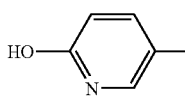 | Me | H |
| 258 | O | H | 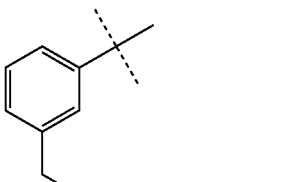 | H | 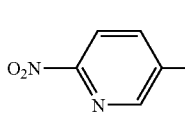 | H | H |
| 259 | O | H | 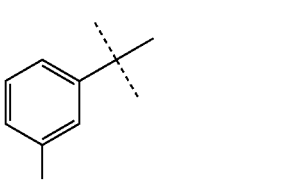 | H |  | H | H |

TABLE 7-continued
(I)
| Example | X | R¹ | R² | R³ | R⁴ | R⁵ | R⁶ |
|---|---|---|---|---|---|---|---|
| 260 | O | H | 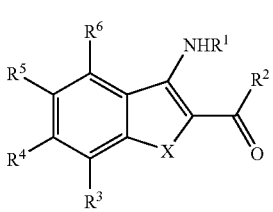 | H | 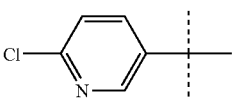 | H | H |
| 261 | S | H | 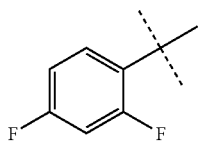 | H | 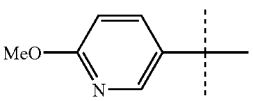 | Cl | H |
| 262 | S | H | 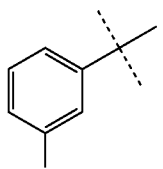 | H | 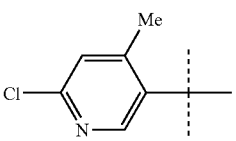 | H | H |
| 263 | O | H | 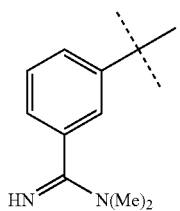 | H | 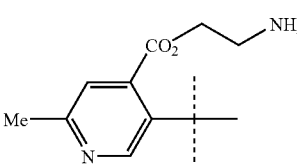 | H | OH |
| 264 | O | Me | 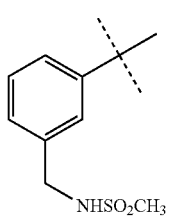 | H | 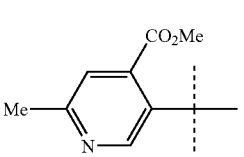 | H | H |
| 265 | O | H | 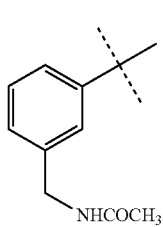 | H | 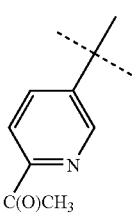 | Me | H |

TABLE 7-continued
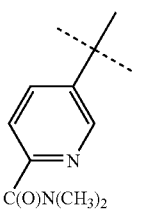
(I)
| Example | X | R¹ | R² | R³ | R⁴ | R⁵ | R⁶ |
|---|---|---|---|---|---|---|---|
| 266 | O | H | 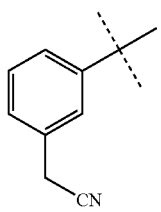 | H | 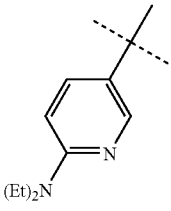 | Cl | H |
| 267 | O | Et | 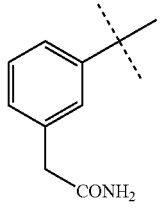 | H | 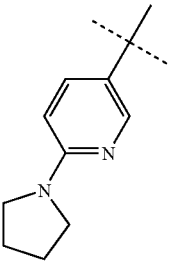 | CF₃ | H |
| 268 | O | H | 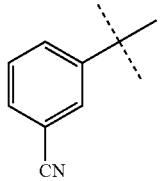 | H | 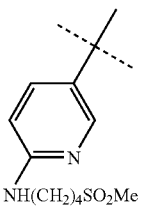 | OH | H |
| 269 | O | H | 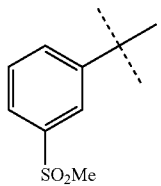 | H | 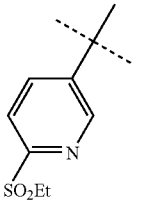 | F | H |
| 270 | S | Et | 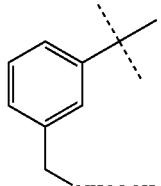 | H |  | EtO | H |

TABLE 7-continued (I)

| Example | X | R¹ | R² | R³ | R⁴ | R⁵ | R⁶ |
|---|---|---|---|---|---|---|---|
| 271 | O | Et | 5-(Et(OC)CN)pyridin-2-yl | H | 3-(HN=C-N(Me)₂)phenyl | Cl | H |
| 272 | O | Me | 5-(Me(O)C(H₂C)₃N)pyridin-2-yl | H | 3-(CH₂NHSO₂CH₃)phenyl | CF₃O | H |
| 273 | O | H | furan-3-yl | H | 3-(CH₂CONH₂)phenyl | CH₃ | H |
| 274 | O | H | thiazol-4-yl | H | 3-(CH₂CN)phenyl | H | H |
| 275 | O | H | isoxazol-4-yl | H | 3-CN-phenyl | H | H |
| 276 | S | H | 1-Me-imidazol-4-yl | H | 3-(HN=C-N(Me)₂)phenyl | H | H |

TABLE 7-continued
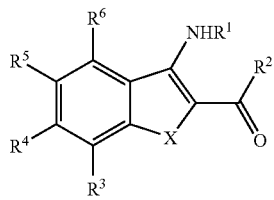
| Example | X | R¹ | R² | R³ | R⁴ | R⁵ | R⁶ |
|---|---|---|---|---|---|---|---|
| 277 | S | H | oxazol-4-yl | H | 3-(NHCOCH₃)phenyl | H | H |
| 278 | O | H | 1-methyl-1,2,4-triazol-3-yl | H | 3-(CH₂CN)phenyl | H | H |
| 279 | S | H | 1,2,3-thiadiazol-4-yl | H | 3-NO₂-phenyl | H | H |
| 280 | S | H | thiophen-3-yl | H | 3-(CH₂NHSO₂CH₃)phenyl | Cl | H |
| 281 | O | H | 2,4,5-trimethylfuran-3-yl | H | 3-(CH₂CONH₂)phenyl | F | H |
| 282 | O | H | 2,5-dichloro-4-methylthiophen-3-yl | H | 3-(C(=NH)N(Me)₂)phenyl | Me | H |

TABLE 7-continued

| Example | X | R¹ | R² | R³ | R⁴ | R⁵ | R⁶ |
|---|---|---|---|---|---|---|---|
| 283 | O | H | 3-tert-butyl-furan-2-carboxylic acid 2-methoxy-ethyl ester | H | 3-cyanophenyl | H | OMe |
| 284 | S | Me | 3,5-bis(methoxycarbonyl)furan-4-yl | H | 3-(NHCOCH₃-methyl)phenyl | OH | H |
| 285 | O | H | 4-acetyl-furan-2-yl | H | 3-(SO₂Me)phenyl | H | H |
| 286 | O | H | 4-(N,N-dimethylcarbamoyl)thiophen-2-yl | H | 3-(CH₂CN)phenyl | H | H |
| 287 | O | Et | 4-(N,N-diethylamino)thiophen-3-yl | H | 3-nitrophenyl | H | H |
| 288 | O | H | 4-(3-hydroxypropylamino)thiophen-3-yl | H | 4-propanoylphenyl | OH | H |

TABLE 7-continued
(I)
| Example | X | R¹ | R² | R³ | R⁴ | R⁵ | R⁶ |
|---|---|---|---|---|---|---|---|
| 289 | O | Me | 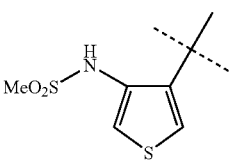 | H | 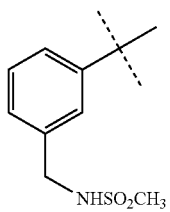 | H | H |
| 290 | O | H | 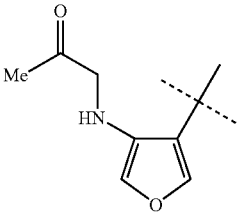 | H | 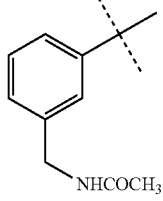 | H | H |
| 291 | O | H | 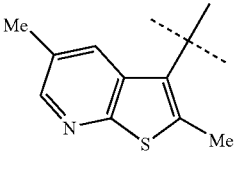 | H | 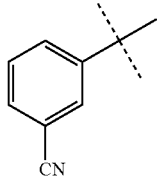 | H | Cl |
| 292 | S | H | 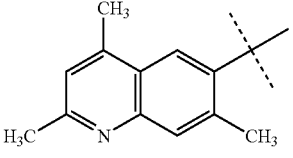 | H | 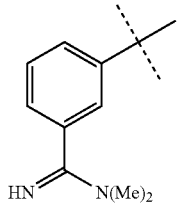 | H | H |
| 293 | S | H | 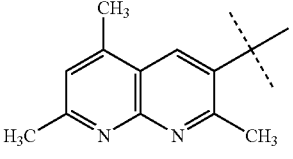 | H | 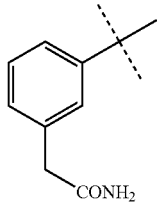 | H | H |
| 294 | O | H | 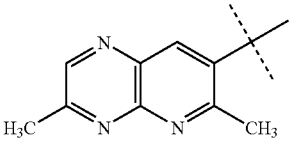 | H | 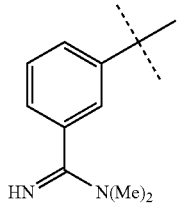 | H | CF₃ |

TABLE 7-continued
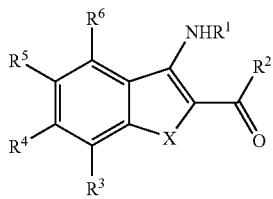
(I)
| Example | X | R¹ | R² | R³ | R⁴ | R⁵ | R⁶ |
|---|---|---|---|---|---|---|---|
| 295 | O | H | quinolin-3-yl | H | 3-(SO₂Me)phenyl | OMe | H |
| 296 | O | H | 2-(piperidin-1-yl)quinolin-3-yl | H | 3-(CH₂NHCOCH₃)phenyl | OH | H |
| 297 | O | Et | 5,8-bis(CO₂Et)-2-hydroxyquinolin-3-yl | H | 3-(NHCOCH₃)phenyl | Me | H |
| 298 | O | H | 3-methylisoxazolo[5,4-b]pyridin-5-yl | H | 4-(COCH₂CH₃)phenyl | Cl | H |
| 299 | O | H | 3-((Me)₂NOC)isothiazolo[5,4-b]pyridin-5-yl | H | 3-CN-phenyl | F | H |
| 300 | O | H | 2-(CF₃)quinolin-3-yl | H | 3-(NHCOCH₃)phenyl | Et | H |

TABLE 7-continued
(I)
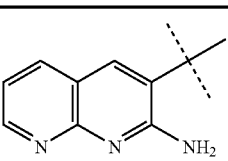
| Example | X | R¹ | R² | R³ | R⁴ | R⁵ | R⁶ |
|---|---|---|---|---|---|---|---|
| 301 | S | H | 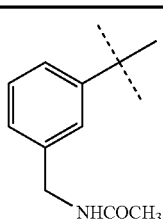 | H | 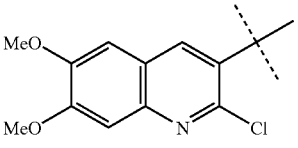 | CF₃O | H |
| 302 | S | Me | 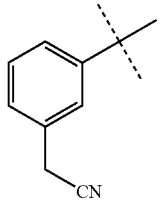 | H | 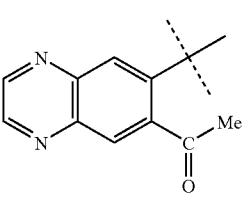 | H | H |
| 303 | O | H | 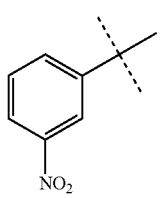 | H | 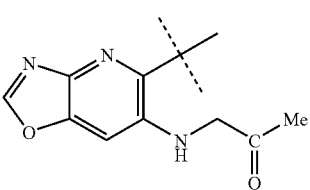 | H | H |
| 304 | O | H | 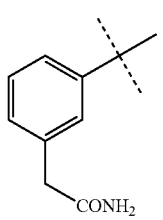 | H | 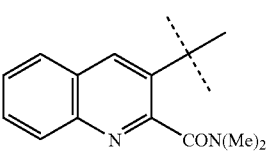 | Me | H |
| 305 | O | H | 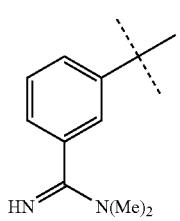 | H | 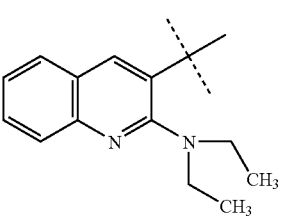 | OH | H |
| 306 | O | H | 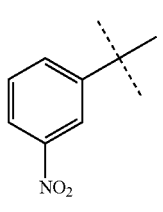 | H |  | H | H |

TABLE 7-continued
(I)
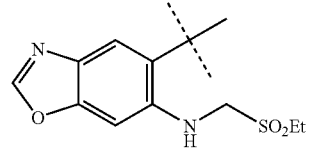
| Example | X | R¹ | R² | R³ | R⁴ | R⁵ | R⁶ |
|---|---|---|---|---|---|---|---|
| 307 | O | H | 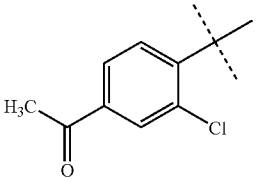 | H | 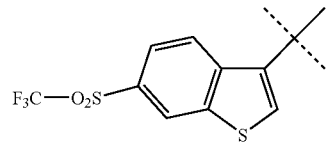 | H | H |
| 308 | O | H | 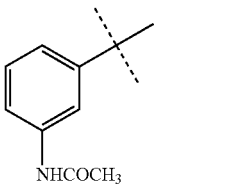 | H | 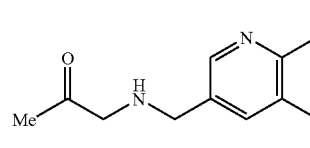 | H | OH |
| 309 | O | H | 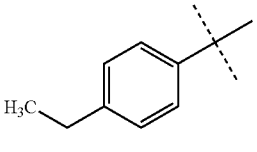 | H | 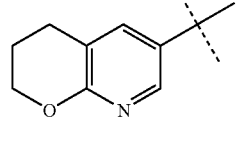 | H | H |
| 310 | O | H | 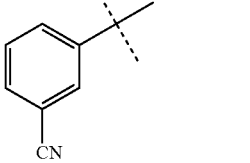 | H | 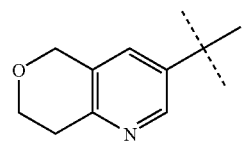 | H | H |
| 311 | O | H | 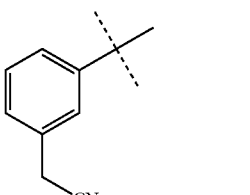 | H | 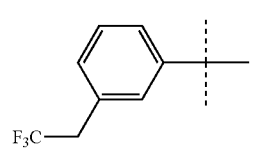 | OH | H |
| 312 | S | H | 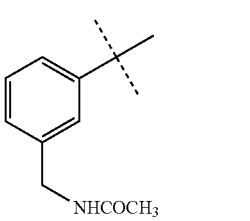 | Cl |  | H | F |

TABLE 7-continued
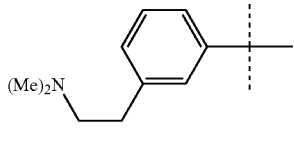
(I)
| Ex-ample | X | R¹ | R² | R³ | R⁴ | R⁵ | R⁶ |
|---|---|---|---|---|---|---|---|
| 313 | O | H | 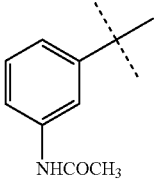 | Me | 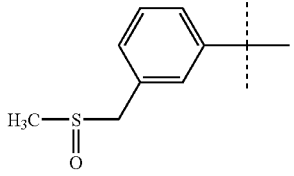 | H | Cl |
| 314 | O | H | 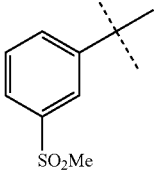 | CF₃ | 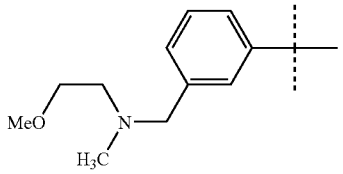 | H | H |
| 315 | O | H | 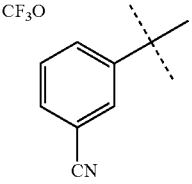 | CF₃O | 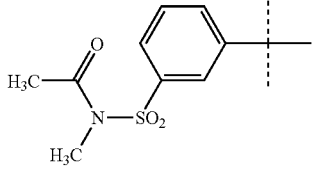 | OMe | H |
| 316 | O | H | 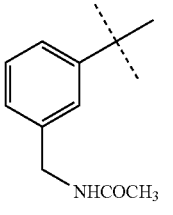 | OH | 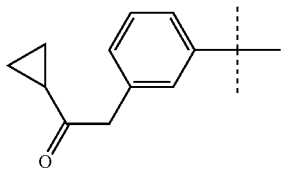 | H | OMe |
| 317 | O | H | 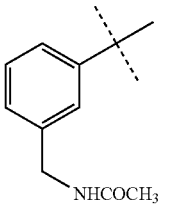 | OH | 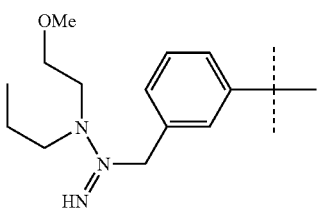 | H | Me |
| 318 | O | H | 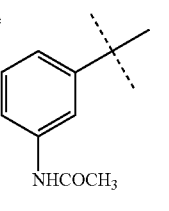 | OMe |  | H | H |

TABLE 7-continued
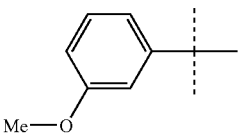
(I)
| Example | X | R¹ | R² | R³ | R⁴ | R⁵ | R⁶ |
|---|---|---|---|---|---|---|---|
| 319 | O | H | 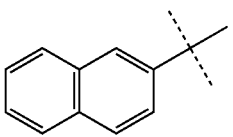 | H | 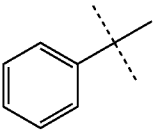 | H | H |
| 320 | O | H | 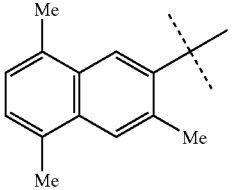 | H | 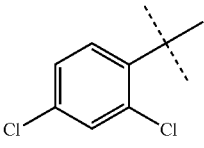 | H | H |
| 321 | O | H | 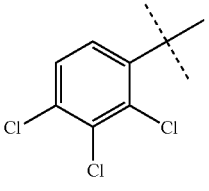 | H | 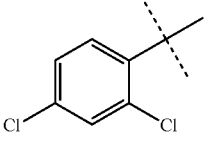 | H | H |
| 322 | O | H | 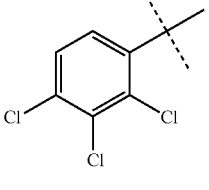 | H | 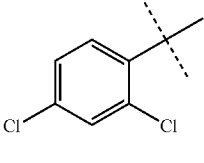 | H | H |
| 323 | O | H | 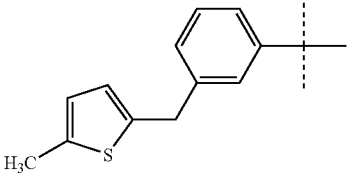 | H | 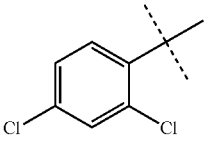 | Me | H |
| 324 | O | H | 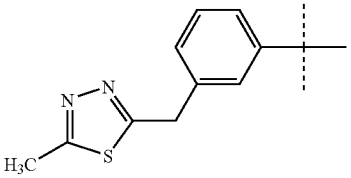 | H | 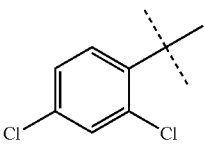 | H | H |
| 325 | O | H | 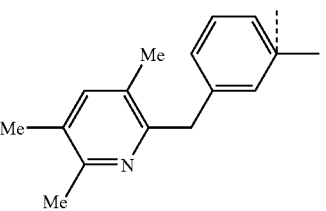 | H |  | H | H |

TABLE 7-continued
(I)
| Example | X | R¹ | R² | R³ | R⁴ | R⁵ | R⁶ |
|---|---|---|---|---|---|---|---|
| 326 | O | H | 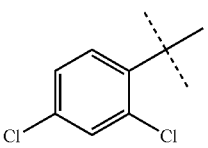 | H | 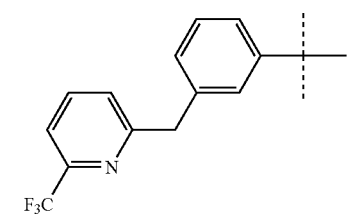 | H | H |
| 327 | O | H | 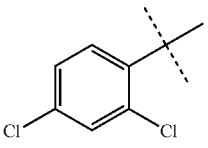 | H | 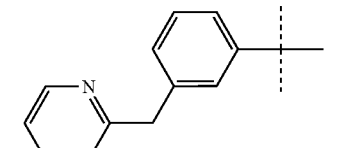 | H | Cl |
| 328 | O | H | 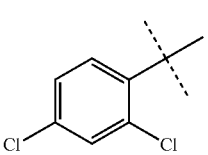 | H | 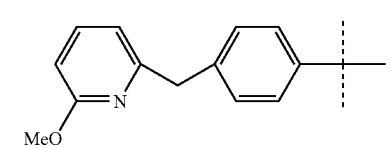 | H | H |
| 329 | O | H | 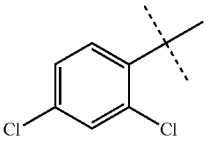 | H | 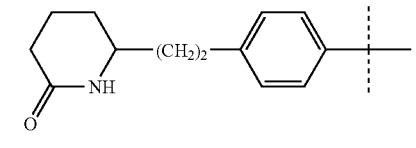 | H | H |
| 330 | O | H | 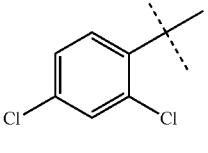 | H | 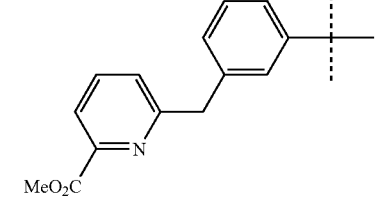 | H | H |
| 331 | O | H | 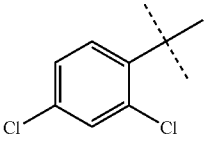 | H | 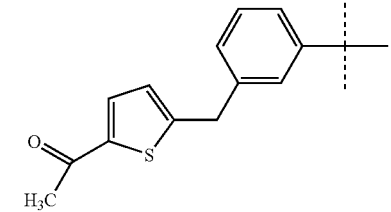 | H | OH |

TABLE 7-continued (I)

| Example | X | R¹ | R² | R³ | R⁴ | R⁵ | R⁶ |
|---|---|---|---|---|---|---|---|
| 332 | O | H | 2,4-dichlorophenyl | H | 5-(3-tert-butylbenzyl)-N,N-dimethylfuran-2-carboxamide | Me | H |
| 333 | O | H | 2,4-dichlorophenyl | H | 2-(3-tert-butylbenzyl)-N,N-diethylpyrimidin-4-amine | H | H |
| 334 | O | H | 2,4-dichlorophenyl | H | 2-(3-tert-butylbenzyl)-3-(methylsulfonylmethylamino)furan | H | H |
| 335 | O | H | 2,4-dichlorophenyl | H | 4-(4-tert-butylbenzyl)-1-methylimidazole | H | MeO |
| 336 | O | H | 2,4-dichlorophenyl | H | 4-tert-butyl-N,N-dimethylbenzamidine | H | H |
| 337 | O | H | 2,4-dichlorophenyl | H | N-(4-tert-butylphenyl)-N-methyl-methanesulfonylmethylamine | MeO | H |
| 338 | O | H | 2,4-dichlorophenyl | H | 1-(N-(4-tert-butylphenyl)-N-methylamino)propan-2-one | H | H |

TABLE 7-continued
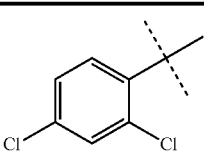
(I)
| Example | X | R¹ | R² | R³ | R⁴ | R⁵ | R⁶ |
|---|---|---|---|---|---|---|---|
| 339 | O | H | 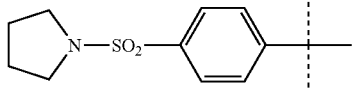 | H | 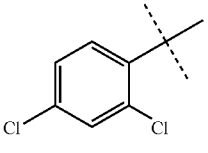 | H | H |
| 340 | O | H | 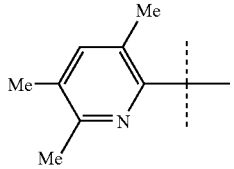 | H | 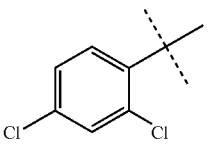 | H | Cl |
| 341 | O | H | 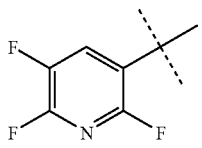 | H | 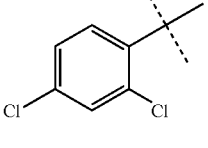 | H | H |
| 342 | O | H | 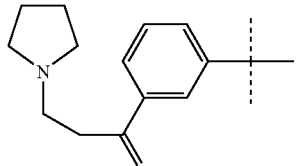 | H | 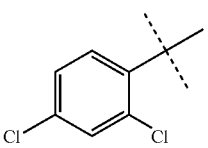 | H | H |
| 343 | O | H | 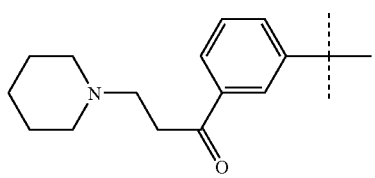 | H | 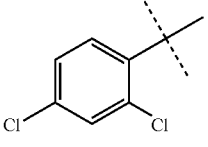 | OH | H |
| 344 | O | H | 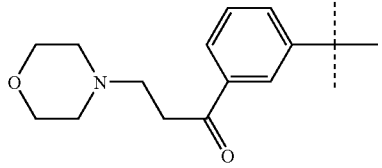 | H | 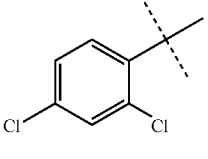 | H | H |
| 345 | O | H | 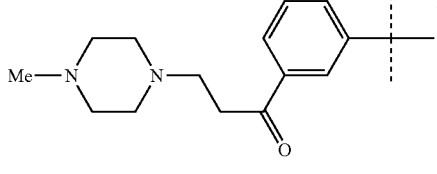 | H |  | H | H |

TABLE 7-continued
(I)
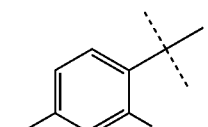
| Example | X | R¹ | R² | R³ | R⁴ | R⁵ | R⁶ |
|---|---|---|---|---|---|---|---|
| 346 | O | H | 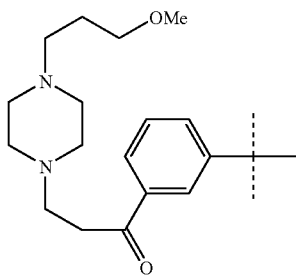 | H | 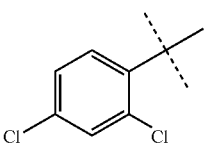 | H | H |
| 347 | O | H | 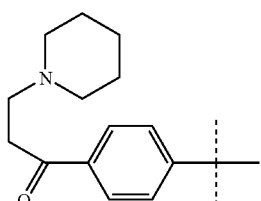 | H | 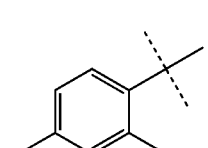 | H | H |
| 348 | O | H | 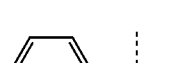 | OH | 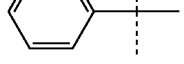 | H | H |
| 349 | O | H | 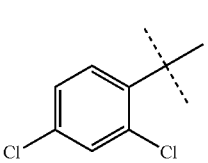 | H | 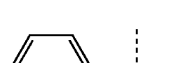 | H | OH |
| 350 | O | H | 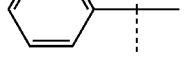 | OH | 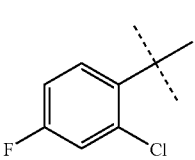 | H | H |
| 351 | O | H | 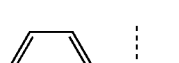 | OH | 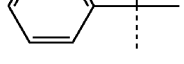 | H | H |
| 352 | O | H | 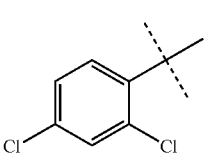 | H | 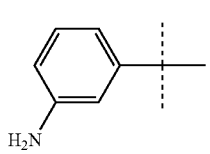 | OH | H |

TABLE 7-continued
(I)
| Example | X | R¹ | R² | R³ | R⁴ | R⁵ | R⁶ |
|---|---|---|---|---|---|---|---|
| 353 | S | H | 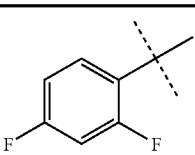 | H | 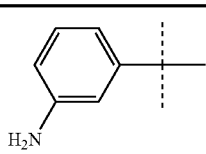 | H | OH |
| 354 | O | H | 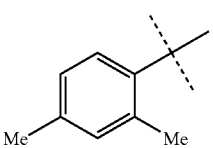 | OH | 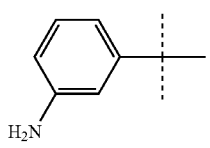 | OH | H |
| 355 | O | H | 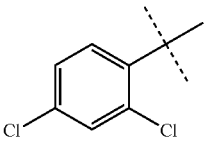 | F | 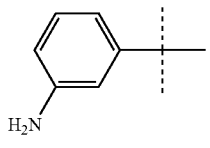 | H | H |
| 356 | O | H | 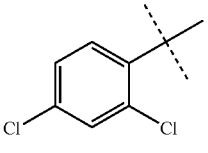 | H | 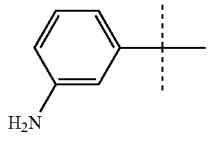 | H | F |
| 357 | O | H | 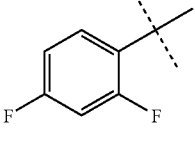 | F | 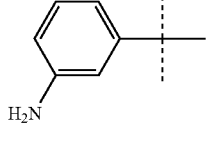 | H | F |
| 358 | O | H | 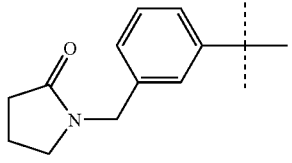 | H | 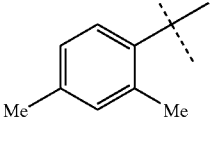 | H | H |
| 359 | O | H | 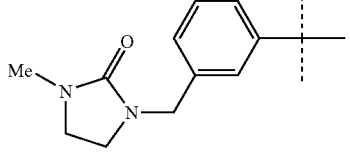 | H | 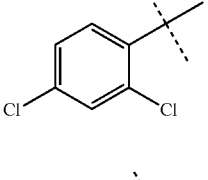 | H | H |
| 360 | O | H | 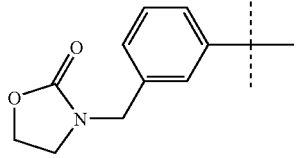 | H | 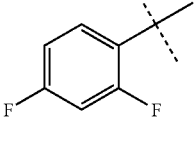 | H | H |

TABLE 7-continued

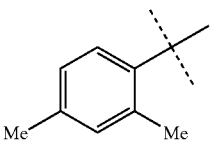

(I)

| Example | X | R¹ | R² | R³ | R⁴ | R⁵ | R⁶ |
|---|---|---|---|---|---|---|---|
| 361 | S | H | 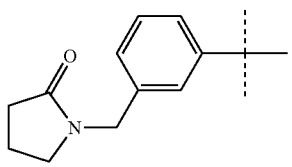 | H | 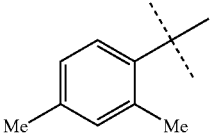 | H | H |
| 362 | O | H | 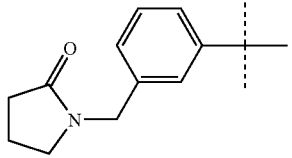 | OH | 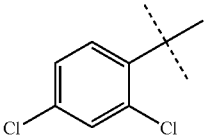 | H | H |
| 363 | O | H | 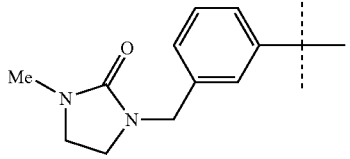 | H | 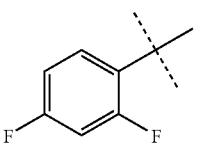 | OH | H |
| 364 | O | H | 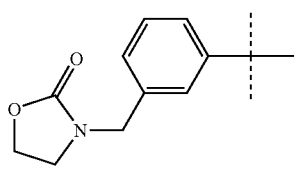 | H | 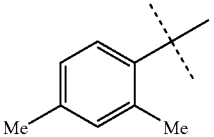 | OH | H |
| 365 | S | H | 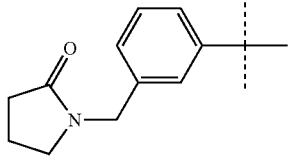 | H |  | H | OH |

COMPOSITIONS USEFUL FOR THE METHOD OF THIS INVENTION

A compound of Formula I is useful in this method for treating the conditions described further herein when it is formulated as a pharmaceutically acceptable composition. A pharmaceutically acceptable composition is a compound of Formula I in admixture with a pharmaceutically acceptable carrier. A pharmaceutically acceptable carrier is any carrier that is relatively non-toxic and innocuous to a patient at concentrations consistent with effective activity of the active ingredient so that any side effects ascribable to the carrier do not vitiate the beneficial effects of the active ingredient.

Commonly used pharmaceutical ingredients which can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC$—$CClF_2$ and $CClF_3$);

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzothonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate);

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection);

chelating agents (examples include but are not limited to edetate disodium and edetic acid);

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia; cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate);

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas);

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures);

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

The compounds of the present invention can be administered with pharmaceutically-acceptable carriers well known in the art using any effective conventional dosage unit forms formulated as immediate, slow or timed release preparations, including, for example, the following.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitan monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or susDending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations which are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52(5), 238-311; Strickley, R. G "Parenteral Formulations of Small Molecule Therapeutics Marketed in the United States (1999)—Part-1 "*PDA Journal of Pharmaceutical Science & Technology* 1999, 53(6), 324-349; and Nema, S. et at, "Excipients and Their Use in Injectable Products" *PDA Journal of Pharmaceutical Science & Technology* 1997, 51(4), 166-171.

It is believed that one skilled in the art, utilizing the preceding information, can utilize the present invention to its fullest extent. Nevertheless, the following are examples of pharmaceutical formulations that can be used in the method of the present invention. They are for illustrative purposes only, and are not to be construed as limiting the invention in any way.

Pharmaceutical compositions according to the present invention can be further illustrated as follows:

Sterile IV Solution: A 5 mg/mL solution of the desired compound of this invention is made using sterile, injectable water, and the pH is adjusted if necessary. The solution is diluted for administration to 1-2 mg/mL with sterile 5% dextrose and is administered as an IV infusion over 60 min.

Lyophilized powder for IV administration: A sterile preparation can be prepared with (i) 100-1000 mg of the desired compound of this invention as a lypholized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 min.

Intramuscular suspension: The following solution or suspension can be prepared, for intramuscular injection:
  50 mg/mL of the desired, water-insoluble compound of this invention
  5 mg/mL sodium carboxymethylcellulose
  4 mg/mL TWEEN 80
  9 mg/mL sodium chloride
  9 mg/mL benzyl alcohol Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit was 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Cancer

The compounds and compositions described herein can be used to treat or prevent hyper-proliferative disorders. An effective amount of a compound or composition of this invention can be administered to a patient in need thereof in order to achieve a desired pharmacological effect. A patient, for the purpose of this invention, is a mammal, including a human, in need of treatment (including prophylactic treatment) for a particular disorder described further herein. A pharmaceutically effective amount of compound or composition is that amount which produces a desired result or exerts an influence on the particular hyper-proliferative disorder being treated.

Hyper-proliferative disorders include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

The disorders described above have been well characterized in humans, but also exist with a similar etiology in other mammals. Accordingly, the method of this invention can be administered to mammals, including humans, in need thereof for the treatment of angiogenesis and/or proliferative dependent disorders.

The utility of the compounds of the present invention can be illustrated, for example, by their activity in vitro in the in vitro tumor cell proliferation assay described below. The link between activity in tumor cell proliferation assays in vitro and anti-tumor activity in the clinical setting has been very well established in the art. For example, the therapeutic utility of taxol (Silvestrini et al. *Stem Cells* 1993, 11(6), 528-35), taxotere (Bissery et al. *Anti Cancer Drugs* 1995; 6(3); 339), and topoisomerase inhibitors (Edelman et al. *Cancer Chemother. Pharmacol.* 1996, 37(5), 385-93) were demonstrated with the use of in vitro tumor proliferation assays.

The compounds and compositions described herein, including salts and esters thereof, exhibit anti-proliferative activity and are thus useful to prevent or treat the disorders associated with hyper-proliferation. The following assay is one of the methods by which compound activity relating to treatment of the disorders identified herein can be determined.

In Vitro Tumor Cell Proliferation Assay

The adherent tumor cell proliferation assay used to test the compounds of the present invention involves a readout called Cell Titre-Glo developed by Promega (Cunningham, B A "A Growing Issue: Cell Proliferation Assays. Modern kits ease quantification of cell growth" *The Scientist* 2001, 15(13), 26, and Crouch, S P et al., "The use of ATP bioluminescence as a measure of cell proliferation and cytotoxicity" *Journal of Immunological Methods* 1993, 160, 81-88).

H460 cells (lung carcinoma, purchased from ATCC) are plated in 96-well plates at 3000 cells/well in complete media with 10% Fetal Calf Serum and incubated 24 hours at 37° C. Twenty-four hours after plating, test compounds are added over a final concentration range of 10 nM to 20 µM in serial dilutions at a final DMSO concentration of 0.2%. Cells are incubated for 72 hours at 37° C. in complete growth media after addition of the test compound. On day 4, using a Promega Cell Titer Glo Luminescent® assay kit, the cells are lysed and 100 microliters of substrate/buffer mixture is added to each well, mixed and incubated at room temperature for 8 minutes. The samples are read on a luminometer to measure the amount of ATP present in the cell lysates from each well, which corresponds to the number of viable cells in that well. Values read at 24-hour incubation are subtracted as Day 0. For determination of $IC_{50}$'s, a linear regression analysis can be used to determine drug concentration which results in a 50% inhibition of cell proliferation using this assay format. Compounds of this invention showed a significant inhibition of tumor cell proliferation in this assay.

Based upon the above and other standard laboratory techniques known to evaluate compounds useful for the prevention and/or treatment of the diseases or disorders described above by standard toxicity tests and by standard pharmacological assays for the determination of the prevention and/or treatment of the conditions identified above in mammals, and by comparison of these results with the results of known medicaments that are used to treat these conditions, the effective dosage of the compounds of this invention can readily be determined for prevention and/or treatment of each desired indiration. The amount of the active ingredient to be administered in the prevention and/or treatment of one of these conditions can vary widely according to such considerations as the particular compound and dosage unit employed, the mode of administration, the duration of treatment (including prophylactic treatment), the age and sex of the patient treated, and the nature and extent of the condition to be prevented and/or treated.

The total amount of the active ingredient to be administered will generally range from about 0.001 mg/kg to about 300 mg/kg, and preferably from about 0.10 mg/kg to about 150 mg/kg body weight per day. A unit dosage may contain from about 0.5 mg to about 1500 mg of active ingredient, and can be administered one or more times per day. The daily dosage for administration by injection, including intravenous; intramuscular, subcutaneous and parenteral injections, and use of infusion techniques will preferably be from 0.01 to 200 mg/kg of total body weight. The daily rectal dosage regimen will preferably be from 0.01 to 200 mg/kg of total body weight. The daily vaginal dosage regimen will preferably be from 0.01 to 200 mg/kg of total body weight. The daily topical dosage regimen will preferably be from 0.1 to 200 mg administered between one to four times daily. The transdermal concentration will preferably be that required to maintain a daily dose of from 0.01 to 200 mg/kg. The daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of administration and number of doses of a compound or composition of the present invention or a pharmaceutically acceptable salt or ester thereof can be ascertained by those skilled in the art using conventional prevention and/or treatment tests.

The compounds of this invention can be administered as the sole pharmaceutical agent or in combination with one or more other pharmaceutical agents where the combination causes no unacceptable adverse effects. For example, the compounds of this invention can be combined with other anti-hyper-proliferative or other indication agents, and the like, as well as with admixtures and combinations thereof.

For example, optional anti-hyper-proliferative agents which can be added to the composition include but are not limited to compounds listed on the cancer chemotherapy drug regimens in the 11$^{th}$ Edition of the *Merck Index*, (1996), which is hereby incorporated by reference, such as asparaginase, bleomycin: carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment and/or prevention of neoplastic diseases in *Goodman and Gilman's The Pharmacological Basis of Therapeutics* (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the composition of this invention include but are not limited to other anti-cancer agents such as epothilone, irinotecan, raloxifen and topotecan.

It is believed that one skilled in the art, using the preceding information and information available in the art, can utilize the present invention to its fullest extent. It should be apparent to one of ordinary skill in the art that changes and modifications can be made to this invention without departing from the spirit or scope of the invention as it is set forth herein.

What is claimed is:
1. A method of treating a hyper-proliferative disorder comprising administering to a patient in need thereof an effective amount of a compound of Formula I:

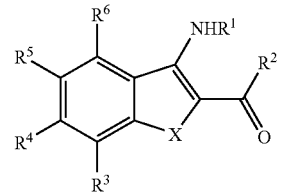

wherein
X is selected from O and S;
$R^1$ is selected from H, $(C_1-C_6)$alkyl, $C(O)(C_1-C_6)$alkyl, and benzoyl;
$R^2$ is selected from
phenyl and naphthyl, each optionally substituted with 1, 2, or 3 substituents each independently selected from
OH, CN, NO$_2$, $(C_1-C_6)$alkyl, $(C_1-C_6)$alkoxy, halo, halo$(C_1-C_6)$alkyl,
halo$(C_1-C_6)$alkoxy, $C(O)R^A$, $C(O)NR^BR^B$, $NR^BR^B$,
$NH[(C_1-C_6)alkyl,]_{0-1}S(O)_2R^B$, $NH[(C_1-C_6)alkyl]_{0-1}C(O)R^A$, and
$NH[(C_1-C_6)alkyl]_{0-1}C(O)OR^B$,
a heterocycle selected from a six membered heterocycle, a five membered heterocycle and a fused bicyclic heterocycle, each heterocycle being optionally substituted with 1, 2 or 3 substituents each independently selected from
OH, CN, NO$_2$, $(C_1-C_6)$alkyl, $(C_1-C_6)$alkoxy, halo, halo$(C_1-C_6)$alkyl,
halo$(C_1-C_6)$alkoxy, $C(O)R^A$, $C(O)NR^BR^B$, $NR^BR^B$,
$NH[(C_1-C_6)alkyl,]_{0-1}S(O)_2R^B$, $NH[(C_1-C_6)alkyl]_{0-1}C(O)R^A$, and
$NH[(C_1-C_6)alkyl]_{0-1}C(O)OR^B$,
$R^A$ is in each instance independently H, $(C_1-C_6)$alkyl, $(C_1-C_6)$alkoxy, $NR^BR^B$, or
$(C_1-C_6)$alkyl, said alkyl being optionally substituted with OH, $C(O)R^B$, halo,
$(C_1-C_3)$alkoxy, and $NR^BR^B$;
$R^B$ is in each instance independently H, $(C_3-C_6)$cycloalkyl, and
$(C_1-C_6)$alkyl, said alkyl being optionally substituted with OH, =O, halo, $(C_1-C_6)$alkoxy, $NH(C_1-C_3)$alkyl, $N[(C_1-C_3)$alkyl]$_2$, and
$NC(O)(C_1-C_3)$alkyl,
and where $R^B$, when it is attached to a N atom, is in each instance $(C_1-C_4)$alkyl, then the 2 $(C_1-C_4)$alkyl groups, taken together with the N atom to which they are attached, may be joined together to form a saturated ring,
and where $R^B$ and $R^B$ together with the N to which they are attached may form a morpholinyl ring or a piperazinyl ring optionally substituted on the available N atom with $(C_1-C_6)$alkyl, said alkyl being optionally substituted with OH, =O, $NH_2$, $(C_1-C_6)$alkoxy, $NH(C_1-C_3)$alkyl, or $N[(C_1-C_3)alkyl]_2$, and with the proviso that when $R^B$ is attached to S(O) or to $S(O)_2$, it cannot be H;

$R^3$ is selected from H, OH, CN, $(C_1-C_3)$alkyl, $(C_1-C_3)$alkoxy, halo, halo$(C_1-C_3)$alkyl, and halo$(C_1-C_3)$alkoxy;

$R^4$ is selected from piperonyl,

Y where

Y is a heterocycle optionally substituted with 1, 2, or 3 substituents each independently selected from =O, N-oxide, H, CN, $NO_2$, halo, halo$(C_1-C_6)$alkyl, OH, halo$(C_1-C_6)$alkoxy, $C(O)OR^B$, $C(NH)NR^BR^B$, $NR^BR^B$, $S(O)_{0-2}R^B$, $S(O)_2NR^BR^B$, $(C_1-C_6)$alkoxy, said alkoxy being optionally substituted with 1 or 2 substituents selected from OH, $NR^BR^B$, and $(C_1-C_3)$alkoxy, $NR^CR^C$ where $R^C$ is selected from $R^B$, $C(O)R^B$, and $S(O)_2R^B$, $C(O)R^D$ where $R^D$ is selected from $R^A$, $(C_3-C_6)$cycloalkyl, Z and $N[(C_1-C_3)alkyl]Z$ where Z is in each instance a heterocycle independently optionally substituted with CN, =O, OH, N-oxide, $NO_2$, halo, $(C_1-C_6)$alkoxy, halo$(C_1-C_3)$alkoxy, halo$(C_1-C_3)$alkyl, $S(O)_2R^B$, $S(O)_2NR^BR^B$, $NR^BR^B$, $C(O)R^A$, and $(C_1-C_6)$alkyl, said alkyl being optionally substituted with OH, $C(O)R^B$, $(C_1-C_3)$alkoxy and $NR^BR^B$;

$NR^BR^E$ where $R^E$ is selected from $C(O)R^A$, $C(O)R^B$, $S(O)_2R^B$, $S(O)_2NR^BR^B$ and $C(O)[(C_1-C_6)alkyl]Z$ where Z is optionally substituted as described above, $(C_1-C_6)$alkyl, said alkyl being optionally substituted with CN, OH, =O, halo, $(C_1-C_6)$alkoxy, $C(O)R^A$, $NR^BR^B$, $NR^CR^C$, $NR^BR^E$, $C(NH)NR^BR^B$, $S(O)_{0-2}R^B$, $S(O)_2NR^BR^B$, $C(O)R^B$ $C(O)OR^B$, Z, C(O)Z, and $C(O)N[(C_1-C_3)alkyl]Z$, where Z in each instance is independently optionally substituted as described above, phenyl and naphthyl each optionally substituted with 1, 2, or 3 substituents each independently selected from OH, CN, $NO_2$, halo, halo$(C_1-C_6)$alkyl, halo$(C_1-C_6)$alkoxy, $C(O)OR^B$, $C(NH)NR^BR^B$, $NR^BR^B$, $S(O)_{0-2}R^B$, $S(O)_2NR^BR^B$, Z, C(O)Z where Z is in each instance optionally substituted as described above, $(C_1-C_6)$alkoxy, said alkoxy being optionally substituted with 1 or 2 substituents selected from OH, $NR^BR^B$, and $(C_1-C_3)$alkoxy, $NR^CR^C$ where $R^C$ is selected from $R^B$, $C(O)R^B$, and $S(O)_2R^B$, $C(O)R^D$ where $R^D$ is selected from $R^A$, $(C_3-C_6)$cycloalkyl, and $N[(C_1-C_3)alkyl]Z$ where Z is optionally substituted as described above, $NR^BR^E$ where $R^E$ is selected from $C(O)R^A$, $C(O)R^B$, $S(O)_2R^B$, $S(O)_2NR^BR^B$ and $C(O)[(C_1-C_6)alkyl]Z$ where Z is optionally substituted as described above, $(C_1-C_6)$alkyl, said alkyl being optionally substituted with CN, OH, =O, halo, $(C_1-C_6)$alkoxy, $C(O)R^A$, $NR^BR^B$, $NR^BR^E$, $C(NH)NR^BR^B$, $S(O)_{0-2}R^B$, $S(O)_2NR^BR^B$, $C(O)R^B$, $C(O)OR^B$, Z, C(O)Z, and $C(O)N[(C_1-C_3)alkyl]Z$, where Z in each instance is independently optionally substituted as described above;

$R^5$ and $R^6$ are each independently selected from H, OH, CN, $(C_1-C_3)$alkyl, $(C_1-C_3)$alkoxy, halo, halo$(C_1-C_3)$alkyl, and halo$(C_1-C_3)$alkoxy;

or a pharmaceutically acceptable salt or ester thereof.

2. The method according to claim 1, wherein X is O.

3. The method according to claim 1, wherein X is S.

4. The method of claim 2, wherein $R^2$ is selected from phenyl, a six membered heterocycle and a 5 membered heterocycle, each being optionally substituted, and wherein $R^4$ is selected from Y and phenyl, each being optionally substituted.

5. The method of claim 3, wherein $R^2$ is selected from phenyl, a six membered heterocycle and a 5 membered heterocycle, each being optionally substituted, and wherein $R^4$ is selected from Y and phenyl, each being optionally substituted.

* * * * *